US012760296B2

(12) United States Patent
DeRosa et al.

(10) Patent No.: US 12,760,296 B2
(45) **Date of Patent: *Oct. 13, 2026**

(54) METHODS FOR PURIFICATION OF MESSENGER RNA

(71) Applicant: Translate Bio, Inc., Waltham, MA (US)

(72) Inventors: Frank DeRosa, Cambridge, MA (US); Anusha Dias, Cambridge, MA (US); Michael Heartlein, Cambridge, MA (US); Shrirang Karve, Cambridge, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/835,719

(22) Filed: Jun. 8, 2022

(65) Prior Publication Data

US 2022/0348898 A1 Nov. 3, 2022

Related U.S. Application Data

(63) Continuation of application No. 17/103,439, filed on Nov. 24, 2020, now Pat. No. 12,234,446, which is a continuation of application No. 15/936,289, filed on Mar. 26, 2018, now Pat. No. 10,876,104, which is a continuation of application No. 14/775,915, filed as application No. PCT/US2014/028441 on Mar. 14, 2014, now Pat. No. 9,957,499.

(60) Provisional application No. 61/784,996, filed on Mar. 14, 2013.

(51) Int. Cl.
*C12N 15/10* (2006.01)
*C07H 21/02* (2006.01)

(52) U.S. Cl.
CPC ............ *C12N 15/10* (2013.01); *C07H 21/02* (2013.01); *C12N 15/1017* (2013.01)

(58) Field of Classification Search
CPC ........... C12Q 1/68; C07H 21/02; C12N 15/10
See application file for complete search history.

(56) References Cited

U.S. PATENT DOCUMENTS

| | | | |
|---|---|---|---|
| 2,647,121 | A | 7/1953 | Jacoby |
| 2,717,909 | A | 9/1955 | Kosmin |
| 2,819,718 | A | 1/1958 | Goldman |
| 2,844,629 | A | 7/1958 | William et al. |
| 3,096,560 | A | 7/1963 | Liebig |
| 3,535,289 | A | 10/1970 | Yoshihara et al. |
| 3,614,954 | A | 10/1971 | Mirowski et al. |
| 3,614,955 | A | 10/1971 | Mirowski |
| 3,656,185 | A | 4/1972 | Carpentier |
| 3,805,301 | A | 4/1974 | Liebig |
| 3,945,052 | A | 3/1976 | Liebig |
| 3,995,623 | A | 12/1976 | Blake et al. |
| 4,013,507 | A | 3/1977 | Rembaum |
| 4,072,146 | A | 2/1978 | Howes |
| 4,096,860 | A | 6/1978 | McLaughlin |
| 4,099,528 | A | 7/1978 | Sorenson et al. |
| 4,106,129 | A | 8/1978 | Carpentier et al. |
| 4,134,402 | A | 1/1979 | Mahurkar |
| 4,140,126 | A | 2/1979 | Choudhury |
| 4,180,068 | A | 12/1979 | Jacobsen et al. |
| 4,182,833 | A | 1/1980 | Hicks |
| 4,227,533 | A | 10/1980 | Godfrey |
| 4,284,459 | A | 8/1981 | Patel et al. |
| 4,308,085 | A | 12/1981 | Horhold et al. |
| 4,323,525 | A | 4/1982 | Bornat |
| 4,335,723 | A | 6/1982 | Patel |
| 4,339,369 | A | 7/1982 | Hicks et al. |
| 4,355,426 | A | 10/1982 | MacGregor |
| 4,375,817 | A | 3/1983 | Engle et al. |
| 4,385,631 | A | 5/1983 | Uthmann |
| 4,401,472 | A | 8/1983 | Gerber |
| 4,406,656 | A | 9/1983 | Hattler et al. |
| 4,475,972 | A | 10/1984 | Wong |
| 4,530,113 | A | 7/1985 | Matterson |
| 4,550,447 | A | 11/1985 | Seiler, Jr. et al. |
| 4,562,596 | A | 1/1986 | Kornberg |
| 4,568,329 | A | 2/1986 | Mahurkar |
| 4,571,241 | A | 2/1986 | Christopher |
| 4,601,718 | A | 7/1986 | Possis et al. |
| 4,647,416 | A | 3/1987 | Seiler, Jr. et al. |

(Continued)

FOREIGN PATENT DOCUMENTS

| | | | |
|---|---|---|---|
| CA | 2518132 | A1 | 3/2006 |
| CA | 2807552 | A1 | 2/2012 |

(Continued)

OTHER PUBLICATIONS

Poly-A tail Scitable by Nature Education (Year: 2014).*

(Continued)

*Primary Examiner* — Anne M. Gussow

(74) *Attorney, Agent, or Firm* — LATHROP GPM LLP; James H. Velema, Esq.

(57) ABSTRACT

The present invention provides, among other things, methods of purifying messenger RNA (mRNA) including the steps of subjecting an impure preparation comprising in vitro synthesized rnRNA to a denaturing condition, and purifying the rnRNA from the impure preparation from step (a) by tangential flow filtration, wherein the mRNA purified from step (b) is substantially free of prematurely aborted RNA sequences and/or enzyme reagents used in in vitro synthesis.

23 Claims, 9 Drawing Sheets

Specification includes a Sequence Listing.

(56) References Cited

U.S. PATENT DOCUMENTS 4,662,382 A 5/1987 Sluetz et al.
4,701,162 A 10/1987 Rosenberg
4,710,169 A 12/1987 Christopher
4,720,517 A 1/1988 Ravichandran et al.
4,737,323 A 4/1988 Martin et al.
4,762,915 A 8/1988 Kung et al.
4,782,836 A 11/1988 Alt
4,843,155 A 6/1989 Chomczynski et al.
4,856,521 A 8/1989 Irnich
4,860,751 A 8/1989 Callaghan
4,878,908 A 11/1989 Martin et al.
4,892,540 A 1/1990 Vallana
4,897,355 A 1/1990 Eppstein et al.
4,920,016 A 4/1990 Allen et al.
4,946,683 A 8/1990 Forssen
4,946,857 A 8/1990 Kanehira et al.
4,960,409 A 10/1990 Catalano
4,966,945 A 10/1990 Drawert et al.
5,024,671 A 6/1991 Tu et al.
5,025,005 A 6/1991 Nomura et al.
5,043,430 A * 8/1991 Yoshikawa ............ C07K 14/61 435/69.7
5,047,540 A 9/1991 Kamata et al.
5,101,824 A 4/1992 Lekholm
5,104,399 A 4/1992 Lazarus
5,116,360 A 5/1992 Pinchuk et al.
5,138,067 A 8/1992 Kamata et al.
5,151,105 A 9/1992 Kwan-Gett
5,171,678 A 12/1992 Behr et al.
5,176,661 A 1/1993 Evard et al.
5,194,654 A 3/1993 Hostetler et al.
5,200,395 A 4/1993 Eto et al.
5,223,263 A 6/1993 Hostetler et al.
5,261,419 A 11/1993 Osypka
5,264,618 A 11/1993 Felgner et al.
5,279,833 A 1/1994 Rose
5,282,824 A 2/1994 Gianturco
5,284,491 A 2/1994 Sutton et al.
5,300,022 A 4/1994 Klapper et al.
5,314,430 A 5/1994 Bardy
5,330,768 A 7/1994 Park et al.
5,334,761 A 8/1994 Gebeyehu et al.
5,395,619 A 3/1995 Zalipsky et al.
5,405,363 A 4/1995 Kroll et al.
5,405,379 A 4/1995 Lane
5,455,352 A 10/1995 Huellmann et al.
5,464,924 A 11/1995 Silvis et al.
5,503,852 A 4/1996 Steiner et al.
5,528,023 A 6/1996 Butturini et al.
5,552,155 A 9/1996 Bailey et al.
5,595,756 A 1/1997 Bally et al.
5,607,385 A 3/1997 Francischelli et al.
5,609,624 A 3/1997 Kalis
5,610,283 A 3/1997 Buechler
5,614,548 A 3/1997 Piantadosi et al.
5,626,869 A 5/1997 Nyqvist et al.
5,631,018 A 5/1997 Zalipsky et al.
5,670,488 A 9/1997 Gregory et al.
5,677,124 A 10/1997 DuBois et al.
5,693,088 A 12/1997 Lazarus
5,697,953 A 12/1997 Kroll et al.
5,700,437 A 12/1997 Fujii et al.
5,705,188 A 1/1998 Junichi et al.
5,705,385 A 1/1998 Bally et al.
5,736,573 A 4/1998 Galat
5,744,335 A 4/1998 Wolff et al.
5,772,694 A 6/1998 Bokros et al.
5,776,165 A 7/1998 Ripart
5,776,747 A 7/1998 Schinstine et al.
5,783,383 A 7/1998 Kondo et al.
5,844,107 A 12/1998 Hanson et al.
5,874,105 A 2/1999 Watkins et al.
5,874,268 A 2/1999 Meyer et al.
5,885,613 A 3/1999 Holland et al.
5,910,168 A 6/1999 Myers et al.
5,916,208 A 6/1999 Luther et al.
5,965,434 A 10/1999 Wolff et al.
5,976,567 A 11/1999 Wheeler et al.
5,976,569 A 11/1999 Milstein
5,981,501 A 11/1999 Wheeler et al.
6,011,148 A 1/2000 Bussey et al.
6,055,454 A 4/2000 Heemels
6,067,471 A 5/2000 Warren
6,090,384 A 7/2000 Ra et al.
6,096,070 A 8/2000 Ragheb et al.
6,096,075 A 8/2000 Bokros et al.
6,120,799 A 9/2000 McDonald et al.
6,147,055 A 11/2000 Hobart et al.
6,152,955 A 11/2000 KenKnight et al.
6,165,763 A 12/2000 Brown et al.
6,169,923 B1 1/2001 Kroll
6,176,877 B1 1/2001 Buchanan et al.
6,180,778 B1 * 1/2001 Bastian ................ C12N 15/101 536/25.31
6,204,297 B1 3/2001 Tracy et al.
6,210,892 B1 4/2001 Bennett et al.
6,214,804 B1 4/2001 Felgner et al.
6,271,208 B1 8/2001 Bischoff
6,271,209 B1 8/2001 Smith et al.
6,287,591 B1 9/2001 Semple et al.
6,299,604 B1 10/2001 Ragheb et al.
6,335,199 B1 1/2002 Bischoff et al.
6,358,278 B1 3/2002 Brendzel et al.
6,370,434 B1 4/2002 Zhang et al.
6,371,983 B1 4/2002 Lane
6,417,326 B1 7/2002 Cullis et al.
6,485,726 B1 11/2002 Blumberg et al.
6,534,484 B1 3/2003 Wheeler et al.
6,585,410 B1 7/2003 Ryan
6,586,410 B1 7/2003 Wheeler et al.
6,670,178 B1 12/2003 Selden et al.
6,696,424 B1 2/2004 Wheeler
6,733,777 B2 5/2004 Erbacher et al.
6,743,823 B1 6/2004 Summar et al.
6,756,055 B2 6/2004 McDonald et al.
6,790,838 B2 9/2004 Alison et al.
6,815,432 B2 11/2004 Wheeler et al.
6,821,530 B2 11/2004 Koob et al.
6,835,395 B1 12/2004 Semple et al.
6,858,224 B2 2/2005 Wheeler et al.
6,858,225 B2 2/2005 Semple et al.
6,887,665 B2 5/2005 Trulson et al.
6,986,902 B1 1/2006 Chen et al.
6,998,115 B2 2/2006 Langer et al.
7,022,214 B2 4/2006 Olech
7,067,697 B2 6/2006 Gao
7,084,303 B2 8/2006 Watanabe et al.
7,341,738 B2 3/2008 Semple et al.
7,422,902 B1 9/2008 Wheeler et al.
7,427,394 B2 9/2008 Anderson et al.
7,507,859 B2 3/2009 Grinstaff et al.
7,556,684 B2 7/2009 Bury et al.
7,745,651 B2 6/2010 Heyes et al.
7,767,399 B2 8/2010 Murphy et al.
7,799,565 B2 9/2010 MacLachlan et al.
7,803,397 B2 9/2010 Heyes et al.
7,901,708 B2 3/2011 MacLachlan et al.
7,972,435 B2 7/2011 Bury et al.
8,021,686 B2 9/2011 Semple et al.
8,071,082 B2 12/2011 Zugates et al.
8,075,780 B2 12/2011 Pearce
8,101,741 B2 1/2012 MacLachlan et al.
8,106,022 B2 1/2012 Manoharan et al.
8,158,601 B2 4/2012 Chen et al.
8,188,263 B2 5/2012 MacLachlan et al.
RE43,612 E 8/2012 Anderson et al.
8,236,943 B2 8/2012 Lee et al.
8,278,036 B2 10/2012 Kariko et al.
8,287,849 B2 10/2012 Langer et al.
8,329,070 B2 12/2012 MacLachlan et al.
8,450,298 B2 5/2013 Mahon et al.
8,450,467 B2 5/2013 Manoharan et al.
8,470,585 B2 6/2013 de Vocht et al.
8,513,403 B2 8/2013 MacLachlan et al.

(56) References Cited

U.S. PATENT DOCUMENTS 8,557,231 B2 10/2013 Langer et al.
8,562,966 B2 10/2013 Zugates et al.
8,569,256 B2 10/2013 Heyes et al.
8,652,512 B2 2/2014 Schmehl et al.
8,691,966 B2 4/2014 Kariko et al.
8,710,200 B2 4/2014 Schrum et al.
8,748,089 B2 6/2014 Kariko et al.
8,802,644 B2 8/2014 Chen et al.
8,808,681 B2 8/2014 Anderson et al.
8,808,982 B2 8/2014 Dahl et al.
8,822,663 B2 9/2014 Schrum et al.
8,828,956 B2 9/2014 Manoharan et al.
8,835,108 B2 9/2014 Kariko et al.
8,846,348 B2 9/2014 Jendrisak et al.
8,853,377 B2 10/2014 Guild et al.
8,859,229 B2 10/2014 Rabinovich et al.
8,883,202 B2 11/2014 Manoharan et al.
8,936,942 B2 1/2015 Heyes et al.
8,969,353 B2 3/2015 Mahon et al.
8,980,864 B2 3/2015 Hoge et al.
8,999,351 B2 4/2015 Manoharan et al.
8,999,950 B2 4/2015 MacLachlan et al.
9,012,219 B2 4/2015 Kariko et al.
9,012,498 B2 4/2015 Manoharan et al.
9,018,187 B2 4/2015 Heyes et al.
9,051,567 B2 6/2015 Fitzgerald et al.
9,061,059 B2 6/2015 Chakraborty et al.
9,074,208 B2 7/2015 Maclachlan et al.
9,089,604 B2 7/2015 Chakraborty et al.
9,095,552 B2 8/2015 Chakraborty et al.
9,107,886 B2 8/2015 Chakraborty et al.
9,114,113 B2 8/2015 Chakraborty et al.
9,181,319 B2 11/2015 Schrum et al.
9,186,325 B2 11/2015 Manoharan et al.
9,186,372 B2 11/2015 de Fougerolles et al.
9,187,748 B2 11/2015 Geisbert et al.
9,192,651 B2 11/2015 Chakraborty et al.
9,220,755 B2 12/2015 Chakraborty et al.
9,220,792 B2 12/2015 Chakraborty et al.
9,233,141 B2 1/2016 Chakraborty et al.
9,254,311 B2 2/2016 Bancel et al.
9,295,689 B2 3/2016 de Fougerolles et al.
9,301,993 B2 4/2016 Chakraborty et al.
9,303,079 B2 4/2016 Chakraborty et al.
9,334,328 B2 5/2016 Schrum et al.
9,345,780 B2 5/2016 Manoharan et al.
9,352,042 B2 5/2016 Heyes et al.
9,352,048 B2 5/2016 Manoharan et al.
9,364,435 B2 6/2016 Yaworski et al.
9,394,234 B2 7/2016 Chen et al.
9,404,127 B2 8/2016 Yaworski et al.
9,428,751 B2 8/2016 MacDonald et al.
9,464,124 B2 10/2016 Bancel et al.
9,492,386 B2 11/2016 Maclachlan et al.
9,504,734 B2 11/2016 Bancel et al.
9,518,272 B2 12/2016 Yaworski et al.
9,580,734 B2 2/2017 Shankar et al.
9,597,413 B2 3/2017 Guild et al.
9,850,269 B2 * 12/2017 DeRosa ................. C07H 21/02
9,957,499 B2 * 5/2018 Heartlein ................ C12P 19/34
10,155,785 B2 * 12/2018 DeRosa ................... C07H 1/06
10,760,070 B2 * 9/2020 Funkner ................. G01N 30/02
10,808,241 B2 * 10/2020 Abysalh ............... C12Q 1/6806
10,876,104 B2 * 12/2020 Heartlein ................ A61P 43/00
11,059,841 B2 * 7/2021 DeRosa ................... C07H 1/06
11,692,189 B2 * 7/2023 DeRosa ................. C07H 21/02
536/25.4
11,820,977 B2 * 11/2023 DeRosa ................. C12N 15/10
12,234,446 B2 * 2/2025 Heartlein ........... C12N 15/1017
2001/0044412 A1 11/2001 Wolff et al.
2001/0047091 A1 11/2001 Miki et al.
2002/0022721 A1 2/2002 Trulson et al.
2002/0035246 A1 3/2002 Verschueren et al.
2002/0042136 A1 * 4/2002 Cannon .................. C12N 15/86
435/235.1
2002/0071834 A1 6/2002 Murray et al.
2002/0094528 A1 7/2002 Salafsky
2002/0192651 A1 12/2002 Wheeler et al.
2002/0192721 A1 12/2002 Rizzuto et al.
2002/0193622 A1 12/2002 Watanabe et al.
2003/0082154 A1 5/2003 Leamon
2003/0083272 A1 5/2003 Wiederholt et al.
2003/0104044 A1 6/2003 Semple et al.
2003/0181410 A1 9/2003 Wheeler et al.
2003/0186237 A1 10/2003 Ginsberg
2003/0215395 A1 11/2003 Yu et al.
2004/0076980 A1 4/2004 Charlton et al.
2004/0110709 A1 6/2004 Li et al.
2004/0132683 A1 7/2004 Felgner et al.
2004/0142025 A1 7/2004 Maclachlan et al.
2004/0224912 A1 11/2004 Dobie et al.
2004/0235982 A1 11/2004 Rabasco et al.
2005/0004058 A1 1/2005 Benoit et al.
2005/0008689 A1 1/2005 Semple et al.
2005/0032730 A1 2/2005 Von Der Mulbe et al.
2005/0054026 A1 3/2005 Atsushi et al.
2005/0059005 A1 3/2005 Tuschl et al.
2005/0059024 A1 3/2005 Conrad
2005/0059624 A1 3/2005 Hoerr et al.
2005/0065107 A1 3/2005 Hobart et al.
2005/0069590 A1 3/2005 Buehler et al.
2005/0079212 A1 4/2005 Wheeler et al.
2005/0112755 A1 5/2005 Pearce
2005/0143332 A1 6/2005 Monahan et al.
2005/0148786 A1 7/2005 Ikeda et al.
2005/0158302 A1 7/2005 Faustman et al.
2005/0226847 A1 10/2005 Coffin
2005/0244961 A1 11/2005 Short et al.
2005/0250723 A1 11/2005 Hoerr et al.
2006/0008910 A1 1/2006 MacLachlan et al.
2006/0051771 A1 3/2006 Murphy
2006/0059576 A1 3/2006 Pasinetti et al.
2006/0069225 A1 3/2006 Wintermantel et al.
2006/0083780 A1 4/2006 Heyes et al.
2006/0160759 A1 7/2006 Chen et al.
2006/0172003 A1 8/2006 Meers et al.
2006/0204566 A1 9/2006 Smyth-Templeton et al.
2006/0216343 A1 9/2006 Panzner et al.
2006/0223939 A1 10/2006 Lange et al.
2006/0228404 A1 10/2006 Anderson et al.
2006/0241071 A1 10/2006 Grinstaff et al.
2006/0246434 A1 11/2006 Erlander et al.
2007/0050070 A1 * 3/2007 Strain .................... G06Q 10/06
700/99
2007/0053879 A1 3/2007 Gregory et al.
2007/0135372 A1 6/2007 Maclachlan et al.
2007/0142628 A1 6/2007 Ghoshal et al.
2007/0172950 A1 7/2007 Wheeler et al.
2007/0252295 A1 11/2007 Panzner et al.
2007/0275923 A1 11/2007 Chen et al.
2007/0281336 A1 12/2007 Jendrisak et al.
2008/0113357 A1 5/2008 Baggio
2008/0145338 A1 6/2008 Anderson et al.
2008/0160048 A1 7/2008 Fuller
2008/0242626 A1 10/2008 Zugates et al.
2008/0248559 A1 10/2008 Inomata et al.
2008/0260706 A1 10/2008 Rabinovich et al.
2009/0023673 A1 1/2009 Manoharan et al.
2009/0093433 A1 4/2009 Woolf et al.
2009/0163705 A1 6/2009 Manoharan et al.
2009/0186805 A1 7/2009 Tabor et al.
2009/0221684 A1 9/2009 Grinstaff et al.
2009/0263407 A1 10/2009 Dande et al.
2009/0270481 A1 10/2009 MacLachlan et al.
2009/0286852 A1 * 11/2009 Kariko ............... A61K 48/0041
435/375
2009/0326051 A1 12/2009 Corey et al.
2010/0012012 A1 1/2010 Schaefbauer
2010/0028943 A1 2/2010 Thomas et al.
2010/0035249 A1 2/2010 Hayashizaki et al.
2010/0036084 A1 2/2010 Langer et al.
2010/0041152 A1 2/2010 Wheeler et al.
2010/0047261 A1 2/2010 Hoerr et al.
2010/0092572 A1 4/2010 Kaeuper et al.

(56) References Cited

U.S. PATENT DOCUMENTS

2010/0120129 A1 5/2010 Amshey et al.
2010/0178699 A1 7/2010 Gao et al.
2010/0189729 A1 7/2010 Hoerr et al.
2010/0267806 A1 10/2010 Bumcrot et al.
2010/0273220 A1 10/2010 Yanik et al.
2010/0331234 A1 12/2010 Mahon et al.
2011/0009641 A1 1/2011 Anderson et al.
2011/0038941 A1 2/2011 Lee et al.
2011/0092739 A1 4/2011 Chen et al.
2011/0143397 A1 6/2011 Kariko et al.
2011/0159550 A1 6/2011 Sanders
2011/0200582 A1 8/2011 Baryza et al.
2011/0236391 A1 9/2011 Mahler et al.
2011/0244026 A1 10/2011 Guild et al.
2011/0256175 A1 10/2011 Hope et al.
2011/0293703 A1 12/2011 Mahon et al.
2011/0311583 A1 12/2011 Manoharan et al.
2012/0007803 A1 1/2012 Takatsuka
2012/0009222 A1 1/2012 Nguyen et al.
2012/0060237 A1 3/2012 Wu et al.
2012/0065252 A1 3/2012 Schrum et al.
2012/0065358 A1 3/2012 Langer et al.
2012/0114831 A1 5/2012 Semple et al.
2012/0128760 A1 5/2012 Manoharan et al.
2012/0129910 A1 5/2012 Thompson et al.
2012/0142756 A1 6/2012 Guild et al.
2012/0174256 A1 7/2012 Kato et al.
2012/0195936 A1 8/2012 Rudolph et al.
2012/0202871 A1 8/2012 Heyes et al.
2012/0237975 A1 9/2012 Schrum et al.
2012/0251560 A1 10/2012 Dahlman et al.
2012/0251618 A1* 10/2012 Schrum .................. A61P 37/02
536/23.1
2012/0328668 A1 12/2012 Maclachlan et al.
2013/0004992 A1 1/2013 Lin et al.
2013/0017223 A1 1/2013 Hope et al.
2013/0158021 A1 6/2013 Dong et al.
2013/0195967 A1 8/2013 Guild et al.
2013/0224824 A1 8/2013 Shigemori et al.
2013/0237594 A1 9/2013 de Fougerolles et al.
2013/0259923 A1 10/2013 Bancel et al.
2013/0259924 A1 10/2013 Bancel et al.
2013/0266640 A1 10/2013 De Fougerolles et al.
2013/0302401 A1 11/2013 Ma et al.
2013/0337045 A1 12/2013 Bredehorst et al.
2013/0337528 A1 12/2013 Thompson et al.
2013/0337579 A1 12/2013 Lee et al.
2014/0010861 A1 1/2014 Bancel et al.
2014/0044772 A1 2/2014 MacLachlan et al.
2014/0093952 A1 4/2014 Serway
2014/0094399 A1 4/2014 Langer et al.
2014/0105964 A1 4/2014 Bancel et al.
2014/0105965 A1 4/2014 Bancel et al.
2014/0147432 A1 5/2014 Bancel et al.
2014/0147454 A1 5/2014 Chakraborty et al.
2014/0148502 A1 5/2014 Bancel et al.
2014/0155472 A1 6/2014 Bancel et al.
2014/0155473 A1 6/2014 Bancel et al.
2014/0155474 A1 6/2014 Bancel et al.
2014/0155475 A1 6/2014 Bancel et al.
2014/0161830 A1 6/2014 Anderson et al.
2014/0162897 A1 6/2014 Grunenwald et al.
2014/0171485 A1 6/2014 Bancel et al.
2014/0179756 A1 6/2014 Maclachlan et al.
2014/0179771 A1 6/2014 Bancel et al.
2014/0186432 A1 7/2014 Bancel et al.
2014/0193482 A1 7/2014 Bancel et al.
2014/0194494 A1 7/2014 Bancel et al.
2014/0199371 A1 7/2014 Bancel et al.
2014/0200163 A1 7/2014 Mikkelsen et al.
2014/0200261 A1 7/2014 Hoge et al.
2014/0200262 A1 7/2014 Bancel et al.
2014/0200263 A1 7/2014 Bancel et al.
2014/0200264 A1 7/2014 Bancel et al.
2014/0206752 A1 7/2014 Afeyan et al.
2014/0206753 A1 7/2014 Guild et al.
2014/0206755 A1 7/2014 Bancel et al.
2014/0206852 A1 7/2014 Hoge et al.
2014/0221248 A1 8/2014 Jendrisak et al.
2014/0221465 A1 8/2014 Bancel et al.
2014/0227300 A1 8/2014 Chin et al.
2014/0243399 A1 8/2014 Schrum et al.
2014/0249208 A1 9/2014 Bancel et al.
2014/0255467 A1 9/2014 Bancel et al.
2014/0255468 A1 9/2014 Bancel et al.
2014/0275227 A1 9/2014 Hoge et al.
2014/0275229 A1 9/2014 Bancel et al.
2014/0288160 A1 9/2014 Guild et al.
2014/0294937 A1 10/2014 MacLachlan et al.
2014/0294938 A1 10/2014 Guild et al.
2014/0294939 A1 10/2014 Guild et al.
2014/0294940 A1 10/2014 Guild et al.
2014/0329884 A1 11/2014 Dong et al.
2014/0343129 A1 11/2014 de Fougerolles et al.
2014/0363876 A1 12/2014 Jendrisak et al.
2015/0004217 A1 1/2015 Guild et al.
2015/0005372 A1 1/2015 Hoge et al.
2015/0011615 A1 1/2015 Manoharan et al.
2015/0011633 A1 1/2015 Shorr et al.
2015/0017211 A1 1/2015 de Fougerolles et al.
2015/0038556 A1 2/2015 Heartlein et al.
2015/0038558 A1 2/2015 Kariko et al.
2015/0044277 A1 2/2015 Bancel et al.
2015/0050354 A1 2/2015 Bouchon et al.
2015/0051268 A1 2/2015 Bancel et al.
2015/0056253 A1 2/2015 Bancel et al.
2015/0064235 A1 3/2015 Bancel et al.
2015/0064236 A1 3/2015 Bancel et al.
2015/0064242 A1 3/2015 Heyes et al.
2015/0064725 A1 3/2015 Schrum et al.
2015/0086614 A1 3/2015 Bancel et al.
2015/0110857 A1 4/2015 DeRosa et al.
2015/0110858 A1 4/2015 DeRosa et al.
2015/0110859 A1 4/2015 Heartlein et al.
2015/0111248 A1 4/2015 Bancel et al.
2015/0111945 A1 4/2015 Geisbert et al.
2015/0119444 A1 4/2015 Manoharan et al.
2015/0119445 A1 4/2015 Manoharan et al.
2015/0157565 A1 6/2015 Heartlein et al.
2015/0166465 A1 6/2015 Chen et al.
2015/0190515 A1 7/2015 Manoharan et al.
2015/0265708 A1 9/2015 Manoharan et al.
2015/0315541 A1 11/2015 Bancel et al.
2015/0315584 A1 11/2015 MacDonald et al.
2015/0366997 A1 12/2015 Guild et al.
2015/0376220 A1 12/2015 DeRosa et al.
2016/0024139 A1 1/2016 Berlanda Scorza et al.
2016/0095924 A1 4/2016 Hope et al.
2016/0114011 A1 4/2016 Bancel et al.
2016/0115477 A1 4/2016 Maclachlan et al.
2016/0115483 A1 4/2016 Maclachlan et al.
2016/0136236 A1 5/2016 Hoge et al.
2016/0151284 A1 6/2016 Heyes et al.
2016/0158385 A1 6/2016 Bancel et al.
2016/0193299 A1 7/2016 de Fougerolles et al.
2016/0194368 A1 7/2016 Hoge et al.
2016/0194625 A1 7/2016 Hoge et al.
2016/0199485 A1 7/2016 Manoharan et al.
2016/0213785 A1 7/2016 Manoharan et al.
2016/0237108 A1 8/2016 Fraley et al.
2016/0237134 A1 8/2016 Hoge et al.
2016/0250354 A1 9/2016 Manoharan et al.
2016/0251681 A1 9/2016 Yaworski et al.
2016/0256567 A1 9/2016 Heyes et al.
2016/0256568 A1 9/2016 Heyes et al.
2016/0256573 A1 9/2016 de Fougerolles et al.
2016/0264971 A1 9/2016 Geisbert et al.
2016/0264975 A1 9/2016 Schrum et al.
2016/0274089 A1 9/2016 Ciufolini et al.
2016/0304552 A1 10/2016 Roy et al.
2016/0317647 A1 11/2016 Ciaramella et al.
2016/0317676 A1 11/2016 Hope et al.
2016/0331828 A1 11/2016 Ciaramella et al.
2016/0348099 A1 12/2016 Roy et al.

(56) References Cited

U.S. PATENT DOCUMENTS

| | | | |
|---|---|---|---|
| 2016/0354490 | A1 | 12/2016 | Roy et al. |
| 2016/0354491 | A1 | 12/2016 | Roy et al. |
| 2016/0354492 | A1 | 12/2016 | Roy et al. |
| 2016/0354493 | A1 | 12/2016 | Roy et al. |
| 2016/0367687 | A1 | 12/2016 | Manoharan et al. |
| 2016/0367702 | A1 | 12/2016 | Hoge et al. |
| 2016/0375134 | A1 | 12/2016 | Bancel et al. |
| 2016/0375137 | A9 | 12/2016 | Manoharan et al. |
| 2017/0002060 | A1 | 1/2017 | Bolen et al. |
| 2017/0007702 | A1 | 1/2017 | Heyes et al. |
| 2017/0056528 | A1 | 3/2017 | De Fougerolles et al. |
| 2022/0162586 | A1 | 5/2022 | Geiger et al. |
| 2022/0348898 | A1 | 11/2022 | DeRosa et al. |

FOREIGN PATENT DOCUMENTS

| | | | |
|---|---|---|---|
| CN | 1399561 | | 2/2003 |
| CN | 100569877 | C | 12/2009 |
| CN | 101863544 | A | 10/2010 |
| DE | 24 30 998 | A1 | 1/1975 |
| DE | 2520814 | A1 | 11/1976 |
| DE | 3728917 | A1 | 3/1989 |
| EP | 6 73 637 | A1 | 9/1995 |
| EP | 0783297 | A1 | 7/1997 |
| EP | 0853123 | A1 | 7/1998 |
| EP | 0959092 | A1 | 11/1999 |
| EP | 1519714 | B1 | 4/2005 |
| EP | 1979364 | A2 | 10/2008 |
| EP | 2045251 | A1 | 4/2009 |
| EP | 2338478 | B1 | 6/2011 |
| EP | 2449106 | A1 | 5/2012 |
| EP | 2532649 | A1 | 12/2012 |
| EP | 2578685 | A2 | 4/2013 |
| EP | 2823809 | A1 | 1/2015 |
| EP | 3467108 | B1 | 5/2024 |
| FR | 1 378 382 | A | 11/1964 |
| FR | 2 235 112 | A1 | 1/1975 |
| GB | 1072118 | A | 6/1967 |
| GB | 1602085 | A | 11/1981 |
| JP | H07-053535 | | 2/1955 |
| JP | S48-022365 | | 3/1973 |
| JP | S49-127908 | A | 12/1974 |
| JP | S51-023537 | | 2/1976 |
| JP | 51-125144 | | 11/1976 |
| JP | S52-010847 | | 1/1977 |
| JP | S63125144 | A | 5/1988 |
| JP | 63-154788 | | 6/1988 |
| JP | H09-505593 | A | 6/1997 |
| JP | H10-197978 | A | 7/1998 |
| JP | 11-005786 | A | 1/1999 |
| JP | 11-080142 | | 3/1999 |
| JP | 2001-523215 | A | 11/2001 |
| JP | 2002-167368 | A | 6/2002 |
| JP | 2003-519199 | A | 6/2003 |
| JP | 4-108173 | B2 | 6/2008 |
| JP | 2008-247749 | A | 10/2008 |
| JP | 2010053108 | A | 3/2010 |
| JP | 50-24216 | B2 | 9/2012 |
| JP | 6586075 | B2 | 10/2019 |
| WO | WO-1992/004970 | A1 | 4/1992 |
| WO | WO-93/18229 | A1 | 9/1993 |
| WO | WO-93/18754 | A1 | 9/1993 |
| WO | WO-95/11004 | A1 | 4/1995 |
| WO | WO-95/14651 | A1 | 6/1995 |
| WO | WO-95/27478 | A1 | 10/1995 |
| WO | WO-96/18372 | A2 | 6/1996 |
| WO | WO-96/26179 | A1 | 8/1996 |
| WO | WO-96/37211 | A1 | 11/1996 |
| WO | WO-96/40964 | A2 | 12/1996 |
| WO | WO-97/46223 | A1 | 12/1997 |
| WO | WO 98/05673 | A1 | 2/1998 |
| WO | WO-1998/005673 | A1 | 2/1998 |
| WO | WO-98/10748 | A1 | 3/1998 |
| WO | WO-98/16202 | A2 | 4/1998 |
| WO | WO 98/30685 | A2 | 7/1998 |
| WO | WO-1998/030685 | A2 | 7/1998 |
| WO | WO-98/51278 | A2 | 11/1998 |
| WO | WO-00/03044 | A1 | 1/2000 |
| WO | WO-00/62813 | A2 | 10/2000 |
| WO | WO-00/64484 | A2 | 11/2000 |
| WO | WO-00/69913 | A1 | 11/2000 |
| WO | WO-01/05375 | A1 | 1/2001 |
| WO | WO 01/07599 | A1 | 2/2001 |
| WO | WO-02/22709 | A1 | 3/2002 |
| WO | WO-02/31025 | A2 | 4/2002 |
| WO | WO-02/34236 | A2 | 5/2002 |
| WO | WO-02/42317 | A2 | 5/2002 |
| WO | WO 02/053582 | A2 | 7/2002 |
| WO | WO 2003/033739 | | 4/2003 |
| WO | WO-03/040288 | A2 | 5/2003 |
| WO | WO-03/070735 | A2 | 8/2003 |
| WO | WO-2004/043588 | A2 | 5/2004 |
| WO | WO-2004/048345 | A2 | 6/2004 |
| WO | WO 2004/076695 | A1 | 9/2004 |
| WO | WO-2004/106411 | A2 | 12/2004 |
| WO | WO-2005/026372 | A1 | 3/2005 |
| WO | WO-2005/028619 | A2 | 3/2005 |
| WO | WO-2005/037226 | A2 | 4/2005 |
| WO | WO 2005/058933 | | 6/2005 |
| WO | WO-2005/121348 | A1 | 12/2005 |
| WO | WO-2006/000448 | A2 | 1/2006 |
| WO | WO-2006/016097 | A2 | 2/2006 |
| WO | WO-2006/082088 | A1 | 8/2006 |
| WO | WO-2006/105043 | A2 | 10/2006 |
| WO | WO-2006/138380 | A2 | 12/2006 |
| WO | WO-2007/024708 | A2 | 3/2007 |
| WO | WO-2007/031091 | A2 | 3/2007 |
| WO | WO-2007/120863 | A2 | 10/2007 |
| WO | WO-2007/126386 | A1 | 11/2007 |
| WO | WO-2007/143659 | A2 | 12/2007 |
| WO | WO-2008/011561 | A2 | 1/2008 |
| WO | WO-2008/042973 | A2 | 4/2008 |
| WO | WO-2008/083949 | A2 | 7/2008 |
| WO | WO-2008/113364 | A2 | 9/2008 |
| WO | WO-2009/046220 | A2 | 4/2009 |
| WO | WO 2009/093142 | | 7/2009 |
| WO | WO-2009/127060 | A1 | 10/2009 |
| WO | WO-2009/127230 | A1 | 10/2009 |
| WO | WO 2010/053108 | | 3/2010 |
| WO | WO 2010/037408 | A2 | 4/2010 |
| WO | WO-2010/042877 | A1 | 4/2010 |
| WO | WO-2010/045512 | A2 | 4/2010 |
| WO | WO-2010/053572 | A2 | 5/2010 |
| WO | WO-2010/054401 | A1 | 5/2010 |
| WO | WO-2010/054405 | A1 | 5/2010 |
| WO | WO-2010/056403 | A1 | 5/2010 |
| WO | WO-2010/099387 | A1 | 9/2010 |
| WO | WO-2010/114789 | A1 | 10/2010 |
| WO | WO-2010/119256 | A1 | 10/2010 |
| WO | WO-2010/129709 | A1 | 11/2010 |
| WO | WO-2010/144740 | A1 | 12/2010 |
| WO | WO-2010/147992 | A1 | 12/2010 |
| WO | WO-2010/148013 | A2 | 12/2010 |
| WO | WO-2011/012746 | A2 | 2/2011 |
| WO | WO-2011/039144 | A1 | 4/2011 |
| WO | WO-2011/068810 | A1 | 6/2011 |
| WO | WO-2011/075656 | A1 | 6/2011 |
| WO | WO-2011/141705 | A1 | 11/2011 |
| WO | WO-2012/019168 | A2 | 2/2012 |
| WO | WO-2012/019630 | A1 | 2/2012 |
| WO | WO-2012/019780 | A1 | 2/2012 |
| WO | WO-2012/027675 | A2 | 3/2012 |
| WO | WO-2012/045075 | A1 | 4/2012 |
| WO | WO-2012/045082 | A2 | 4/2012 |
| WO | WO-2012/075040 | A2 | 6/2012 |
| WO | WO 2012/077080 | A1 | 6/2012 |
| WO | WO-2012/133737 | A1 | 10/2012 |
| WO | WO-2012/135025 | A2 | 10/2012 |
| WO | WO 2012/135805 | A2 | 10/2012 |
| WO | WO-2012/170889 | A1 | 12/2012 |
| WO | WO-2012/170930 | A1 | 12/2012 |
| WO | WO-2013/039857 | A1 | 3/2013 |
| WO | WO-2013/039861 | A2 | 3/2013 |
| WO | WO-2013/063468 | A1 | 5/2013 |

(56) References Cited

FOREIGN PATENT DOCUMENTS

WO WO-2013/090186 A1 6/2013
WO WO-2013/101690 A1 7/2013
WO WO-2013/102203 A1 7/2013
WO WO-2013/126803 A1 8/2013
WO WO-2013/130161 A1 9/2013
WO WO-2013/149140 A1 10/2013
WO WO-2013/149141 A1 10/2013
WO WO-2013/151663 A1 10/2013
WO WO-2013/151664 A1 10/2013
WO WO-2013/151666 A2 10/2013
WO WO-2013/151667 A1 10/2013
WO WO-2013/151668 A2 10/2013
WO WO-2013/151670 A2 10/2013
WO WO-2013/151671 A1 10/2013
WO WO-2013/151672 A2 10/2013
WO WO-2013/151736 A2 10/2013
WO WO-2013/185067 A1 12/2013
WO WO-2013/185069 A1 12/2013
WO WO-2014/028487 A1 2/2014
WO WO-2014/089486 A1 6/2014
WO WO 2014/107571 A1 7/2014
WO WO-2014/113089 A2 7/2014
WO WO 2014/140211 A1 9/2014
WO WO-2014/144039 A1 9/2014
WO WO-2014/144196 A1 9/2014
WO WO-2014/144711 A1 9/2014
WO WO-2014/144767 A1 9/2014
WO WO-2014/152027 A1 9/2014
WO WO-2014/152030 A1 9/2014
WO WO-2014/152031 A1 9/2014
WO WO-2014/152211 A1 9/2014
WO WO-2014/152513 A1 9/2014
WO WO-2014/152540 A1 9/2014
WO WO-2014/152659 A1 9/2014
WO WO-2014/152673 A1 9/2014
WO WO-2014/152774 A1 9/2014
WO WO-2014/152940 A1 9/2014
WO WO 2014/152966 A1 9/2014
WO WO-2014/153052 A2 9/2014
WO WO-2014/158795 A1 10/2014
WO WO-2014/159813 A1 10/2014
WO WO-2014/179562 A1 11/2014
WO WO-2014/210356 A1 12/2014
WO WO-2015/006747 A2 1/2015
WO WO-2015/011633 A1 1/2015
WO WO-2015/048744 A2 4/2015
WO WO-2015/051169 A2 4/2015
WO WO-2015/051173 A2 4/2015
WO WO-2015/058069 A1 4/2015
WO WO-2015/085318 A2 6/2015
WO WO-2015/089511 A2 6/2015
WO WO-2016/054421 A1 4/2016
WO WO-2016/071857 A1 5/2016
WO WO-2016/077123 A1 5/2016
WO WO-2016/077125 A1 5/2016
WO WO-2016/118724 A1 7/2016
WO WO-2016/118725 A1 7/2016
WO WO-2016/154127 A2 9/2016
WO WO-2016/164762 A1 10/2016
WO WO-2016/183366 A2 11/2016
WO WO-2016/193206 A1 12/2016
WO WO-2016/197132 A1 12/2016
WO WO-2016/197133 A1 12/2016
WO WO-2016/201377 A1 12/2016
WO WO-2017/149139 A1 9/2017
WO WO 2022/266389 A1 12/2022

OTHER PUBLICATIONS

Leberton et al., Biotechnology and Bioengineering110(5) :964 (Year: 2008).*

Krieg et al., Nucleic Acids Research 12(18) :7057 (Year: 1984).*

Linpinsel and Cohn, General Protocols for Preparation of Plasmid DNA Template, RNA In Vitro Transcription, and RNA Purification by Denaturing PAGE. Methods in Molecular Biology 941 : 43 (Year: 2012).*

Moon et al., In vitro Transcription of modified RNAs. Methods in Molecular Biology 941 : 43 (Year: 2012).*

Nielsen et al. Scale-up bioprocesses. Ch. 11 in Bioreaction Engineering Principles (Year: 203).*

Sahin et al.mRNA- based therapeutics—developing a new class of drugs Nature Reviews Drug Discovery (Year: 2014).*

Pokrovskaya et al. In vitro Transcription :Preparative RNA yields in analytical scale reactions. Analytical Biochemisty 220:420-423 (Year: 1994).*

Krieg and Melton. Nucleic Acids Research 12(18) : 7057 (Year: 1994).*

Weide et al., Results of the First Phase I/II Clinical Vaccination Trial With Direct Injection of mRNA. Journal of Immunology 31(2) :180-188 (Year: 2008).*

U.S. Appl. No. 60/083,294, filed Apr. 28, 1998, Chen et al.

U.S. Appl. No. 61/494,714, filed Jun. 8, 2011, Guild et al.

U.S. Appl. No. 61/494,745, filed Jun. 8, 2011, Guild et al.

U.S. Appl. No. 61/494,881, filed Jun. 8, 2011, Guild et al.

U.S. Appl. No. 61/494,882, filed Jun. 8, 2011, Zhang et al.

Adami, R.C. et al., An amino acid-based amphoteric liposomal delivery system for systemic administration of siRNA. Molecular Therapy 19(6):1141-1151 (2011).

Akinc, A. et al., A combinatorial library of lipid-like materials for delivery of RNAi therapeutics. Nature Biotechnology 26(5):561-569 (2008).

Akinc, A. et al., Development of lipidoid-siRNA formulations for systemic delivery to the liver. Molecular Therapy 17(5):872-879 (2009).

Alton, E.W.F.W. et al., Cationic Lipid-Mediated CFTR Gene Transfer to the Lungs and Nose of Patients with Cystic Fibrosis: a Double-Blind Placebo-Controlled Trial, Lancet, 353:947-954 (1999).

Anderson, D.G. et al., Structure/property studies of polymeric gene delivery using a library of poly(beta-amino esters). Molecular Therapy 11(3):426-434 (2005).

Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202 (2003).

Anderson, J. Biological Responses to Materials. Annual Review of Materials Research 31:81-110 (2001).

Anderson, W. French, Human gene therapy, Nature, 392, 25-30 (1998).

Andries, O. et al., Comparison of the Gene Transfer Efficiency of mRNA/GL67 and pDNA/GL67 Complexes in Respiratory Cells, Mol. Pharmaceut., 9: 2136-2145 (2012).

Auffray, C. et al., Purification of Mouse Immunoglubulin Heavy-Chain Messenger RNAs from Total Myeloma Tumor RNA, European Journal of Biochemistry, 107(2):303-314 (1980).

Author Unknown, Blood Proteins, published by Wikipedia, San Francisco, CA, 2 pages, <http://en.wikipedia.org/wiki/Biood_proteins> downloaded May 17, 2015.

Bahlke, M. A. et al., Progress towards in vivo use of siRNAs, Molecular Therapy, 13:644-670 (2006).

Bajaj, A. et al., Synthesis and gene transfection efficacies of PEI-cholesterol-based lipopolymers. Bioconjugate Chemistry 19(8):1640-516511 (2008).

Barreau, C. et al., Liposome-mediated RNA transfection should be used with caution, RNA, 12:1790-1793 (2006).

Behr, J. et al., Efficient Gene Transfer into Mammalian Primary Endocrine Cells with Lipo Polyamine-Coated DNA, Proc. Nat.'l Acad. Sci., 86: 6982-6986 (1989).

Bennett, J. Immune response following intraocular delivery of recombinant viral vectors, Gene Therapy, 10: 977-982 (2003).

Bloomfield, V.A., Quasi-Elastic Light Scattering Applications in Biochemistry and Biology, Ann. Rev. Biophys. Bioeng. 10:421-450 (1981).

Boussif, O. et al., A versatile vector for gene and oligonucleotide transfer into cells in culture and in vivo: polyethylenimine. Proceedings of the National Academy of Sciences of the USA. 92(16):7297-7301 (1995).

(56) References Cited

OTHER PUBLICATIONS

Braun, C.S. et al., Structure/function relationships of polyamidoamine/DNA dendrimers as gene delivery vehicles. Journal of Pharmaceutical Sciences 94(2):423-436 (2005).
Breunig, M. et al., Breaking up the correlation between efficacy and toxicity for nonviral gene delivery. Proceedings of the National Academy of Sciences of the U S A. 104(36):14454-14459 (2007).
Breunig, M. et al., Mechanistic investigation of poly(ethylene imine)-based siRNA delivery: disulfide bonds boost intracellular release of the cargo. Journal of Controlled Release 130(1):57-63 (2008).
Brey, D.M. et al., Controlling poly(beta-amino ester) network properties through macromer branching. Acta Biomaterialia 4(2):207-217 (2008).
Brey, D.M. et al., Influence of macromer molecular weight and chemistry on poly(beta-amino ester) network properties and initial cell interactions. Journal of Biomedical Materials Research Part A 85(3):731-741 (2007).
Budker, V. et al., Protein/Amphipathic Polyamine Complexes Enable Highly Efficient Transfection with Minimal Toxicity, BioTechniques, 23: 139-147 (1997).
Burnett, J.C. et al., Current progress of siRNA/shRNA therapeutics in clinical trials. Biotechnology Journal 6(9):1130-1146 (2011).
Byk, G. et al., Synthesis, activity, and structure—activity relationship studies of novel cationic lipids for DNA transfer. Journal of Medical Chemistry 41(2):224-235 (1998).
Caplen, N.J. et al., In vitro liposome-mediated DNA transfection of epithelial cell lines using the cationic liposome DC-Chol/DOPE, Gene Therapy, 2:603-613 (1995).
Cassiman, D. Gene transfer for inborn errors of metabolism of the liver: the clinical perspective, Current Pharmaceutical Design, 17(24):2550-2557 (2011).
Castanotto, D. et al., The promises and pitfalls of RNA-interference-based therapeutics. Nature 457(7228):426-433 (2009).
Chakraborty, C. Potentiality of Small Interfering RNAs (siRNA) as Recent Therapeutic Targets for Gene-Silencing. Current Drug Targets 8(3):469-82 (2007).
Chandler, R. et al., Liver-directed adeno-associated virus serotype 8 gene transfer rescues a lethal murine model of citrullinemmia type 1, Gene Therapy, 20:1188-1191 (2013).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).
Chiou, H.C. et al., Enhanced resistance to nuclease degradation of nucleic acids complexed to; asialoglycoprotein-polylysine carriers, Nucleic Acids Research, 22(24):5439-5446 (1994).
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Conese, M. et al., Gene and Cell Therapy for Cystic Fibrosis: From Bench to Bedside, J. Cyst. Fibros., 10 Suppl 2:S114-s128 (2011).
Cotten, M. et al., Receptor-mediated transport of DNA into eukaryotic cells. Methods in Enzymology 217 (H):618-644 (1993).
Cowling, V.H., Regulation of mRNA cap methylation, Biochemical Journal, 425:295-302 (2010).
Creusat, G. et al., Proton sponge trick for pH-sensitive disassembly of polyethylenimine-based siRNA delivery systems. Bioconjugate Chemistry 21(5):994-1002 (2010).
Crooke, S.T. Molecular mechanisms of action of antisense drugs. Biochimica et Biophysica Acta 1489(1):31-44. Review (1999).
Crystal, R.G. Transfer of genes to humans: early lessons and obstacles to success. Science 270(5235):404-410. Review (1995).
Damen, M. et al., Delivery of DNA and siRNA by novel gemini-like amphiphilic peptides. Journal of Controlled Release 145(1):33-39 (2010).
Dande, P. et al., Improving RNA interference in mammalian cells by 4'-thio-modified small interfering RNA (siRNA): effect on siRNA activity and nuclease stability when used in combination with 2'-0-alkyl modifications, Journal of Medicinal Chemistry, 49(5):1624-1634 (2006).
Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Debus, H. et al., Delivery of Messenger RNA Using Poly(ethylene imine)-poly(ethylene glycol)-Copolymer Blends for Polyplex Formation: Biophysical Characterization and In Vitro Transfection Properties, J. Control. Rel., 148:334-343 (2010).
Decher, G. Fuzzy Nanoassemblies: Toward Layered Polymeric Multicomposites. Science 277: 1232-1237 (1997).
Demeshkina, N. et al., Interactions of the ribosome with mRNA and tRNA, Current Opinion in Structural Biology, 20(3):325-332 (2010).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N",N"'-Tetraacetic Acid (DOTA)-Peptide versus 2IT-DOTA Monoclonal Antibody Linkage for RIT1, Clin. Cancer Res., 9: 3665s (2003).
Dern, R.J. et al., Toxicity studies of pyrimethamine (daraprim). The American Journal of Tropical Medicine and Hygiene 4(2):217-220 (1955).
Deshmukh, H. M and Huang, L., Liposome and polylysine mediated gene therapy. New Journal of Chemistry 21:113-124 (1997).
Discher, B.M. et al., Polymersomes: tough vesicles made from diblock copolymers. Science 284(5417):1143-1146 (1999).
Discher, D.E. and Eisenberg, A., Polymer vesicles. Science 297(5583):967-973. Review (2002).
Dong, Y. et al., Lipopeptide nanoparticles for potent and selective siRNA delivery in rodents and nonhuman primates, Proceedings of the National Academy of Sciences, 111(11): 3955-3960 (2014).
Drummond, D.C. et al., Optimizing Liposomes for Delivery of Chemotherapeutic Agents to Solid Tumors, Pharmacological Reviews, 51(4): 691-743 (1999).
Dwarki, V. et al., Cationic liposome-mediated RNA transfection, Methods in Enzymology, 217:644-654 (1993).
Elbashir, S.M. et al., RNA interference is mediated by 21- and 22-nucleotide RNAs. Genes & Development 15: 188-200 (2001).
Elton, C., The Next Next Big Thing, Boston Magazine, 106-118 (Mar. 2013).
Emlen, W. et al., Effect of DNA size and strandedness on the in vivo clearance and organ localization of DNA, Clinical & Experimental Immunology, 56:185-192 (1984).
Eon-Duval, A. et al., Removal of RNA impurities by tangential flow filtration in an RNase-free plasmid DNA purification process, Analytical Biochemistry, 316(1):66-73 (2003).
Ernst, N. et al., Interaction of Liposomal and Polycationic Transfection Complexes with Pulmonary Surfactant, J. Gene. Med., 1:331-340 (1999).
Estimated Number of Animal and Plant Species on Earth, http://www.factmonster.com/ipka/A0934288.html, 2000-2014, 3 pages, (Retrieved Aug. 2, 2014).
Ewert, K. et al., Cationic lipid-DNA complexes for gene therapy: understanding the relationship between complex structure and gene delivery pathways at the molecular level. Current Medicinal Chemistry 11(2): 133-149 (2004).
Fath, S. et al., Multiparameter RNA and Codon Optimization: a Standardized Tool to Assess and Enhance Autologous Mammalian Gene Expression, PLoS One, 6(3):e17596 (14 pages) 2011.
Fechter, P. and Brownlee, G. G., Recognition of mRNA cap structures by viral and cellular proteins, Journal of General Virology, 86:1239-1249 (2005).
Felgner, P.L. and Ringold, G.M., Cationic liposome-mediated transfection, Nature, 337(6205):387-388 (1989).

(56) References Cited

OTHER PUBLICATIONS

Felgner, P.L. et al., Lipofection: a Highly Efficient, Lipid-Mediated DNA-Transfection Procedure, Proc. Natl. Acad., 84:7413-7417 (1987).
Fenske, D.B. and Cullis, P., Liposomal nanomedicines. Expert Opinion on Drug Delivery 5(1):25-44 (2008).
Fernandez, V. et al., Cross Flow Filtration of RNA Extracts by Hollow Fiber Membrane, Acta Biotechnologica, 12(1):49-56 (1992).
Ferruti, P.F. and Barbucci, R. , Linear amino polymers: Synthesis, protonation and complex formation. Advances in Polymer Science 58:55-92 (1984).
Ferruti, P.F. et al., A novel modification of poly(l-lysine) leading to a soluble cationic polymer with reduced toxicity and with potential as a transfection agent. Macromolecular Chemistry and Physics 199:2565-2575 (1998).
Fire, A. et al., Potent and specific genetic interference by double-stranded RNA in Caenorhabditis elegans. Nature 391(6669):806-811 (1998).
Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-992 (2004).
Fumoto, S. et al., Targeted Gene Delivery: Importance of Administration Routes, Novel Gene Therapy Approaches, 3-31 (2013).
Furgeson, D.Y. et al., Modified linear polyethylenimine-cholesterol conjugates for DNA complexation. Bioconjugate Chemistry 14(4):840-847 (2003).
Furgeson, D.Y. et al., Novel water insoluble lipoparticulates for gene delivery. Pharmaceutical Research 19(4): 382-390 (2002).
Galipon, J. et al., Stress-induced lncRNAs evade nuclear degradation and enter the translational machinery, Genes to Cells, 18(5):353-368 (2013).
Gao, X. and Huang, L., A novel cationic liposome reagent for efficient transfection of mammalian cells, Biochem. Biophys. Res. Comm., 179(1): 280-285 (1991).
Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).
Geraerts, M. et al., Upscaling of lentiviral vector production by tangential flow filtration, Journal of Gene Medicine, 7(10):1299-1310 (2005).
Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6):1068-1074 (1999).
Gonzalez-Aseguinolaza, G. et al., Gene therapy of liver diseases: a 2011 perspective, Clinics and Research in Hepatology and Gastroenterology, 35(11):699-708 (2011).
Gordon, N. Ornithine transcarbamylase deficiency: a urea cycle defect, European Journal of Paediatric Neurology, 7:115-121 (2003).
Grayson, A.C.R. et al., Biophysical and structural characterization of polyethylenimine-mediated siRNA delivery in vitro. Pharmaceutical Research 23(8): 1868-1876 (2006).
Grudzien, E. et al., Novel cap analogs for in vitro synthesis of mRNAs with high translational efficiency, RNA Biology, 10(9):1479-1487 (2004).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).
Guttman, M. et al., Chromatin signature reveals over a thousand highly conserved large non-coding RNAs in mammals, Nature, 458:223-227 (2009).
Haensler, J. and Szoka, F., Polyamidoamine cascade polymers mediate efficient transfection of cells in culture. Bioconjugate Chemistry 4(5):372-379 (1993).
Harada-Shiba, M. et al., Polyion complex micelles as vectors in gene therapy—pharmacokinetics and in vivo; gene transfer, Gene Therapy, 9(6):407-414 (2002).
Haskins M., Gene Therapy for Lysosomal Storage Disorders (LDSs) in Large Animal Models, ILAR J., 50(2):112-121 (2009).
Hata, A. et al., Isolation and Characterization of the Human Ornithine Transcarbamylase Gene: Structure of the 5'-End Region, Journal of Biochemistry, 100:717-725 (1986).
Hecker, J. et al., Advances in Self-Limited Gene Expression of Protective Intracellular Proteins In-Vivo in Rat Brain Using mRNA / Cationic Lipid Complexes, Anesthesia and Analgesia, 86(2S):346S (1994).
Heidenreich, O. et al., High Activity and Stability of Hammerhead Ribozymes Containing 2'-Modified Pyrimidine Nucleosides and Phosphorothioates, the Journal of Biological Chemistry, 269(3):2131-2138 (1994).
Henkin, R. I. et al., Inhaled Insulin-Intrapulmonary, intranasal, and other routes of administration: Mechanisms of action, Nutrition, 26: 33-39 (2010).
Hess, P. R. et al., Vaccination with mRNAs Encoding Tumor-Associated Antigens and Granulocyte-Macrophage Colony-Stimulating Factor Efficiently Primes CTL Responses, but is Insufficient to Overcome Tolerance to a Model Tumor/Self Antigen, Cancer Immunology, Immunotherapy:CII, 55(6): 672-683 (2006).
Heyes, J. et al., Cationic Lipid Saturation Influences Intracellular Delivery of Encapsulated Nucleic Acids, J. Controlled Release, 107:276-287 (2005).
Higman, M.A. et al., The mRNA (Guanine-7-)methyltransferase Domain of the Vaccinia Virus mRNA Capping Enzyme, the Journal of Biological Chemistry, 269(21):14974-14981 (1994).
Hill, I.R.C. et al., In vitro cytotoxicity of poly(amidoamine)s: relevance to DNA delivery. Biochimica et Biophysica Acta 1427: 161-174 (1999).
Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).
Hillery, A.M. et al., Drug Delivery and Targeting for Pharmacists and Pharmaceutical Scientists, Taylor and Francis (2005).
Hoerr, I. et al., In Vivo Application of RNA Leads to Induction of Specific Cytotoxic T Lymphocytes and Antibodies, European Journal of Immunology, 30(1):1-7 (2000).
Hofland, H.E.J et al., Formation of stable cationic lipid/DNA complexes for gene transfer. Proceedings of the National Academy of Sciences of the USA 93 (14): 7305-7309 (1996).
*Homo sapiens* galactosidase, alpha (GLA) mRNA, NCBI Reference Sequence NM_000169.1, Modification Date: Nov. 17, 2006.
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hope, M.J. et al., Reduction of Liposome Size and Preparation of Unilamellar Vesicles by Extrusion Techniques, in: Liposome Technology, 1:123-139 (1993).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Horwich, A.L. et al., Structure and Expression of a Complementary DNA for the Nuclear Coded Precursor of Human Mitochondrial Ornithine Transcarbamylase, Science, 224(4653):1068-1074 (1984).
Horwich, A.L. et al., Targeting of Pre-Ornithine Transcarbamylase to Mitochondria: Definition of Critical Regions and Residues in the Leader Peptide, Cell, 44:451-459 (1986).
Howard, K.A. Delivery of RNA interference therapeutics using polycation-based nanoparticles. Advanced Drug Delivery Reviews 61: 710-720 (2009).
Huang, Z. et al., Thiocholesterol-Based Lipids for Ordered Assembly of Bioresponsive Gene Carriers, Molecular Therapy, 11(3):409-417 (2005).
Huttenhofer, A. and Noller, H., Footprinting mRNA-ribosome complexes with chemical probes, the EMBO Journal, 13(16):3892-3901 (1994).

(56) References Cited

OTHER PUBLICATIONS

Incani, V. et al., Lipid and hydrophobic modification of cationic carriers on route to superior gene vectors. Soft Matter 6: 2124-2138 (2010).
International Preliminary Report on Patentability for PCT/US2010/058457, 12 pages (Jun. 14, 2012).
International Search Report for PCT/US2010/058457, 4 pages (May 6, 2011).
International Search Report for PCT/US2011/062459, 3 pages (Apr. 11, 2012).
International Search Report for PCT/US2012/041663, 4 pages (Oct. 8, 2012).
International Search Report for PCT/US2012/041724, 5 pages (Oct. 25, 2012).
International Search Report for PCT/US2013/034602, 2 pages (Jun. 17, 2013).
International Search Report for PCT/US2013/034604, 4 pages (Jun. 17, 2013).
International Search Report for PCT/US2013/044769, 4 pages (Nov. 12, 2013).
International Search Report for PCT/US2013/044771, 6 pages (Nov. 1, 2013).
International Search Report for PCT/US2013/073672, 6 pages (Mar. 3, 2014).
International Search Report for PCT/US2014/027422, 5 pages (Jul. 31, 2014).
International Search Report for PCT/US2014/027585, 3 pages (Jul. 14, 2014).
International Search Report for PCT/US2014/027602, 6 pages (Jul. 28, 2014).
International Search Report for PCT/US2014/027717, 5 pages (Jul. 16, 2014).
International Search Report for PCT/US2014/028330, 5 pages (Jul. 22, 2014).
International Search Report for PCT/US2014/028441, 6 pages (Jul. 22, 2014).
International Search Report for PCT/US2014/028498, 5 pages (Jul. 28, 2014).
International Search Report for PCT/US2014/061786, 6 pages (Feb. 6, 2015).
International Search Report for PCT/US2014/061793, 4 pages (Feb. 6, 2015).
International Search Report for PCT/US2014/061830, 5 pages (Feb. 4, 2015).
International Search Report for PCT/US2014/061841, 6 pages (Feb. 24, 2015).
International Search Report for PCT/US2015/21403 (4 pages) mailed Jun. 15, 2015.
Jakobsen, K. et al., Purification of MRNA Directly From Crude Plant Tissues in 15 Minutes Using Magnetic Oligo DT Microsheres, Nucleic Acids Research, 18(12):3669 (1990).
Jeffs, L.B. et al., A scalable, extrusion-free method for efficient liposomal encapsulation of plasmid DNA, Pharmacol. Res., 22(3): 362-372 (2005).
Jiang, G. et al., Hyaluronic acid-polyethyleneimine conjugate for target specific intracellular delivery of siRNA. Biopolymers 89 (7): 635-642 (2008).
Jiang, M. et al., Electrochemically controlled release of lipid/DNA complexes: a new tool for synthetic gene delivery system. Electrochemistry Communications (6): 576-582 (2004).
Jiang, S. and Cao, Z., Ultralow-fouling, functionalizable, and hydrolyzable zwitterionic materials and their derivatives for biological applications. Advanced Materials 22(9):920-932 (2010).
Jolck, R.I. et al., Solid-phase synthesis of PEGylated lipopeptides using click chemistry. Bioconjugate Chemistry 21(5):807-810 (2010).
Jon, S. et al., Degradable poly(amino alcohol esters) as potential DNA vectors with low cytotoxicity. Biomacromolecules 4(6):1759-1762 (2003).
Jones, G. et al., Duplex- and Triplex-Forming Properties of 4'-Thio-Modified Oligodeoxynucleotides, Bioorganic & Medicinal Chemistry Letters, 7(10):1275-1278 (1997).
Kabanov, A.V. and Kabanov, V.A., DNA complexes with polycations for the delivery of genetic material into cells. Bioconjugate Chemistry 6(1): 7-20 (1995).
Kamath, S. et al., Surface chemistry influences implant-mediated host tissue responses. Journal of Biomedical Materials Research A 86(3):617-626 (2007).
Kariko, K. et al., In vivo protein expression from mRNA delivered into adult rat brain, Journal of Neuroscience Methods, 105:77-86 (2001).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Kasuya, T. et al., In Vivo Delivery of Bionanocapsules Displaying *Phaseolus vulgaris* Agglutinin-$L_4$ Isolectin to Malignant Tumors Overexpressing N-Acetylglucosaminyltransferase V, Human Gene Therapy, 19:887-895 (2008).
Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).
Kaur, T. et al., Addressing the Challenge: Current and Future Directions in Ovarian Cancer THerapy, Current Gene Therapy, 9: 434-458 (2009).
Kiew, L.V. et al., Effect of antisense oligodeoxynucleotides for ICAM-1 on renal ischaemia-reperfusion injury in the anaesthetised rat, the Journal of Physiology, 557(3):981-989 (2004).
Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).
Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).
Klibanov, A.L. et al., Amphipathic polyethyleneglycols effectively prolong the circulation time of liposomes, FEBS, 268(1): 235-237 (1990).
Kober, L. et al., Optimized Signal Peptides for the Development of High Expressing CHO Cell Lines, Biotechnol. Bioeng., 110:1164-1173 (2012).
Kodama, K. et al., The Features and Shortcomings for Gene Delivery of Current Non-Viral Carriers, Current Medicinal Chemistry, 13: 2155-2161 (2006).
Kormann, M.S.D. et al., Expression of therapeutic proteins after delivery of chemically modified mRNA in mice, Nature Biotechnology, 29(2):154-157 (2011).
Kozak, M. An analysis of 5'-noncoding sequences from 699 vertebrate messenger RNAs, Nucleic Acid Research, 15(20):8125-8148 (1987).
Krieg, P.A. et al., In vitro RNA synthesis with SP6 RNA polymerase, Methods in Enzymology, 155:397-415 (1987).
Kvasnica, M. et al., Platinum(II) complexes with steroidal esters of L-methionine and L-histidine: Synthesis, characterization and cytotoxic activity, Bioorganic & Medicinal Chemistry, 16:3704-3713 (2008).
Lam, J.K.W et al., Pulmonary delivery of therapeutic siRNA, Advanced Drug Delivery Reviews (2011).
Lasic, D.D. et al., Gelation of liposome interior. A novel method for drug encapsulation, FEBS Letters, 312(2-3):255-258 (1992).
Lasic, D.D. Novel applications of liposomes, Trends in Biotechnology, 16:307-321 (1998).
Lee, S. et al., Stability and cellular uptake of polymerized siRNA (poly-siRNA)/polyethylenimine (PEI) complexes for efficient gene silencing. Journal of Controlled Release 141: 339-346 (2010).
Li, L. et al., Preparation and Gene Delivery of Alkaline Amino Acids-Based Cationic Liposomes, Archives of Pharmaceutical Research, 31(7):924-931 (2008).
Li, S. et al., In vivo gene transfer via intravenous administration of cationic lipid-protamine-DNA (LPD) complexes, Gene Therapy, 4:891-900 (1997).

(56) References Cited

OTHER PUBLICATIONS

Li, W. et al., Lipid-based Nanoparticles for Nucleic Acid Delivery, Pharmaceutical Research, 24(3):438-449 (2007).
Liebhaber, S.A. et al., Translation inhibition by an mRNA coding region secondary structure is determined by its proximity to the AUG initiation codon, Journal of Molecular Biology, 226(3):609-621 (1992).
Lim, Y. et al., A self-destroying polycationic polymer: biodegradable poly(4-hydroxy-1-proline ester). Journal of American Chemical Society 121: 5633-5639 (1999).
Lindgren, V. et al., Human Ornithine Transcarbamylase Locus Mapped to Band Xp21.1 Near the Duchenne Muscular Dystrophy Locus, Science, 226(2675):698-700 (1984).
Liu, X. et al., COStar: a D-star Lite-based Dynamic Search Algorithm for Codon Optimization, Journal of Theoretical Biology, 344:19-30 (2014).
Liu, Y. and Huang, L., Designer Lipids Advance Systematic siRNA Delivery, Molecular Therapy, 18(4):669-670 (2010).
Liu, Y. et al., Factors influencing the efficiency of cationic liposome-mediated intravenous gene delivery, Nature Biotechnology, 15:167-173 (1997).
Lo, K-M et al., High level expression and secretion of Fc-X fusion proteins in mammalian cells, Protein Engineering, 11(6):495-500 (1998).
Lorenzi, J. C. C. et al., Intranasal Vaccination with Messenger RNA as a New Approach in Gene Therapy: Use Against Tuberculosis, BMC Biotechnology, 10(77):1-11 (2010).
Love, K.T. et al., Lipid-like materials for low-dose, in vivo gene silencing, PNAS, 107(5):1864-1869 (2010).
Lu, D. et al., Optimization of methods to achieve mRNA-mediated transfection of tumor cells in vitro and in vivo employing cationic liposome vectors, Cancer Gene Therapy, 1(4):245-252 (1994).
Lukyanov, A.N. and Torchilin, V.P., Micelles from lipid derivatives of water-soluble polymers as delivery systems for poorly soluble drugs. Advanced Drug Delivery Reviews 56: 1273-1289 (2004).
Luo, D. and Saltzman, M., Synthetic DNA delivery systems. Nature Biotechnology 18: 33-37. Review (2000).
Lynn, D.M. and Langer, R., Degradable Poly(β-amino esters):? Synthesis, Characterization, and Self-Assembly with Plasmid DNA. Journal of American Chemical Society 122(44): 10761-10768 (2000).
Lynn, D.M. et al., Accelerated discovery of synthetic transfection vectors: parallel synthesis and screening of a degradable polymer library. Journal of American Chemical Society 123 (33): 8155-8156 (2001).
Lynn, D.M. et al., pH-Responsive Polymer Microspheres: Rapid Release of Encapsulated Material within the Range of Intracellular pH. Angewandte Chemie International Edition 40(9): 1707-1710 (2001).
Ma, M. et al., Development of Cationic Polymer Coatings to Regulate Foreign Body Responses. Advanced Healthcare Materials 23: H189-H194. Reviews (2011).
Maclachlan, I., Lipid nanoparticle-mediated delivery of messenger RNA, 1st International mRNA Health Conference; Tubingen Germany, (Oct. 24, 2013) Retrieved from the Internet: URL: <http://files.shareholder.com/downloads/ABEA-50QJTB/2628241206x0x699789/47543d12-db34-4e6e-88a9-f3ae5d97b1d2/MacLachlan_mRNA_Conf_2013>.
Maeda-Mamiya, R. et al., In vivo gene delivery by cationic tetraamino; fullerene. Proceedings of National Academy of Sciences U S A, 107(12):5339-5344 (2010).
Malone, R.W., et al., Cationic liposome-mediated RNA transfection, PNAS, 86:6077-6081 (1989).
Mammal, http://en.wikipedia.org/wiki/Mammal, 2007, Pearson Education, NY, NY, Author unkown (Source: the international union for conservation of nature and natural resources), 2 pages, (Retrieved Aug. 2, 2014).
Mansour, H.M. et al., Nanomedicine in pulmonary delivery, International Journal of Nanomedicine, 4:299-319 (2009).
Margus, H. et al., Cell-penetrating peptides as versatile vehicles for oligonucleotide delivery. Molecular Therapy 20 (3): 525-533 (2012).
Martell, A.E. and Chaberek, S., The Preparation and the Properties of Some N,N'-Disubstituted-ethylenediaminedipropionic Acids. Journal of the American Chemical Society 72: 5357-5361 (1950).
Martinon, F. et al., Induction of Virus-Specific Cytotoxic T Lymphocytes in Vivo by Liposome-Entrapped mRNA, European Journal of Immunology, 23(7):1719-1722 (1993).
Mathiowitz, E. and Langer, R., Polyanhydride microspheres as drug carriers I. Hot-melt microencapsulation. Journal of Controlled Release 5: 13-22 (1987).
Mathiowitz, E. et al., Novel microcapsules for delivery systems. Reactive Polymers 6: 275-283 (1987).
Mathiowitz, E. et al., Polyanhydride microspheres as drug carriers II. Microencapsulation by solvent removal. Journal of Applied Polymer Sciences 35: 755-774 (1988).
Mccracken, S. et al., 5'-Capping Enzymes are Targeted to Pre-MRNA by Binding to the Phosphorylated Carboxy-Terminal Domain of RNA Polymerase II, Genes and Development, 22(24):3306-3318 (1997).
Mcivor, R. S., Therapeutic Delivery of mRNA: the Medium is the Message, Molecular Therapy, 19(5):822-823 (2011).
Melton, D.A. et al., Efficient in vitro synthesis of biologically active RNA and RNA hybridization probes from; plasmids containing a bacteriophage SP6 promoter, Nucleic Acids Research, 12(18):7035-7056 (1984).
Mendelsohn, J.D. et al., Rational design of cytophilic and cytophobic polyelectrolyte multilayer thin films. Biomacromolecules 4(1): 96-106 (2003).
Merkel, O.M. and Kissel, T., Nonviral Pulmonary Delivery of siRNA, Accounts of Chemical Research, 45(7):961-970 (2012).
Merten, O. et al., Large-Scale Manufacture and Characterization of a Lentiviral Vector Produced for Clinical Ex Vivo Gene Therapy Application, Human Gene Therapy, 22(3):343-356 (2011).
Miller, A. Cationic Liposomes for Gene Therapy. Angewandte Chemie International Edition 37: 1768-1785 (1998).
Monia, B.P. et al., Evaluation of 2'-Modified Oligonucleotides Containing 2'-Deoxy Gaps as Antisense Inhibitors of Gene Epression, the Journal of Biological Chemistry, 268(19):14514-14522 (1993).
Morrissey, D.V. et al., Potent and Persistent in vivo Anti-HBV Activity of Chemically Modified siRNAs, Nat. Biotechnol., 23(8): 1003-1007 (2005).
Narang, A.S. et al., Cationic lipids with increased DNA binding affinity for nonviral gene transfer in dividing and nondividing cells. Bioconjugate Chemistry 16(1): 156-168 (2005).
Navarro, G. et al., Phospholipid-polyethylenimine conjugate-based micelle-like nanoparticles for siRNA delivery. Drug Delivery and Translational Research 1: 25-33 (2011).
Neamnark, A. et al., Aliphatic lipid substitution on 2 kDa polyethylenimine improves plasmid delivery and transgene expression. Molecular Pharmaceutics 6(6): 1798-1815 (2009).
Ng, J. et al., LincRNAs join the pluripotency alliance, Nature Genetics, 42:1035-1036 (2010).
Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).
Nguyen, D.N. et al., Drug delivery-mediated control of RNA immunostimulation. Molecular Therapy 17(9): 1555-1562 (2009).
Nojima, T. et al., The Interaction between Cap-binding Complex and RNA Export Factor is Required for Intronless mRNA Export, Journal of Biological Chemistry, 282(21):15645-15651 (2007).
Nori, A. et al., Tat-conjugated synthetic macromolecules facilitate cytoplasmic drug delivery to human ovarian carcinoma cells, Bioconj. Chem., 14(1): 44-50 (2003).
Okumura, K. et al., Bax mRNA therapy using cationic liposomes for human malignant melanoma, the Journal of Gene Medicine, 10:910-917 (2008).
Otsuka, Y. et al., Identification of a Cytoplasmic Complex That Adds a Cap onto 5'-Monophosphate RNA, Molecular and Cellular Biology, 29(8):2155-2167 (2009).
Ozer, A., Alternative applications for drug delivery: nasal and pulmonary routes, Nanomaterials and Nanosystems for Biomedical Applications, M.R. Mozafari (ed.): 99-112 (2007).

(56) References Cited

OTHER PUBLICATIONS

Painter, H. et al., Topical Delivery of mRNA to the Murine Lung and Nasal Epithelium, Gene Medicine Group and the Medical Informatics Unit, Nuffield Department of Clinical Laboratory Sciences, University of Oxford, 1 page.
Painter, H. et al., Topical Delivery of mRNA to the Murine Lung and Nasal Epithelium, Molecular Therapy, 9:S187 (2004).
Painter, H., An Investigation of mRNA as a Gene Transfer Agent, Gene Medicine Research Group Nuffield Department of Clinical Laboratory Sciences and Merton College, University of Oxford, 1-282 (2007).
Painter, H., An Investigation of mRNA as a Gene Transfer Agent, Oxford University GeneMedicine, Abstract Only, 1 page (2007).
Parrish, D.A. and Mathias, L.J., Five- and six-membered ring opening of pyroglutamic diketopiperazine. Journal of Organic Chemistry 67(6): 1820-1826 (2002).
Patton, J., Market Trends in Pulmonary Therapies, Trends and Opportunities, VI: 372-377.
Paulus, C. and Nevels, M., The Human Cytomegalovirus Major Immediate-Early Proteins as Antagonists of Intrinsic and Innate Antiviral Host Responses, Viruses, 1:760-779 (2009).
Peppas, N.A. et al., Hydrogels in Biology and Medicine: From Molecular Principles to Bionanotechnology. Advanced Materials 18: 1345-1360 (2006).
Philipp, A. et al., Hydrophobically modified oligoethylenimines as highly efficient transfection agents for siRNA delivery. Bioconjugate Chemistry 20(11): 2055-2061 (2009).
Pons, M. et al., Liposomes obtained by the ethanol injection method, Int. J. Pharm., 95: 51-56. (1993).
Prata, C.A. et al., Lipophilic peptides for gene delivery. Bioconjugate Chemistry 19(2): 418-420 (2008).
Probst, J. et al., Spontaneous cellular uptake of exogenous messenger RNA in vivo is nucleic acid-specific, saturable and ion dependent, Gene Therapy, 14:1175-1180 (2007).
Promega, PolyATtract mRNA Isolation Systems, Instructions for Use of Products Z5200, Z5210, Z2300 and Z5310, Technical Manual (2012).
Putnam, D. Polymers for gene delivery across length scales. Nature Materials 5: 439-451 (2006).
Putnam, D. and Langer, R., Poly(4-hydroxy-1-proline ester): Low-Temperature Polycondensation and Plasmid DNA Complexation. Macromolecules 32(11): 3658-3662 (1999).
Qiagen, Oligotex Handbook, Second Edition (2002).
Rabinovich, P.M. et al., Synthetic Messenger RNA as a Tool for Gene Therapy, Human Gene Therapy, 17:1027-1035 (2006).
Raper, S.E. et al., Developing adenoviral-mediated in vivo gene therapy for ornithine transcarbamylase deficiency, Journal of Inherited Metabolic Disease, 21:119-137 (1998).
Ratajczak, J. et al., Membrane-derived microvesicles: important and underappreciated mediators of cell-to-cell communication, Leukemia, 20:1487-1495 (2006).
Ratner, B.D. and Bryant, S., Biomaterials: where we have been and where we are going. Annual Review of Biomedical Engineering 6: 41-75 (2004).
Reddy, A. et al., The Effect of Labour and Placental Separation on the Shedding of Syncytiotrophoblast Microparticles, Cell-free DNA and mRNA in Normal Pregnancy and Pre-eclampsia, Placenta, 29: 942-949 (2008).
Rejman, J. et al., Characterization and transfection properties of lipoplexes stabilized with novel exchangeable polyethylene glycol-lipid conjugates, Biochimica et Biophysica Acta, 1660:41-52 (2004).
Remington: the Science and Practice of Pharmacy, 21st Edition, Philadelphia, PA. Lippincott Williams & Wilkins (2005).
Rosenecker, J. et al., Gene Therapy for Cystic Fibrosis Lung Disease: Current Status and Future Perspectives, Curr. Opin. Mol. Ther., 8:439-445 (2006).
Rosenecker, J. et al., Interaction of Bronchoalveolar Lavage Fluid with Polyplexes and Lipoplexes: Analysing the Role of Proteins and Glycoproteins, J. Gene. Med., 5:49-60 (2003).
Rowe, S.M. et al., Cystic Fibrosis, New Engl. J. Med. 352:1992-2001 (2005).
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).
Sahay, G. et al., Endocytosis of nanomedicines. Journal of Controlled Release 145: 182-195 (2010).
Sakiyama-Elbert, S.E. and Hubbell, J.A., Functional Biomaterials: Design of Novel Biomaterials. Annual Review of Materials Research 31: 183-201 (2001).
Schnierle, B.S. et al., Cap-specific mRNA (nucleoside-02'-)-methyltransferase and poly(A) polymerase stimulatory activities of vaccinia virus are mediated by a single protein, Proceedings of the National Academy of Sciences, 89:2897-2901 (1992).
Schreier, H., The new frontier: gene and oligonucleotide therapy, Pharmaceutica Acta Helvetiae, 68(3):145-159 (1994).
Semple, S.C. et al., Rational design of cationic lipids for siRNA delivery, Nature Biotechnology, 28(2): 172-176 (2010).
Shchori E., Poly(secondary Amine)s from Diacrylates and Diamines. Journal of Polymer Science 21(6):413-15 (1983).
Sherwood, R.F. Advanced drug delivery reviews: enzyme prodrug therapy, Adv. Drug Del. Rev., 22: 269-288 (1996).
Shimada, A. et al., Translocation Pathway of the Intratracheally Instilled Ultrafine Particles from the Lung into the Blood Circulation in the Mouse, Toxicologic Pathology, 34:949-957 (2006).
Siegwart, D.J. et al., Combinatorial synthesis of chemically diverse core-shell nanoparticles for intracellular delivery. Proceedings of the National Academy of the Sciences of the USA 108(32):12996-123001 (2011).
Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50):47615-47622 (2001).
Stern, L. et al., A novel antitumor prodrug platform designed to be cleaved by the endoprotease legumain, Bioconj. Chem., 20: 500-510 (2009).
Su, X. et al., Cytosolic Delivery Mediated via Electrostatic Surface Binding of mRNA to Degradable Lipid-Coated Polymeric Nanoparticles, Polymer Preprints, 51(2):668-669 (2010).
Su, X. et al., In Vitro and in Vivo mRNA Delivery Using Lipid-Enveloped pH-Responsive Polymer Nanoparticles, Molecular Pharmaceutics, 8(3):774-787 (2011).
Suri, M. et al., Genetics for Pediatricians, Remedica Publishing, (2005).
Szoka, F. and Papahadjopoulos, D., Comparative properties and methods of preparation of lipid vesicles (liposomes). Annual Review of Biophysics Bioengineering 9: 467-508 (1980).
Tagawa, M. et al., Gene expression and active virus replication in the liver after injection of duck hepatitis B virus DNA into the peripheral vein of ducklings, Journal of Hepatology, 24:328-334 (1996).
Takahashi, Y. et al., Development of safe and effective nonviral gene therapy by eliminating CpG motifs from plasmid DNA vector, Frontiers in Bioscience, S4: 133-141 (2012).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Tavernier, G. et al., mRNA as gene therapeutic: How to control protein expression, Journal of Controlled Release, 150:238-247 (2011).
Third Party Preissuance Submission Under 37 CFR § 1.290 (Oct. 25, 2013).

(56) References Cited

OTHER PUBLICATIONS

Thomas, C. E. et al., Progress and problems with the use of viral vectors for gene therapy, Nature Reviews/Genetics, 4: 346-358 (2003).
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).
Tsui, N.B. et al., Stability of endogenous and added RNA in blood specimens, serum, and plasma, Clinical Chemistry, 48(10):1647-1653 (2002).
Tsvetkov, D.E. et al., Neoglycoconjugates based on dendrimeric poly(aminoamides). Russian Journal of Bioorganic Chemistry 28(6): 470-486 (2002).
Tuschl, T. et al., Targeted mRNA degradation by double-stranded RNA in vitro, Genes and Development, 13(24):3191-3197 (1999).
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).
Van De Wetering, P. et al., Structure-activity relationships of water-soluble cationic methacrylate/methacrylamide polymers for nonviral gene delivery. Bioconjugate Chemistry 10(4): 589-597 (1999).
Van Der Gun, B.T.F et al., Serum insensitive, intranuclear protein delivery by the multipurpose cationic lipid Saint-2, Journal of Controlled Release, 123:228-238 (2007).
Van Tendeloo, V.F.I et al., mRNA-based gene transfer as a tool for gene and cell therapy, Current Opinion in Molecular Therapeutics, 9(5):423-431 (2007).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Varambally, S. et al., Genomic Loss of microRNA-101 Leads to Overexpression of Histone Methyltransferase EZH2 in Cancer, Science, 322:1695-1699 (2008).
Veronese, F.M. et al., PEG-doxorubicin conjugates: influence of polymer structure on drug release, in vitro cytotoxicity, biodistribution, and antitumor activity, Bioconj. Chem., 16(4): 775-784 (2005).
Viecelli, H. et al., Gene Therapy for Hepatic Diseases Using Non-Viral Minicircle-DNA Vector, Journal of Inherited Metabolic Disease, 35(1):S144 (2012).
Viecelli, H. et al., Gene therapy for liver diseases using non-viral minicircle-DNA vector, Human Gene Therapy, 23(10):A145 (2012).
Viecelli, H. et al., Gene therapy for liver diseases using non-viral minicircle-DNA vector, Molecular Therapy, 21(1):S136 (2013).
Vomelova, I. et al., Methods of RNA Purification. All Ways (Should) Lead to Rome, Folia Biologica, 55(6):242-251 (2009).
Von Harpe et al., Characterization of commercially available and synthesized polyethylenimines for gene delivery. Journal of Controlled Release 69(2):309-322 (2000).
Walde, P. et al., Preparation of Vesicles (Liposomes). Encyclopedia of Nanoscience and Nanotechnology. Nalwa, ed. American Scientific Publishers, Los Angeles 9:43-79 (2004).
Wang, H. et al., N-acetylgalactosamine functionalized mixed micellar nanoparticles for targeted delivery of siRNA to liver, Journal of Controlled Release, 166(2):106-114 (2013).
Wang, Y. et al., Systemic delivery of modified mRNA encoding herpes simplex virus 1 thymidine kinase for targeted cancer gene therapy, Molecular Therapy, 21(2):358-367 (2013).
Webb, M. et al., Sphinogomyeline-cholesterol liposomes significantly enhance the pharmacokinetic and therapeutic properties of vincristine in murine and human tumour models, British Journal of Cancer, 72(4):896-904 (1995).
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
Wetzer, B. et al., Reducible cationic lipids for gene transfer, Biochem. J., 356:747-756 (2001).
White, J.E. et al., Poly(hydroxyaminoethers): a New Family of Epoxy-Based Thermoplastics. Advanced Materials 12(23): 1791-1800 (2000).
White, J.E. et al., Step-growth polymerization of 10,11-epoxyundecanoic acid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).
Wiehe, J.M. et al., mRNA-mediated gene delivery into human progenitor cells promotes highly efficient protein expression, Journal of Cellular and Molecular Medicine, 11(3):521-530 (2007).
Williams, D. et al., A simple, highly efficient method for heterologous expression in mammalian primary neurons using cationic lipid-mediated mRNA transfection, Frontiers in Neuroscience, 4(181):1-20 (2010).
Written Opinion for PCT/US2010/058457, 14 pages (May 6, 2011).
Written Opinion for PCT/US2011/062459, 9 pages (Apr. 11, 2012).
Written Opinion for PCT/US2012/041663, 7 pages (Oct. 8, 2012).
Written Opinion for PCT/US2012/041724, 11 pages (Oct. 25, 2012).
Written Opinion for PCT/US2013/034602, 4 pages (Jun. 17, 2013).
Written Opinion for PCT/US2013/034604, 9 pages (Jun. 17, 2013).
Written Opinion for PCT/US2013/044769, 8 pages (Nov. 12, 2013).
Written Opinion for PCT/US2013/044771, 7 pages (Nov. 1, 2013).
Written Opinion for PCT/US2013/073672, 7 pages (Mar. 3, 2014).
Written Opinion for PCT/US2014/027422, 6 pages (Jul. 31, 2014).
Written Opinion for PCT/US2014/027602, 7 pages (Jul. 28, 2014).
Written Opinion for PCT/US2014/027717, 5 pages (Jul. 16, 2014).
Written Opinion for PCT/US2014/028330, 7 pages (Jul. 22, 2014).
Written Opinion for PCT/US2014/028441, 6 pages (Jul. 22, 2014).
Written Opinion for PCT/US2014/028498, 6 pages (Jul. 28, 2014).
Written Opinion for PCT/US2014/061786, 5 pages (Feb. 6, 2015).
Written Opinion for PCT/US2014/061793, 4 pages (Feb. 6, 2015).
Written Opinion for PCT/US2014/061830, 7 pages (Feb. 4, 2015).
Written Opinion for PCT/US2014/061841, 8 pages (Feb. 24, 2015).
Written Opinion for PCT/US2015/21403 (7 pages) mailed Jun. 15, 2015.
Wu, J. and Zern, M., Modification of liposomes for liver targeting, Journal of Hepatology, 24(6):757-763 (1996).
Wu, J. et al., Cationic lipid polymerization as a novel approach for constructing new DNA delivery agents. Bioconjugate Chemistry 12(2): 251-257 (2001).
Wurdinger, T. et al., A secreted luciferase for ex-vivo monitoring of in vivo processes, Nat. Methods, 5(2):171-173 (2008).
Yamamoto, A. et al., Current prospects for mRNA gene delivery, European Journal of Pharmaceutics and Biopharmaceutics, 71(3): 484-489 (2009).
Yamamoto, Y. et al., Important Role of the Proline Residue in the Signal Sequence that Directs the Secretion of Human Lysozyme in *Saccharomyces cerevisiae*, Biochemistry, 28:2728-2732 (1989).
Yasuda, M. et al., Fabry Disease: Novel [alpha]-Galactosidase A 3-terminal Mutations Result in Multiple Transcripts Due to Aberrant 3-End Formation, American Journal of Human Genetics, 73:162-173 (2003).
Ye, X. et al., Nucleic Acids, Protein Synthesis, and Molecular Genetics: Prolonged Metabolic Correction in Adult Ornithine Transcarbamylase-deficient Mice with Adenoviral Vectors, The Journal of Biological Chemistry, 271:3639-3646 (1996).
Yokoe, H. et al., Spatial dynamics of GFP-tagged proteins investigated by local fluorescence enhancement, Nature Biotechnology, 14(10):1252-1256 (1996).

(56) References Cited

OTHER PUBLICATIONS

Yoneda et al., A cell-penetrating peptidic GRP78 ligand for tumor cell-specific prodrug therapy, Bioorg. Med. Chern. Lett., 18(5): 1632-1636 (2008).
Yoshioka, Y. and Calvert, P., Epoxy-based Electroactive Polymer Gels. Experimental Mechanics 42(4): 404-408 (2002).
Zagridullin, P.H. et al., Monobasic amines. II. Cycloalkylation and hydroxyalkylation of cyclic and acyclic di- and polyamines. Journal of Organic Chemistry26(1):184-88. Russian (1990).
Zaugg, H.E. et al., 3-Carboxy-2,5-piperazinedione and Derivatives. Journal of American Chemical Society 78(11):2626-2631 (1956).
Zauner, W. et al., Polylysine-based transfection systems utilizing receptor-mediated delivery. Advanced Drug Delivery Reviews 30(1-3):97-113(1998).
Zintchenko, A. et al., Simple modifications of branched PEI lead to highly efficient siRNA carriers with low toxicity. Bioconjugate Chemistry 19(7):1448-1455 (2008).
Zou, S. et al., Lipid-mediated delivery of RNA is more efficient than delivery of DNA in non-dividing cells, International Journal of Pharmaceutics, 389(1-2):232-243 (2010).
Baboo et al., "'Dark matter' worlds of unstable RNA and protein", Nucleus, 2014, 5:4 281-286.
Bhaduri, S. et al., "Procedure for the Preparation of Milligram Quantities of Adenovirus Messenaer Ribonucleic Acid", Journal of Viroloay, 2(6):1126-1129, (1972).
Kariko et al., "Generating the optimal mRNA for therapy: HPLC purification eliminates immune activation and improves translation of nucleoside-modified, protein-encoding mRNA", Nucleic Acids Research, pp. 1-10 (2011).
Lee et al., "A Polynucleotide Segment Rich in Adenylie Acid in the Rapidly-Labeled Polyribosomal RNA Component of Mouse Sarcoma 180 Ascites Cells", PNAS 68(6): 13331-35 (Jun. 1971).
Lee et al., "Tiny abortive initiation transcripts exert antitermination activity on an RNA hairpin-dependent intrinsic terminator", Nucleic Acids Research, 38(18): 6045-53 (2010).
Wurm F.M., "Review: Production of recombinant protein therapeutics in cultivated mammalian cells", Nature Biotechnology, 22(11): 1393-8 (Nov. 2004).
Kern et al., "Application of a Fed-Batch System to Produce RNA by In Vitro Transcription", Biotechnol. Prog. 15 :174 (1999).
Chomczynski et al., "Single-step method of RNA isolation by acid guanidinium thiocyanate-phenol-chloroform extraction", Analytical Biochemistry 162(1): 156-9 (1987).
Cowan et al., Boichem. Cell Biol. 80 745 (2002).
Kahn et al., Biotech. Bioeng. 69: 101 (2000).
Kariko et al., Modern Therapy 16(11): 1833 (2008).
Keith et al., Biotech. Bioeng. 38: 557 (1991).
Krieg et al., Nucleic Acids Research 12 (18): 7057 (1984).
Kormann et al., Nature Biotechnology 29 (2): 154 (2011).
Martin et al., RNA 4:226(1998).
Novagen, "Bug Buster Protein Extraction Protocol/Reagent". downloaded from the internet on Aug. 3, 2017.
Schwartz, "Tangential Flow Filtration", downloaded from the internet on Aug. 3, 2017.
Pokroskaya et al., Analytical Biochemistry 220: 420 (1994).
Rosemeyer et al., Analytical Biochemistry 224: 446 (1995).
You et al., Cell Biology International Reports 16(7): 663 (1992).
Ross et al., PNAS 69 (1): 264 (1972).
Nakanishi et al., "New Transfection Agents Based on Liposomes ContainingBiosurfactant MEL-A", Pharmaceuticals, 5(3): 411-420 (2013).
Robinson et al., "Lipid Nanoparticle-Delivered Chemically Modified mRNA Restores Chloride Secretion in Cystic Fibrosis", Molecular Therapy 26(8): 1-13 (2018).
B P De et al., "Characterization of an in vitro system for the synthesis of mRNA from human parainfluenza virus type 3," J Virol. 64(3):1135-42 (1990).
Promega, "Riboprobe® in vitro Transcription Systems," (2001) (24 pages).
Beckert et al., "Synthesis of RNA by in vitro Transcription," Methods in Molecular Biology, Ch. 3, pp. 29-41 (Year: 2011).
Choi et al., "Purifying mRNAs with a high-affinity elF4E mutant identifies the short 3' poly(A) end phenotype," PNAS 100(12) : 7033-7038 (Year: 2003).
Jacob, "Histone-Gene Reiteration in the Genome of a Mouse," Euro. J. of Biochemistry, 65, pp. 275-284 (1976).
Moss et al., "Histone mRNAs contain blocked and methylated 5' terminal sequences but lack methylated nucleosides at internal positions," Cell 10, pp. 113-120 (1977).
Ramanathan et al., "Survey and Summary mRNA capping: biological functions and applications," Nucleic Acids Research, 44(16), pp. 7511-7526 (2016).
Shatkin et al., "The ends of the affair: Capping and polyadenylation," Nature Structural Biology, 7(10), pp. 838-842 (2000).
Woo et al., "Physical and Chemical Characterization of Purified Ovalbumin Messenger RNA," J. of Biological Chemistry, 250(17), pp. 7027-7039 (1975).
Gallie, "The cap and poly(A) tail function synergistically to regulate mRNA translational efficiency", Genes & Development, 1991, 5: 2108-2116.
Gurevich et al., "Preparative in vitro mRNA synthesis using SP6 and T7 RNA polymerases", Analytical Biochemistry, 1991, 195: 207.
Hallsworth et al., "Chaotropic solutes cause water stress in Pseudomonas putida", Environmental Microbiology, 2003, 5(12): 1270-1280.
Kedes, "Histone genes and histone messengers", Annual Reviews Biochemistry, 1979, 48: 837-870.
Lukavsky et al., "Large -scale preparation and purification of polyacrylamide-free RNA oligonucleotides", RNA, 2004, 10: 889-893.
Rosen et al., "Preparation and preliminary characterization of purified ovalbumin messenger RNA from the hen oviduct", Biochemistry, 1975, 14(1): 69-78.
Costa et al., "Direct demonstration that the abundant 6-kilobase herpes simplex virus type 1 mRNA mapping between 0.23 and 0.27 map units encodes the major capsid protein VP5", Journal of Virology, Research Article, Jan. 1, 1984, pp. 287-292.
Nagata et al., "Synthesis and biological activity of artificial mRNA prepared with novel phosphorylating reagents", Nucleic Acids Research, Nov. 2010, 38(21): 7845-7857.
Takenaka et al., "Two forms of secreted and thermostable luciferases from the marine copepod crustacean, Metridia pacifica", Gene, Dec. 1, 2008, 425(1-2): 28-35, Epublished Aug. 7, 2008.
Consolidated List of Citations for Oppositions filed against European Patent Application No. 18205176.3, received with European Patent Office Communication of a notice of opposition dated Feb. 27, 2025.
Bhaduri et al., Procedure for the Preparation of Milligram Quantities of Adenovirus Messenger Ribonucleic Acid, Journal of Virology, Dec. 1972, 10(6): 1126-1129.
Fernandez et al., Cross Flow Filtration of RNA Extracts by Hollow Fiber Membrane, Acta Biotechnologica, 1992, 12(1): 49-56.
Promega Corporation, Riboprobe® in vitro Transcription Systems, Technical Manual No. 016, Sep. 1, 2001.
De et al., Characterization of an In Vitro System for the Synthesis of mRNA from Human Parainfluenza Virus Type 3, Journal of Virology, Mar. 1990, 64(3): 1135-1142.
U.S. Appl. No. 61/784,996,filed Mar. 14, 2013 (Michael Heartlein et al.).
Beckert et al., Synthesis of RNA by in vitro transcription, Methods Mol Biol., 2011, Chapter 3; 703: 29-41.
Eon-Duval et al., Removal of RNA impurities by tangential flow filtration in an RNase-free plasmid DNA purification process, Analytical Biochemistry, 2003, 316(2003): 66-73.
Schwartz et al., Scientific & Technical Report "PN 33213", Pall Life Sciences, Feb. 2003 (see last page).
Geall et al., Nonviral Delivery of Self-Amplifying RNA Vaccines, PNAS, Sep. 4, 2012, 109(36): 14604-14609.
AMBION by Life Technologies, MEGAscript® Kit Instruction Manual, Sep. 14, 2012 (see last page).
Agencourt® Cleanseq® Dye-Terminator Removal, Protocol 000600v032, 2006.

(56) References Cited

OTHER PUBLICATIONS

Letter sent by the Applicant to the EPO during the examination phase for European Patent Application No. 18205176.3, dated Jul. 7, 2021.
Vicente et al., Purification of recombinant baculoviruses for gene therapy using membrane processes, Gene Therapy, 2009, 16: 766-775.
Rayner et al, Totally Pure RNA, Promega Notes, 2004, 86: 15-17.
Qiagen, "RNA size and other factors affecting yield", Retrieved from url: <https://www.giagen.com/us/knowledge-and-support/knowledge-hub/bench-guide/rna/introduction/rna-numbers-size-molecular-weight-distribution-yield-and-conversions#> on Nov. 6, 2025.
Qiagen, "RNeasy Micro Handbook", Apr. 2003.
Rosenow et al, "Prokaryotic RNA preparation methods useful for high density array analysis: comparison of two approaches", Nucleic Acids Research, Nov. 15, 2001, 29(22): e112.
Weissman et al., "HPLC Purification of In Vitro Transcribed Long RNA" Synthetic Messenger RNA and Cell Metabolism Modulation: Methods and Protocols, Methods in Molecular Biology, 2013, 969(3): 43-54.
Patentee's Comments on the Opponent's Mar. 27, 2026 Written Submissions filed under Rule 116 EPC, for European Patent No. 3467108 (EP Patent Application No. 18205176.3), submitted by Carpmaels & Ransford to the European Patent Office on May 7, 2026.
Updated Consolidated List of Opposition Documents European Patent No. 3467108 (EP Patent Application No. 18205176.3), dated May 7, 2026.
Chomczynski et al., "The single-step method of RNA isolation by acid guanidinium thiocyanate-phenol-chloroform extraction: twenty-something years on", Nature Protocols, Jun. 27, 2006, 1(2): 581-585.
Thermofisher Scientific, "TechNotes: Improve RNA Isolation for Array Analysis and More: RiboPure™ Technology—for Tissue, Cells, Blood, Bacteria and Yeast", Retrieved May 14, 2026, from URL: https://www.thermofisher.com/us/en/home/references/ambion-tech-support/rna-isolation/tech-notes/improve-rna-isolation-for-array-analysis-and-more-.html.
Sanofi, Experimental Methods and Results Report: in vitro synthesised mRNA, May 7, 2026, 4 pages.
Guillerez et al., "A mutation in T7 RNA polymerase that facilitates promoter clearance", PNAS, Apr. 26, 2005, 102(17): 5958-5963. Epub Apr. 14, 2005.
Sousa et al., "Progress in Nucleic Acid Research and Molecular Biology", 2003, vol. 73, Elsevier. Chapter IV, pp. 18-21.
Shin et al, "Effects of saturation mutagenesis of the phage SP6 promoter on transcription activity, presented by activity logos", PNAS, Apr. 11, 2000, 97(8): 3890-3895.
Nam et al., "Transcription initiation site selection and abortive initiation cycling of phage SP6 RNA polymerase", Journal of Biological Chemistry, Dec. 5, 1988, 263(34): 18123-18127.
Kanto Chemical Holdings, "Agarose for electrophoresis, KANTO series", Machine English Translation included, Retrieved Nov. 1, 2024, from URL: https://web.archive.org/web/20241101193342/https://www.kanto.co.jp/products/baio/dna_rna/bio_electrophoresis/agarose_kanto.html.
Thermofisher Scientific, "Protein Gel Staining Methods", Retrieved May 14, 2026, from URL: https://www.thermofisher.com/us/en/home/life-science/protein-biology/protein-biology-learning-center/protein-biology-resource-library/pierce-protein-methods/protein-gel-stains.html.
Yamamoto et al., "Quality Evaluation Points and Analytical Methods for mRNA-based Therapeutics", Pharmaceutical and Medical Device Regulatory Science, 2023, 54(4): 300-311.
Green et al., "Precipitation of RNA with Ethanol", Cold Spring Harb Protocols, Mar. 2, 2020, 2020(3): 101717.
Life Technologies, Ambion User Guide, MEGAclear™ Kit Purification for Large Scale Transcription Reactions, Sep. 28, 2012.
Murphy et al., "Poly(A) tail dynamics: Measuring polyadenylation, deadenylation and poly(A) tail length", Methods Enzymol., May 3, 2021, 655: 265-290.
Synapse, "What is the mechanism of Isopropyl Alcohol?", Jul. 18, 2024, Retrieved from url: <https://synapse.patsnap.com/article/what-is-the-mechanism-of-isopropyl-alcohol>.
Chen et al., "Immunologic detection of protein antigens after phenol-chloroform denaturation", Gene Analysis Techniques, Mar.-Apr. 1989, 6(2): 44-46, Retrieved from url: <https://www.sciencedirect.com/science/article/abs/pii/0735065189900265>.
Ausubel et al., "Purification of Oligonucleotides Using Denaturing Polyacrylamide Gel Electrophoresis", Current Protocols in Molecular Biology, 1998, Unit 2.12, Preparation and Analysis of DNA, Supplement 42, pp. 2.12.1-2.12.7.
U.S. Appl. No. 14/775,915, 2016/0040154, U.S. Pat. No. 9,957,499, filed Sep. 14, 2015, Feb. 11, 2016, May 1, 2018, Michael Heartlein, Methods for Purification of Messenger RNA.
U.S. Appl. No. 15/936,289, 2018/0237766, U.S. Pat. No. 10,876,104, filed Mar. 26, 2018, Aug. 23, 2018, Dec. 29, 2020, Michael Heartlein, Methods for Purification of Messenger RNA.
U.S. Appl. No. 17/103,439, 2021/0324368, U.S. Pat. No. 12,234,446, filed Nov. 24, 2020, Oct. 21, 2021, Feb. 25, 2025, Michael Heartlein, Methods for Purification of Messenger RNA.
U.S. Appl. No. 17/835,710, 2022/0389403, U.S. Pat. No. 11,820,977, filed Jun. 8, 2022, Dec. 8, 2022, Nov. 21, 2023, Frank DeRosa, Methods for Purification of Messenger RNA.
U.S. Appl. No. 17/835,725, 2022/0411781, U.S. Pat. No. 11,692,189, filed Jun. 8, 2022, Dec. 29, 2022, Jul. 4, 2023, Frank DeRosa, Methods for Purification of Messenger RNA.
U.S. Appl. No. 17/835,738, 2022/0348899, filed Jun. 8, 2022, Nov. 3, 2022, Frank DeRosa, Methods for Purification of Messenger RNA.

* cited by examiner

```
                         SEQUENCE LISTING

<160> NUMBER OF SEQ ID NOS: 7

<210> SEQ ID NO 1
<211> LENGTH: 1671
<212> TYPE: RNA
<213> ORGANISM: Artificial Sequence
<220> FEATURE:
<223> OTHER INFORMATION: chemically synthesized oligonucleotide

<400> SEQUENCE: 1

gggauccuac cauggaagau gccaaaaaca uuaagaaggg cccagcgcca uucuacccac      60

ucgaagacgg gaccgccggc gagcagcugc acaaagccau gaagcgcuac gcccuggugc     120

ccggcaccau cgccuuuacc gacgcacaua ucgaggugga cauuaccuac gccgaguacu     180

ucgagaugag cguucggcug gcagaagcua ugaagcgcua ugggcugaau acaaaccauc     240

ggaucguggu gugcagcgag aauagcuugc aguucuucau gcccguguug ggugcccugu     300

ucaucggugu ggcuguggcc ccagcuaacg acaucuacaa cgagcgcgag cugcugaaca     360

gcaugggcau cagccagccc accgucguau ucgugagcaa gaaagggcug caaaagaucc     420

ucaacgugca aaagaagcua ccgaucauac aaaagaucau caucauggau agcaagaccg     480

acuaccaggg cuuccaaagc auguacaccu ucgugacuuc ccauuugcca cccggcuuca     540

acgaguacga cuucgugccc gagagcuucg accgggacaa aaccaucgcc cugaucauga     600

acaguagugg caguaccgga uugcccaagg gcguagcccu accgcaccgc accgcuugug     660

uccgauucag ucaugcccgc gaccccaucu ucggcaacca gaucaucccc gacaccgcua     720

uccucagcgu ggugccauuu caccacggcu ucggcauguu caccacgcug ggcuacuuga     780

ucugcggcuu ucgggucgug cucauguacc gcuucgagga ggagcuauuc uugcgcagcu     840

ugcaagacua uaagauucaa ucugcccugc uggugcccac acuauuuagc uucuucgcua     900

agagcacucu caucgacaag uacgaccuaa gcaacuugca cgagaucgcc agcggcgggg     960

cgccgcucag caaggaggua ggugaggccg uggccaaacg cuuccaccua ccaggcaucc    1020

gccagggcua cggccugaca gaaacaacca gcgccauucu gaucaccccc gaaggggacg    1080

acaagccugg cgcaguaggc aagguggugc ccuucuucga ggcuaaggug guggacuugg    1140

acaccgguaa gacacugggu gugaaccagc gcggcgagcu gugcguccgu ggccccauga    1200

ucaugagcgg cuacguuaac aaccccgagg cuacaaacgc ucucaucgac aaggacggcu    1260

ggcugcacag cggcgacauc gccuacuggg acgaggacga gcacuucuuc aucguggacc    1320

ggcugaagag ccugaucaaa uacaagggcu accagguagc cccagccgaa cuggagagca    1380

uccugcugca acaccccaac aucuucgacg ccggggucgc cggccugccc gacgacgaug    1440

ccggcgagcu gcccgccgca gucgucgugc uggaacacgg uaaaaccaug accgagaagg    1500

agaucgugga cuauguggcc agccagguua caaccgccaa gaagcugcgc ggugguguug    1560

uguucgugga cgaggugccu aaaggacuga ccggcaaguu ggacgcccgc aagauccgcg    1620
```

agauucucau uaaggccaag aagggcggca agaucgccgu guauuugaau u 1671

<210> SEQ ID NO 2
<211> LENGTH: 11
<212> TYPE: RNA
<213> ORGANISM: Artificial Sequence
<220> FEATURE:
<223> OTHER INFORMATION: chemically synthesized oligonucleotide

<400> SEQUENCE: 2
gggauccuac c 11

<210> SEQ ID NO 3
<211> LENGTH: 8
<212> TYPE: RNA
<213> ORGANISM: Artificial Sequence
<220> FEATURE:
<223> OTHER INFORMATION: chemically synthesized oligonucleotide

<400> SEQUENCE: 3 uuugaauu 8

<210> SEQ ID NO 4
<211> LENGTH: 1626
<212> TYPE: RNA
<213> ORGANISM: Artificial Sequence
<220> FEATURE:
<223> OTHER INFORMATION: chemically synthesized oligonucleotide

<400> SEQUENCE: 4
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg augcagcgcg ugaacaugau cauggcagaa ucaccaggcc 180
ucaucaccau cugccuuuua ggauaucuac ucagugcuga auguacaguu uuucuugauc 240
augaaaacgc caacaaaauu cugaggcgga gaaggaggua uaauucaggu aaauuggaag 300
aguuuguuca agggaaccuu gagagagaau guauggaaga aaaguguagu uuugaagaag 360
cacgagaagu uuuugaaaac acugaaagaa caacugaauu uuggaagcag uauguugaug 420
gagaucagug ugaguccaau ccauguuuaa auggcggcag uugcaaggau gacauuaauu 480
ccuaugaaug uugguguccc uuuggauuug aaggaaagaa cugugaauua gauguaacau 540
guaacauuaa gaauggcaga ugcgagcagu uuuguaaaaa uagugcugau aacaaggugg 600
uuugcuccug uacugaggga uaucgacuug cagaaaacca gaaguccugu gaaccagcag 660
ugccauuucc auguggaaga guuucuguuu cacaaacuuc uaagcucacc cgugcugagg 720
cuguuuuucc ugauguggac uauguaaauu cuacugaagc ugaaaccauu uuggauaaca 780
ucacucaaag cacccaauca uuuaaugacu ucacucgggu uguuggugga gaagaugcca 840
aaccagguca auucccuugg cagguuguuu ugaaugguaa aguugaugca uucuguggag 900
gcucuaucgu uaaugaaaaa uggauuguaa cugcugccca cuguguugaa acugguguua 960
aaauuacagu ugucgcaggu gaacauaaua uugaggagac agaacauaca gagcaaaagc 1020
gaaaugugau ucgaauuauu ccucaccaca acuacaaugc agcuauuaau aaguacaacc 1080
augacauugc ccuucuggaa cuggacgaac ccuuagugcu aaacagcuac guuacaccua 1140
uuugcauugc ugacaaggaa uacacgaaca ucuuccucaa auuuggaucu ggcuauguaa 1200
guggcugggg aagagucuuc cacaaaggga gaucagcuuu aguucuucag uaccuuagag 1260
uuccacuugu ugaccgagcc acaugucuuc gaucuacaaa guucaccauc uauaacaaca 1320
uguucugugc uggcuuccau gaaggaggua gagauucaug ucaaggagau aguggggac 1380 cccauguuac ugaaguggaa gggaccaguu ucuuaacugg aauuauuagc uggggugaag 1440
agugugcaau gaaaggcaaa uauggaauau auaccaaggu aucccgguau gucaacugga 1500
uuaaggaaaa aacaaagcuc acuuaacggg uggcaucccu gugaccccuc cccagugccu 1560
cuccuggccc uggaaguugc cacuccagug cccaccagcc uuguccuaau aaaauuaagu 1620
ugcauc 1626

<210> SEQ ID NO 5
<211> LENGTH: 140
<212> TYPE: RNA
<213> ORGANISM: Artificial Sequence
<220> FEATURE:
<223> OTHER INFORMATION: chemically synthesized oligonucleotide

<400> SEQUENCE: 5
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg 140

<210> SEQ ID NO 6
<211> LENGTH: 100
<212> TYPE: RNA
<213> ORGANISM: Artificial Sequence
<220> FEATURE:
<223> OTHER INFORMATION: chemically synthesized oligonucleotide

<400> SEQUENCE: 6
cggguggcau cccugugacc ccuccccagu gccucuccug gcccuggaag uugccacucc 60
agugcccacc agccuugucc uaauaaaauu aaguugcauc 100

<210> SEQ ID NO 7
<211> LENGTH: 4683
<212> TYPE: RNA
<213> ORGANISM: Artificial Sequence
<220> FEATURE:
<223> OTHER INFORMATION: chemically synthesized oligonucleotide

<400> SEQUENCE: 7
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg augcagcggu ccccgcucga aaaggccagu gucgugucca 180
aacucuucuu cucauggacu cggccuaucc uuagaaaggg guaucggcag aggcuugagu 240
ugucugacau cuaccagauc cccucgguag auucggcgga uaaccucucg gagaagcucg 300
aacgggaaug ggaccgcgaa cucgcgucua agaaaaaccc gaagcucauc aacgcacuga 360
gaaggugcuu cuucuggcgg uucauguucu acgguaucuu cuuguaucuc ggggagguca 420
caaaagcagu ccaaccccug uuguugggUc gcauuaucgc cucguacgac cccgauaaca 480
aagaagaacg gagcaucgcg aucuaccucg ggaucggacu guguuugcuu uucaucguca 540
gaacacuuuu guugcaucca gcaaucuucg gccuccauca caucgguaug cagaugcgaa 600
ucgcuauguu uagcuugauc uacaaaaaga cacugaaacu cucgucgcgg guguuggaua 660
agauuuccau cggucaguug gugucccugc uuaguaauaa ccucaacaaa uucgaugagg 720
gacuggcgcu ggcacauuuc guguggauug ccccguugca agucgcccuu uugaugggcc 780

-continued

```
uuauuuggga gcuguugcag gcaucugccu uuuguggccu gggauuucug auuguguugg    840
cauuguuuca ggcugggcuu gggcggauga ugaugaagua ucgcgaccag agagcgggua    900
aaaucucgga aagacucguc aucacuucgg aaaugaucga aaacauccag ucggucaaag    960
ccuauugcug ggaagaagcu auggagaaga ugauugaaaa ccuccgccaa acugagcuga   1020
aacugacccg caaggcggcg uauguccggu auuucaauuc gucagcguuc uucuuuuccg   1080
gguucuucgu ugucuuucuc ucgguuuugc cuuaugccuu gauuaagggg auuauccucc   1140
gcaagauuuu caccacgauu ucguucugca uuguauugcg cauggcagug acacggcaau   1200
uuccgugggc cgugcagaca ugguaugacu cgcuuggagc gaucaacaaa auccaagacu   1260
ucuugcaaaa gcaagaguac aagacccugg aguacaaucu uacuacuacg gagguaguaa   1320
uggagaaugu gacggcuuuu ugggaagagg guuuuggaga acuguuugag aaagcaaagc   1380
agaauaacaa caaccgcaag accucaaaug ggacgauuc ccuguuuuuc ucgaacuucu   1440
cccugcucgg aacacccgug uugaaggaca ucaauuucaa gauugagagg ggacagcuuc   1500
ucgcgguagc gggaagcacu ggugcgggaa aaacuagccu cuugauggug auuauggggg   1560
agcuugagcc cagcgagggg aagauuaaac acuccgggcg uaucucauuc uguagccagu   1620
uuucauggau caugcccgga accauuaaag agaacaucau uuucggagua uccuaugaug   1680
aguaccgaua cagaucgguc auuaaggcgu gccaguugga agaggacauu ucuaaguucg   1740
ccgagaagga uaacaucguc uugggagaag gggguauuac auugucggga gggcagcgag   1800
cgcggaucag ccucgcgaga gcgguauaca aagaugcaga uuuguaucug cuugauucac   1860
cguuuggaua ccucgacgua uugacagaaa aagaaaucuu cgagucgugc guguguaaac   1920
uuauggcuaa uaagacgaga auccugguga caucaaaaau ggaacaccuu aagaaggcgg   1980
acaagauccu gauccuccac gaaggaucgu ccuacuuuua cggcacuuuc ucagaguugc   2040
aaaacuugca gccggacuuc ucaagcaaac ucaugggggug ugacucauuc gaccaguuca   2100
gcgcggaacg gcggaacucg aucuugacgg aaacgcugca ccgauucucg cuugagggug   2160
augccccggu aucgguggacc gagacaaaga agcagucguu uaagcagaca ggagaauuug   2220
gugagaaaag aaagaacagu aucuugaauc cuauuaacuc aauucgcaag uucucaaucg   2280
uccagaaaac uccacugcag augaauggaa uugaagagga uucggacgaa ccccuggagc   2340
gcaggcuuag ccucgugccg gauucagagc aaggggaggc cauucuuccc cggauuucgg   2400
ugauuucaac cggaccuaca cuucaggcga ggcgaaggca auccgugcuc aaccucauga   2460
cgcauucggu aaaccagggg caaaacauuc accgcaaaac gacggccuca acgagaaaag   2520
ugucacuugc accccaggcg aauuugacug aacucgacau cuacagccgu aggcuuucgc   2580
aagaaaccgg acuugagauc agcgaagaaa ucaaugaaga agauuugaaa gaguguuucu   2640
uugaugacau ggaaucaauc ccagcgguga caacguggaa cacauacuug cguuacauca   2700
cggugcacaa guccuugauu uucguccuca ucugguguucu cgugaucuuu cucgcugagg   2760
ucgcagcguc acuuguggggucc cucuggcugc uugguaauac gcccuugcaa gacaaaggca   2820
auucuacaca cucaagaaac aauuccuaug ccgugauuau cacuucuaca agcucguauu   2880
acguguuuua caucuacgua ggaguggccg acacucugcu cgcgaugggu uucuuccgag   2940
gacucccacu cguucacacg cuuaucacug ucuccaagau ucuccaccau aagaugcuuc   3000
auagcguacu gcaggcuccc auguccaccu ugaauacgcu caaggcggga gguauuuuga   3060
aucgcuucuc aaaagauauu gcaauuuugg augaccuucu gccccugacg aucuucgacu   3120
```

-continued

```
ucauccaguu guugcugauc gugauugggg cuauugcagu agucgcuguc cuccagccuu   3180
acauuuuugu cgcgaccguu ccggugaucg uggcguuuau caugcugcgg gccuauuucu   3240
ugcagacguc acagcagcuu aagcaacugg agucugaagg gaggucgccu aucuuuacgc   3300
aucuugugac caguuugaag ggauugugga cguugcgcgc cuuuggcagg cagcccuacu   3360
uugaaacacu guuccacaaa gcgcugaauc uccauacggc aaauugguuu uuguauuuga   3420
guacccuccg augguuucag augcgcauug agaugauuuu ugugaucuuc uuuaucgcgg   3480
ugacuuuuau cuccaucuug accacgggag agggcgaggg acgggucggu auuauccuga   3540
cacucgccau gaacauuaug agcacuuugc agugggcagu gaacagcucg auugaugugg   3600
auagccugau gagguccguu ucgagggucu uuaaguucau cgacaugccg acggagggaa   3660
agcccacaaa aaguacgaaa cccuauaaga augggcaauu gaguaaggua augaucaucg   3720
agaacaguca cgugaagaag gaugacaucu ggccuagcgg gggucagaug accgugaagg   3780
accugacggc aaaauacacc gagggaggga acgcaauccu ugaaaacauc ucguucagca   3840
uuagccccgg ucagcgugug gguugcucg ggaggaccgg gucaggaaaa ucgacguugc   3900
ugucggccuu cuugagacuu cugaauacag agggugagau ccagaucgac ggcguuucgu   3960
gggauagcau caccuugcag caguggcgga aagcguuugg aguaaucccc caaaaggucu   4020
uuaucuuuag cggaaccuuc cgaaagaauc ucgauccuua ugaacagugg ucagaucaag   4080
agauuuggaa agucgcggac gagguuggcc uucggagugu aaucgagcag uuuccgggaa   4140
aacucgacuu uguccuugua gauggggau gcguccuguc gcaugggcac aagcagcuca   4200
ugugccuggc gcgauccguc cucucuaaag cgaaaauucu ucucuuggau gaaccuucgg   4260
cccaucugga cccgguaacg uaucagauca ucagaaggac acuuaagcag gcguuugccg   4320
acugcacggu gauucucugu gagcaucgua ucgaggccau gcucgaaugc cagcaauuuc   4380
uugucaucga agagaauaag guccgccagu acgacuccau ccagaagcug cuuaaugaga   4440
gaucauuguu ccggcaggcg auuucaccau ccgauagggu gaaacuuuuu ccacacagaa   4500
auucgucgaa gugcaagucc aaaccgcaga ucgcggccuu gaaagaagag acugaagaag   4560
aaguucaaga cacgcgucuu uaacgggugg caucccugug accccucccc agugccucuc   4620
cuggcccugg aaguugccac uccagugccc accagccuug uccuaauaaa auuaaguugc   4680
auc                                                                 4683
```

METHODS FOR PURIFICATION OF MESSENGER RNA

CROSS REFERENCE TO RELATED APPLICATIONS

This patent application is a continuation application of U.S. patent application Ser. No. 17/103,439, filed Nov. 24, 2020, which is a continuation application of U.S. patent application Ser. No. 15/936,289, filed Mar. 26, 2018, now United States U.S. Pat. No. 10,876,104, issued Dec. 29, 2020 which is a continuation application of U.S. patent application Ser. No. 14/775,915, filed on Sep. 14, 2015, now United States U.S. Pat. No. 9,957,499, issued May 1, 2018, which is a 35 U.S.C. § 371 National Stage application of International Application No. PCT/US14/28441, filed Mar. 14, 2014, which claims the benefit of United States Provisional Patent Application No. 61/784,996, filed Mar. 14, 2013, the entireties of which is are incorporated herein by reference.

INCORPORATION-BY-REFERENCE OF SEQUENCE LISTING

The instant application contains a Sequence Listing which has been submitted electronically in ASCII format and is hereby incorporated by reference in its entirety. Said ASCII copy, created on Jun. 7, 2022, is named MRT-1102US5_ST25.txt and is 13 kilobytes in size.

BACKGROUND OF THE INVENTION

Messenger RNA therapy is becoming an increasingly important approach for the treatment of a variety of diseases. Messenger RNA therapy involves administration of messenger RNA (mRNA) into a patient in need of the therapy and production of the protein encoded by the mRNA within the patient body. Thus, it is important to ensure the production of highly pure and safe mRNA product. Traditionally, RNA purification typically employs spin columns and involves the use of caustic or flammable solvents, such as ethanol, which is undesirable for therapeutic administration and large scale production.

SUMMARY OF THE INVENTION

The present invention provides improved methods of purifying mRNA that is suitable for administration as a pharmaceutical product based on tangential flow filtration (TFF). Prior to the present invention, RNA purification typically employs spin columns and involves the use of caustic or flammable solvents, such as ethanol, which is undesirable for therapeutic administration and large scale production. Further, the prior art method typically does not allow for the separation of incomplete transcripts known as premature aborts or "shortmers," which is reported to be highly immunostimulatory and the presence of which may greatly alter the toxicity and tolerability profile of mRNA as active pharmaceutical ingredient (API). The present invention is, in part, based on the discovery that tangential flow filtration is surprisingly effective to remove reactants, enzymes, by products, in particular, the shortmers, from mRNA production mixture. As described herein, tangential flow filtration, particularly in combination with a pre-treatment using a denaturing agent, can effectively remove reactants, enzymes and byproducts including prematurely aborted RNA sequences (i.e., shortmers), while still maintaining the integrity of mRNA. More surprisingly, the present inventors have demonstrated that tangential flow filtration can be successfully performed using only aqueous buffers as solvents without using any caustic or flammable solvents. Thus, the present invention provides a more effective, reliable, and safer method of purifying mRNA from large scale manufacturing process therapeutic applications.

In one aspect, the present invention provides, among other things, methods of purifying messenger RNA (mRNA) including the steps of (a) subjecting an impure preparation comprising in vitro synthesized mRNA to a denaturing condition, and (b) purifying the mRNA from the impure preparation from step (a) by tangential flow filtration, wherein the mRNA purified from step (b) is substantially free of prematurely aborted RNA sequences and/or enzyme reagents used in in vitro synthesis.

In some embodiments, step (a) comprises adding a protein denaturing agent to the impure preparation. In some embodiments, step (a) comprises incubating the impure preparation with the protein denaturing agent added at room temperature for about 1-10 minutes (e.g., about 2-9, 2-8, 2-7, 3-10, 3-9, 3-8, 3-7, 3-6, 4-10, 4-9, 4-8, 4-7, 4-6 minutes). In some embodiments, step (a) comprises incubating the impure preparation with the protein denaturing agent added at room temperature for about 1, 2, 3, 4, 5, 6, 7, 8, 9, or 10 minutes. In some embodiments, step (a) comprises incubating the impure preparation with the protein denaturing agent added at room temperature for about 5 minutes. In some embodiments, a suitable protein denaturing agent is selected from the group consisting of urea, guanidinium thiocyanate, KCl, sodium dodecyl sulfate, sarcosyl, other detergents, and combinations thereof.

In some embodiments, step (a) comprises adding urea to the impure preparation to achieve a resulting urea concentration of about 1 M or greater. In some embodiments, the resulting urea concentration is about 2 M or greater, 3 M or greater, 4 M or greater, 5 M or greater, 6 M or greater, 7 M or greater, 8 M or greater, 9 M or greater, or 10 M or greater.

In some embodiments, step (a) comprises adding guanidinium thiocyanate to the impure preparation to achieve a resulting guanidinium thiocyanate concentration of about 1 M or greater. In some embodiments, the resulting guanidinium thiocyanate concentration is about 2 M or greater, 3 M or greater, 4 M or greater, 5 M or greater, 6 M or greater, 7 M or greater, 8 M or greater, 9 M or greater, or 10 M or greater.

In some embodiments, step (a) comprises adding KCl to the impure preparation to achieve a resulting KCl concentration of about 1 M or greater. In some embodiments, the resulting KCl concentration is about 2 M or greater, 3 M or greater, 4 M or greater, or 5 M or greater.

In some embodiments, the tangential flow filtration is performed using only aqueous solvents. In some embodiments, the tangential flow filtration is performed using water as solvent. In some embodiments, the tangential flow filtration is performed at a feed rate of approximately 100-200 mL/minute (e.g., approximately 100-180 mL/minute, 100-160 mL/minute, 100-140 mL/minute, 110-190 mL/minute, 110-170 mL/minute, or 110-150 mL/minute) and/or a flow rate of approximately 10-50 mL/minute (e.g., approximately 10-40 mL/minute, 10-30 mL/minute, 20-50 mL/minute, or 20-40 mL/minute). In some embodiments, the tangential flow filtration is performed at a feed rate of approximately 100, 110, 120, 130, 140, 150, 160, 170, 180, 190, or 200 mL/minute and/or a flow rate of approximately 10, 20, 30, 40, or 50 mL/minute.

In some embodiments, the mRNA purified from step (b) contains less than about 5% (e.g., less than about 4%, 3%, 2%, or 1%) of prematurely aborted RNA sequences and/or enzyme reagents used in in vitro synthesis. In some embodiments, the mRNA purified from step (b) contains less than about 1% (e.g., less than about 0.9%, 0.8%, 0.7%, 0.6%, 0.5%, 0.4%, 0.3%, 0.2%, or 0.1%) of prematurely aborted RNA sequences and/or enzyme reagents used in in vitro synthesis. In some embodiments, the mRNA purified from step (b) contains less than 0.5% of prematurely aborted RNA sequences and/or enzyme reagents used in in vitro synthesis. In some embodiments, the mRNA purified from step (b) contains less than 0.1% of prematurely aborted RNA sequences and/or enzyme reagents used in in vitro synthesis. In some embodiments, the mRNA purified from step (b) contains undetectable prematurely aborted RNA sequences and/or enzyme reagents used in in vitro synthesis as determined by ethidium bromide and/or Coomassie staining.

In some embodiments, the prematurely aborted RNA sequences comprise less than 15 bases (e.g., less than 14, 13, 12, 11, 10, 9 or 8 bases). In some embodiments, the prematurely aborted RNA sequences comprise about 8-12 bases.

In some embodiments, the enzyme reagents used in in vitro synthesis comprise T7 RNA polymerase, DNAse I, pyrophosphatase, and/or RNAse inhibitor. In some embodiments, the enzyme reagents used in in vitro synthesis comprise T7 RNA polymerase.

In some embodiments, the tangential flow filtration is performed before a cap and poly-A tail are added to the in vitro synthesized mRNA. In some embodiments, the tangential flow filtration is performed after a cap and poly-A tail are added to the in vitro synthesized mRNA. In some embodiments, the tangential flow filtration is performed both before and after a cap and poly-A tail are added to the in vitro synthesized mRNA.

In some embodiments, the in vitro synthesized mRNA is greater than about 1 kb, 1.5 kb, 2 kb, 2.5 kb, 3 kb, 3.5 kb, 4 kb, 4.5 kb, or 5 kb in length. In some embodiments, the in vitro synthesized mRNA comprises one or more modifications to enhance stability. In some embodiments, the one or more modifications are selected from modified nucleotide, modified sugar phosphate backbones, 5' and/or 3' untranslated region. In some embodiments, the in vitro synthesized mRNA is unmodified.

In some embodiments, the mRNA purified from step (b) has an integrity greater than about 95% (e.g., greater than about 96%, 97%, 98%, 99% or more). In some embodiments, the mRNA purified from step (b) has an integrity greater than 98%. In some embodiments, the mRNA purified from step (b) has an integrity greater than 99%. In some embodiments, the mRNA purified from step (b) has an integrity of approximately 100%.

The present invention also provides methods for manufacturing messenger RNA (mRNA) including the steps of synthesizing mRNA in vitro, and purifying the in vitro synthesized mRNA according to methods described herein.

The present invention also provides messenger RNA (mRNA) purified according to the methods described herein.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The following figures are for illustration purposes only and not for limitation.

DEFINITIONS

Figure 1:
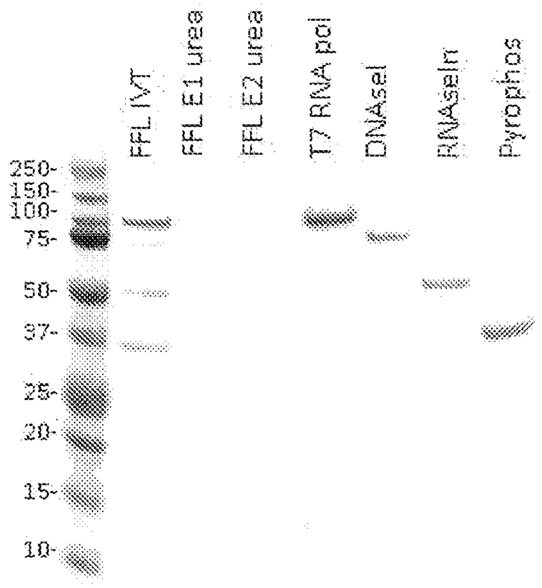
FIG. 1 shows exemplary protein levels in in vitro transcription of FFL mRNA samples purified according to provided methods, including exposure to urea, along with various controls as shown by gel electrophoresis and Coomassie staining.

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Expression: As used herein, "expression" of a nucleic acid sequence refers to translation of an mRNA into a polypeptide (e.g., heavy chain or light chain of antibody), assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and grammatical equivalent, are used inter-changeably.

Functional: As used herein, a "functional" biological molecule is a biological molecule in a form in which it exhibits a property and/or activity by which it is characterized.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as contaminants.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions.

mRNA integrity: As used herein, the term "mRNA integrity" generally refers to the quality of mRNA. In some embodiments, mRNA integrity refers to the percentage of mRNA that is not degraded after a purification process (e.g., tangential flow filtration). mRNA integrity may be determined using methods well known in the art, for example, by RNA agarose gel electrophoresis (e.g., Ausubel et al., John Weley & Sons, Inc., 1997, Current Protocols in Molecular Biology).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Prematurely aborted RNA sequences: The term "prematurely aborted RNA sequences", as used herein, refers to incomplete products of an mRNA synthesis reaction (e.g., an in vitro synthesis reaction). For a variety of reasons, RNA polymerases do not always complete transcription of a DNA template; i.e., RNA synthesis terminates prematurely. Possible causes of premature termination of RNA synthesis include quality of the DNA template, polymerase terminator sequences for a particular polymerase present in the template, degraded buffers, temperature, depletion of ribonucleotides, and mRNA secondary structures. Prematurely aborted RNA sequences may be any length that is less than the intended length of the desired transcriptional product. For example, prematurely aborted mRNA sequences may be less than 1000 bases, less than 500 bases, less than 100 bases, less than 50 bases, less than 40 bases, less than 30 bases, less than 20 bases, less than 15 bases, less than 10 bases or fewer.

Salt: As used herein the term "salt" refers to an ionic compound that does or may result from a neutralization reaction between an acid and a base.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially free: As used herein, the term "substantially free" refers to a state in which relatively little or no amount of a substance to be removed (e.g., prematurely aborted RNA sequences) are present. For example, "substantially free of prematurely aborted RNA sequences" means the prematurely aborted RNA sequences are present at a level less than approximately 5%, 4%, 3%, 2%, 1.0%, 0.9%, 0.8%, 0.7%, 0.6%, 0.5%, 0.4%, 0.3%, 0.2%, 0.1% or less (w/w) of the impurity. Alternatively, "substantially free of prematurely aborted RNA sequences" means the prematurely aborted RNA sequences are present at a level less than about 100 ng, 90 ng, 80 ng, 70 ng, 60 ng, 50 ng, 40 ng, 30 ng, 20 ng, 10 ηg, 1 ηg, 500 ρg, 100 ρg, 50 ρg, 10 ρg, or less.

DETAILED DESCRIPTION

The present invention provides, among other things, improved methods for purifying mRNA from an impure preparation (e.g., in vitro synthesis reaction mixture) based on tangential flow filtration. In some embodiments, an inventive method according to the present invention includes steps of (a) subjecting an impure preparation comprising in vitro synthesized mRNA to a denaturing condition, and (b) purifying the mRNA from the impure preparation from step (a) by tangential flow filtration, wherein the mRNA purified from step (b) is substantially free of prematurely aborted RNA sequences and/or enzyme reagents used in in vitro synthesis.

Various aspects of the invention are described in detail in the following sections. The use of sections is not meant to limit the invention. Each section can apply to any aspect of the invention. In this application, the use of "or" means "and/or" unless stated otherwise.

Synthesis of mRNA mRNA is typically thought of as the type of RNA that carries information from DNA to the ribosome. The existence of mRNA is typically very brief and includes processing and translation, followed by degradation. Typically, in eukaryotic organisms, mRNA processing comprises the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this "tail" serves to protect the mRNA from exonuclease degradation. Messenger RNA is translated by the ribosomes into a series of amino acids that make up a protein.

mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse 1, pyrophosphatase, and/or RNAse inhibitor. The exact conditions will vary according to the specific application. The presence of these reagents is undesirable in the final product according to several embodiments and may thus be referred to as impurities and a preparation containing one or more of these impurities may be referred to as an impure preparation.

mRNAs according to the present invention may be purified on a commercial scale. In some embodiments, the mRNA is purified at a scale of or greater than 0.1 grams, 0.5 grams, 1 gram, 2 grams, 3 grams, 4 grams, 5 grams, 6 grams, 7 grams, 8 grams, 9 grams, 10 gram, 20 grams, 30 grams, 40 grams, 50 grams, 60 grams, 70 grams, 80 grams, 90 grams, 100 grams, 200 grams, 300 grams, 400 grams, 500 grams, 600 grams, 700 grams, 800 grams, 900 grams, or 1,000 grams per batch.

According to various embodiments, the present invention may be used to purify in vitro synthesized mRNA of a variety of lengths. In some embodiments, the present invention may be used to purify in vitro synthesized mRNA of greater than about 1 kb, 1.5 kb, 2 kb, 2.5 kb, 3 kb, 3.5 kb, 4 kb, 4.5 kb, 5 kb, 6 kb, 7 kb, 8 kb, 9 kb, 10 kb, 11 kb, 12 kb, 13 kb, 14 kb, or 15 kb in length. In some embodiments, the present invention may be used to purify mRNA containing one or more modifications that typically enhance stability. In some embodiments, one or more modifications are selected from modified nucleotide, modified sugar phosphate backbones, 5' and/or 3' untranslated region. In some embodiments, the present invention may be used to purify in vitro synthesized mRNA that is unmodified.

Typically, mRNAs are modified to enhance stability. Modifications of mRNA can include, for example, modifications of the nucleotides of the RNA. An modified mRNA according to the invention can thus include, for example, backbone modifications, sugar modifications or base modifications. In some embodiments, antibody encoding mRNAs (e.g., heavy chain and light chain encoding mRNAs) may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

While mRNA provided from in vitro transcription reactions may be desirable in some embodiments, other sources of mRNA are contemplated as within the scope of the invention including wild-type mRNA produced from bacteria, fungi, plants, and/or animals.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

The present invention may be used to purify mRNAs encoding a variety of proteins. Non-limiting examples of purification of mRNAs encoding firefly luciferase, Factor IX, and CFTR, are described in detail in the Examples section.

Denaturing Conditions and Denaturation Agents

Typically, changing the conformation of a protein or nucleic acid either temporarily or permanently by disrupting intermolecular forces is called denaturation. Denaturation results in structural change and often to a loss of activity. Since the native conformation of a molecule is usually the most water soluble, disrupting the secondary and tertiary structures of a molecule may cause changes in solubility and may result in precipitation of the protein or nucleic acid from solution. Surprisingly, as described herein, using a denaturing condition in combination with tangential flow filtration (TFF) can facilitate mRNA purification while still maintaining the integrity of mRNA.

As used herein, the term "denaturing condition" refers to any chemical or physical conditions that can cause denaturation. Exemplary denaturing conditions include, but are not limited to, chemical reagents, high temperatures, extreme pH, etc.

In some embodiments, a denaturing condition is achieved through adding one or more denaturing agents to an impure preparation containing mRNA to be purified. In some embodiments, a denaturing agent suitable for the present invention is a protein and/or DNA denaturing agent. In some embodiments, a denaturing agent may be: 1) an enzyme (such as a serine proteinase or a DNase), 2) an acid, 3) a solvent, 4) a cross-linking agent, 5) a chaotropic agent, 6) a reducing agent, and/or 7) high ionic strength via high salt concentrations. In some embodiments, a particular agent may fall into more than one of these categories.

In some embodiments, one or more enzymes may be used as denaturing agents to degrade proteins and DNA templates used in mRNA synthesis. In some embodiments, suitable enzymes include, but are not limited to, serine proteases such as chymotrypsin and chymotrypsin-like serine proteases, trypsin and trypsin-like serine proteases, elastase and elastase-like serine proteases, subtilisin and subtilisin-like serine proteases, and combinations thereof, deoxyribonucleases (DNases) such as deoxyribonuclease 1, 11 and/or IV, restriction enzymes such as EcoRI, EcoRII, BamHI, HindIII, SpeI, SphI, StuI, XbaI, and combination thereof.

In some embodiments, an acid may be used as a denaturing agent. In some embodiments, a suitable acid may be acetic acid, formic acid, oxalic acid, citric acid, benzoic acid, chloroacetic acid, dichloroacetic acid, trichloroacetic acid, ascorbic acid, sulfosalicylic acid, and combinations thereof.

In some embodiments, a solvent may be used as a denaturing agent. In some embodiments, a solvent may be isopropyl alcohol, acetone, methyl ethyl ketone, methyl isobutyl ketone, ethanol, methanol, denatonium, and combinations thereof.

In some embodiments, a chaotropic agent may be sued as a denaturing agent. Choatropic agents are substances which disrupt the structure of macromolecules such as proteins and nucleic acids by interfering with non-covalent forces such as hydrogen bonds and van der Waals forces. In some embodiments, a chaotropic agent may be urea, thiourea, guanidinium chloride, guanidinium thiocyanate, guanidinium isothiocyanate, lithium acetate, magnesium chloride, sodium dodecyl sulfate, lithium perchlorate and combination thereof.

In some embodiments, an impure preparation containing mRNA to be purified is treated with urea. In some embodiments, an amount of urea is added such that the resulting urea concentration is about 1M or greater. In some embodiments, urea is added such that the resulting urea concentration is about 2 M or greater, 3 M or greater, 4 M or greater, 5 M or greater, 6 M or greater, 7 M or greater, 8 M or greater, 9 M or greater, or 10 M or greater. In some embodiments, an impure preparation containing mRNA to be purified is treated with guanidinium thiocyanate. In some embodiments, an amount of guanidinium thiocyanate is added such that the resulting guanidinium thiocyanate concentration is about 1M or greater. In some embodiments, guanidinium thiocyanate is added such that the resulting guanidinium thiocyanate concentration is about 2 M or greater, 3 M or greater, 4 M or greater, 5 M or greater, 6 M or greater, 7 M or greater, 8 M or greater, 9 M or greater, or 10 M or greater.

In some embodiments, a reducing agent may be used as a denaturing agent. Reducing agents are compounds that donate an electron to another species, thus becoming oxidized itself. In some embodiments, a reducing agent may be lithium aluminum hydride, sodium amalgam, diborane, sodium borohydride, sulfites, diisobutylaluminum hydride, phosphites, carbon monoxide, 2-mercaptoethanol, dithiothreitol, or tris(2-carboxyethyl)phosphine, and combinations thereof.

In some embodiments, one or more of pH, heat, and/or heavy metals (such as lead, mercury or cadmium) may also be used a denaturing agents. Extremes of pH are known to cause a protein to denature. Although the backbone of a protein chain is neutral, the amino acid residues that comprise the protein often contain acidic and basic groups. These groups are usually charged and can form salt bridges with a group of opposite charge. Accordingly, extremes of pH can change the charges on these acidic and basic groups, disrupting salt bridges.

In some embodiments, less drastic changes in pH may also affect the activity and solubility of a protein. Like individual amino acids, proteins have an isoelectric point at which the number of negative charges equals the number of positive charges. This is frequently the point of minimum water solubility. At the isoelectric pH, there is no net charge on the molecule. Individual molecules have a tendency to approach one another, coagulate, and precipitate out of solution. At a pH above or below the isoelectric pH, the molecules have a net negative or positive charge, respectively. Thus when protein molecules approach each other, they have the same overall charge and repulse each other.

In some embodiments, heat may be used as a denaturing agent. Heat can supply kinetic energy to protein molecules, causing their atoms to vibrate more rapidly. In some embodiments, this will disrupt relatively weak forces such as hydrogen bonds and hydrophobic interactions. Heat is also used in sterilization to denature and hence destroy the enzymes in bacteria.

In some embodiments, salts of metal ions such as mercury (II), lead(II), and silver may be used as denaturing agents due to their ability to form strong bonds with disulfide groups and with the carboxylate ions of the acidic amino acids. Thus, they disrupt both disulfide bridges and salt linkages and cause the protein to precipitate out of solution as an insoluble metal-protein salt.

In some embodiments, high concentrations of salt (high salinity) may also be used as a denaturing agent. High concentrations of salts are known to cause both proteins and nucleic acids to precipitate from an aqueous solution. In some embodiments, a high concentration of salt may be between 1M and 10 M, inclusive. In some embodiments, a high concentration of salt may be between 2M and 9M, inclusive. In some embodiments, a high concentration of salt may be between 2M and 8M, inclusive. In some embodiments, a high concentration of salt may be between 2M and 5M, inclusive. In some embodiments, a high concentration of salt may be greater than 1M concentration. In some embodiments, a high concentration of salt may be greater than 2M concentration. In some embodiments, a high concentration of salt may be greater than 3M concentration. In some embodiments, a high concentration of salt may be greater than 4M concentration. In some embodiments, a high concentration of salt may be greater than 5M concentration. In some embodiments, a high concentration of salt may be greater than 6M concentration. In some embodiments, a high concentration of salt may be greater than 7M concentration. In some embodiments, a high concentration of salt may be greater than 8M concentration. In some embodiments, a single salt is used as a denaturing agent. In some embodiments, more than one salt is used as a denaturing agent.

In some embodiments, a salt used as a denaturing agent may be a calcium salt, an iron salt, a magnesium salt, a potassium salt, a sodium salt, or a combination thereof. Exemplary specific salts suitable for use as denaturing agents in some embodiments include, but are not limited to, potassium chloride (KCl), sodium chloride (NaCl), lithium chloride (LiCl), calcium chloride ($CaCl_2$), potassium bromide (KBr), sodium bromide (NaBr), lithium bromide (LiBr). In some embodiments, the denaturing agent the impure preparation is subjected to is potassium chloride (KCl). In some embodiments, KCl is added such that the resulting KCl concentration is about 1M or greater. In some embodiments, KCl is added such that the resulting KCl concentration is about 2 M or greater, 3 M or greater, 4 M or greater, or 5 M or greater.

In some embodiments, it may be desirable to incubate the impure preparation with one or more denaturing agents for a period of time. In some embodiments, the impure preparation is incubated with a denaturing agent for less than one minute. In some embodiments, the impure preparation is incubated with a denaturing agent for one minute. In some embodiments, the impure preparation is incubated with a denaturing agent for two minutes. In some embodiments, the impure preparation is incubated with a denaturing agent for three minutes. In some embodiments, the impure preparation is incubated with a denaturing agent for four minutes. In some embodiments, the impure preparation is incubated with a denaturing agent for five minutes. In some embodiments, the impure preparation is incubated with a denaturing agent for ten minutes. In some embodiments, the impure preparation is incubated with a denaturing agent for one hour. In some embodiments, the impure preparation is incubated with a denaturing agent for two hours.

In some embodiments, the impure preparation is incubated with one or more denaturing agents at room temperature (e.g., about 20-25° C.). In some embodiments, the impure preparation is incubated with one or more denaturing agents at a temperature below room temperature. In some embodiments, the impure preparation is incubated with one or more denaturing agents at a temperature above room temperature.

Purification

In several embodiments, before and/or after exposure to a denaturing condition, tangential flow filtration is used to purify the mRNA from an impure preparation. In some embodiments, tangential flow filtration is performed before a cap and poly-A tail are added to the in vitro synthesized mRNA. In some embodiments, tangential flow filtration is performed after a cap and poly-A tail are added to the in vitro synthesized mRNA. In some embodiments, tangential flow filtration is performed both before and after a cap and poly-A tail are added to the in vitro synthesized mRNA.

Traditional Membrane Filtration

Generally, membrane filtration involves separating solids from fluids using one or more interposed permeable membranes. Membrane filtration may also be used to filter particles from a gaseous sample. There are two major forms of membrane filtration, passive filtration which proceeds solely due to solution-diffusion, and active filtration which uses positive pressure or negative pressure (i.e. vacuum) to force the liquid or gas across the membrane.

Traditional membrane filtration is also known as "dead-end" filtration. In this format, the feed is loaded onto a membrane and forced through by positive or negative pressure. Dead-end filtration tends to be inexpensive and simple, with the major drawbacks being fouling or clogging of the membrane with non- or slowly-permeating solute (also referred to as the retentate), and concentration polarization. Generally, membranes tend to clog or foul more rapidly as driving forces increase. As a membrane fouls or clogs, the rate of filtration is reduced and eventually no permeate is able to pass through until the filter is changed or cleaned. Concentration polarization is a phenomenon wherein non-permeable solute collects on the surface of a filter and eventually forms a type of secondary membrane, which further impedes travel of permeable solute across the membrane. As a result, dead-end filtration is typically used in batch type processes.

Tangential Flow Filtration

Tangential flow filtration (TFF), also referred to as cross-flow filtration, is a type of filtration wherein the material to be filtered is passed tangentially across a filter rather than through it. In TFF, undesired permeate passes through the filter, while the desired retentate passes along the filter and is collected downstream. It is important to note that the desired material is typically contained in the retentate in TFF, which is the opposite of what one normally encounters in traditional-dead end filtration.

Depending upon the material to be filtered, TFF is usually used for either microfiltration or ultrafiltration. Microfiltration is typically defined as instances where the filter has a pore size of between 0.05 μm and 1.0 μm, inclusive, while ultrafiltration typically involves filters with a pore size of less than 0.05 μm. Pore size also determines the nominal molecular weight limits (NMWL), also referred to as the molecular weight cut off (MWCO) for a particular filter, with microfiltration membranes typically having NMWLs of greater than 1,000 kilodaltons (kDa) and ultrafiltration filters having NMWLs of between 1 kDa and 1,000 kDa.

A principal advantage of tangential flow filtration is that non-permeable particles that may aggregate in and block the filter (sometimes referred to as "filter cake") during traditional "dead-end" filtration, are instead carried along the surface of the filter. This advantage allows tangential flow filtration to be widely used in industrial processes requiring continuous operation since down time is significantly reduced because filters do not generally need to be removed and cleaned.

Tangential flow filtration can be used for several purposes including concentration and diafiltration, among others. Concentration is a process whereby solvent is removed from a solution while solute molecules are retained. In order to effectively concentrate a sample, a membrane having a NMWL or MWCO that is substantially lower than the molecular weight of the solute molecules to be retained is used. Generally, one of skill may select a filter having a NMWL or MWCO of three to six times below the molecular weight of the target molecule(s).

Diafiltration is a fractionation process whereby small undesired particles are passed through a filter while larger desired molecules are maintained in the retentate without changing the concentration of those molecules in solution. Diafiltration is often used to remove salts or reaction buffers from a solution. Diafiltration may be either continuous or discontinuous. In continuous diafiltration, a diafiltration solution is added to the sample feed at the same rate that filtrate is generated. In discontinuous diafiltration, the solution is first diluted and then concentrated back to the starting concentration. Discontinuous diafiltration may be repeated until a desired concentration of the solute molecules is reached.

At least three process variables that are important in a typical TFF process: the transmembrane pressure, feed rate, and flow rate of the permeate. The transmembrane pressure is the force that drives fluid through the filter, carrying with it permeable molecules. In some embodiments, the transmembrane pressure is between 1 and 30 pounds per square inch (psi), inclusive.

The feed rate (also known as the crossflow velocity) is the rate of the solution flow through the feed channel and across the filter. The feed rate determines the force that sweeps away molecules that may otherwise clog or foul the filter and thereby restrict filtrate flow. In some embodiments, the feed rate is between 50 and 500 mL/minute. In some embodiments, the feed rate is between 50 and 400 mL/minute. In some embodiments, the feed rate is between 50 and 300 mL/minute. In some embodiments, the feed rate is between 50 and 200 mi/minute. In some embodiments, the feed rate is between 75 and 200 mL/minute. In some embodiments, the feed rate is between 100 and 200 mi/minute. In some embodiments, the feed rate is between 125 and 175 mL/minute. In some embodiments, the feed rate is 130 mL/minute. In some embodiments, the feed rate is between 60 mL/min and 220 mL/min. In some embodiments, the feed rate is 60 mL/min or greater. In some embodiments, the feed rate is 100 mL/min or greater. In some embodiments, the feed rate is 150 mL/min or greater. In some embodiments, the feed rate is 200 mL/min or greater. In some embodiments, the feed rate is 220 mL/min or greater.

The flow rate of the permeate is the rate at which the permeate is removed from the system. For a constant feed rate, increasing permeate flow rates can increase the pressure across the filter, leading to enhanced filtration rates while also potentially increasing the risk of filter clogging or fouling. The principles, theory, and devices used for TFF are described in Michaels et al., "Tangential Flow Filtration" in Separations Technology, Pharmaceutical and Biotechnology Applications (W. P. Olson, ed., Interpharm Press, Inc., Buffalo Grove, Ill. 1995). See also U.S. Pat. Nos. 5,256,294 and 5,490,937 for a description of high-performance tangential flow filtration (HP-TFF), which represents an improvement to TFF. In some embodiments, the flow rate is between 10 and 100 mL/minute. In some embodiments, the flow rate is between 10 and 90 mL/minute. In some embodiments, the flow rate is between 10 and 80 mL/minute. In some embodiments, the flow rate is between 10 and 70 mL/minute. In some embodiments, the flow rate is between 10 and 60 mL/minute. In some embodiments, the flow rate is between 10 and 50 mL/minute. In some embodiments, the flow rate is between 10 and 40 mL/minute. In some embodiments, the flow rate is between 20 and 40 mL/minute. In some embodiments, the flow rate is 30 mL/minute.

Any combinations of various process variables described herein may be used. In some embodiments, the tangential flow filtration is performed at a feed rate of approximately 100-200 mL/minute (e.g., approximately 100-180 mL/minute, 100-160 mL/minute, 100-140 mL/minute, 110-190 mL/minute, 110-170 mL/minute, or 110-150 mL/minute) and/or a flow rate of approximately 10-50 mL/minute (e.g., approximately 10-40 mL/minute, 10-30 mL/minute, 20-50 mL/minute, or 20-40 mL/minute). In some embodiments, the tangential flow filtration is performed at a feed rate of approximately 100, 110, 120, 130, 140, 150, 160, 170, 180, 190, or 200 mL/minute and/or a flow rate of approximately 10, 20, 30, 40, or 50 mL/minute.

Further flow rates to accommodate large (commercial) scale purification would entail the tangential flow filtration being performed at a feed rate of approximately 10 L-200 L/minute. (e.g., approximately 10-180 L/minute, 100-160 L/minute, 100-140 L/minute, 110-190 L/minute, 110-170 L/minute, or 110-150 L/minute) and/or a flow rate of approximately 10-50 L/minute (e.g., approximately 10-40 L/minute, 10-30 L/minute, 20-50 L/minute, or 20-40 L/minute). In some embodiments, the tangential flow filtration is performed at a feed rate of approximately 100, 110, 120, 130, 140, 150, 160, 170, 180, 190, or 200 L/minute and/or a flow rate of approximately 10, 20, 30, 40, or 50 L/minute.

As described above, filters used in TFF may have any of a variety of pore sizes, and thus NMWLs. In some embodiments, a filter will have a NMWL of between 100 kDa and 1,000 kDa. In some embodiments, a filter will have a NMWL of between 200 kDa and 700 kDa. In some embodiments, a filter will have a NMWL between 200 kDa and 500 kDa. In some embodiments, a filter has a NMWL of 300 kDa. In some embodiments, a filter has a NMWL of 500 kDa.

In some embodiments, a tangential flow filtration according to the invention is performed using only aqueous solvents. In some embodiments, a tangential flow filtration according to the invention is performed using water as the solvent.

Characterization of Purified mRNA

In various embodiments, mRNA purified according to the present invention is substantially free of impurities from mRNA synthesis process including, but not limited to, prematurely aborted RNA sequences, DNA templates, and/or enzyme reagents used in in vitro synthesis.

A particular advantage provided by the present invention is the ability to remove or eliminate a high degree of prematurely aborted RNA sequences (also known as "shortmers"). In some embodiments, a method according to the invention removes more than about 90%, 95%, 96%, 97%, 98%, 99% or substantially all prematurely aborted RNA sequences. In some embodiments, mRNA purified according to the present invention is substantially free of prematurely aborted RNA sequences. In some embodiments, mRNA purified according to the present invention contains less than about 5% (e.g., less than about 4%, 3%, 2%, or 1%) of prematurely aborted RNA sequences. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of prematurely aborted RNA sequences. In some embodiments, mRNA purified according to the present invention contains undetectable prematurely aborted RNA sequences as determined by, e.g., ethidium bromide and/or Coomassie staining. In some embodiments, prematurely aborted RNA sequences comprise less than 15 bases (e.g., less than 14, 13, 12, 11, 10, 9 or 8 bases). In some embodiments, the prematurely aborted RNA sequences comprise about 8-12 bases.

In some embodiments, a method according to the present invention removes or eliminates a high degree of enzyme reagents used in in vitro synthesis including, but not limited to, T7 RNA polymerase, DNAse I, pyrophosphatase, and/or RNAse inhibitor. In some embodiments, the present invention is particularly effective to remove T7 RNA polymerase. In some embodiments, a method according to the invention removes more than about 90%, 95%, 96%, 97%, 98%, 99% or substantially all enzyme reagents used in in vitro synthesis including. In some embodiments, mRNA purified according to the present invention is substantially free of enzyme reagents used in in vitro synthesis including. In some embodiments, mRNA purified according to the present invention contains less than about 5% (e.g., less than about 4%, 3%, 2%, or 1%) of enzyme reagents used in in vitro synthesis including. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of enzyme reagents used in in vitro synthesis including. In some embodiments, mRNA purified according to the present invention contains undetectable enzyme reagents used in in vitro synthesis including as determined by, e.g., ethidium bromide and/or Coomassie staining.

In various embodiments, mRNA purified using a method described herein maintain high degree of integrity. As used herein, the term "mRNA integrity" generally refers to the quality of mRNA after purification. In some embodiments, mRNA integrity refers to the percentage of mRNA that is not degraded after tangential flow filtration. mRNA integrity may be determined using methods well known in the art, for example, by RNA agarose gel electrophoresis (e.g., Ausubel et al., John Weley & Sons, Inc., 1997, Current Protocols in Molecular Biology). In some embodiments, mRNA purified according to the present invention has an integrity greater than about 95% (e.g., greater than about 96%, 97%, 98%, 99% or more). In some embodiments, mRNA purified according to the present invention has an integrity greater than 98%. In some embodiments, mRNA purified according to the present invention has an integrity greater than 99%. In some embodiments, mRNA purified according to the present invention has an integrity of approximately 100%.

EXAMPLES

Example 1. Generation and Purification of Messenger RNA (mRNA)

Synthesis of mRNA

In each of the examples below, the synthesis of mRNA was conducted under complete RNAse-free conditions. All tubes, vials, pipette tips, pipettes, buffers, etc. were required to be nuclease-free, unless explicitly stated otherwise.

In the following examples, unless otherwise described, mRNA was synthesized via in-vitro transcription from a linearized DNA template. To produce the desired mRNA pre-cursor (IVT) construct, a mixture of ~100 ug of linearized DNA, rNTPs (3.33 mM), DTT (10 mM), T7 RNA polymerase, RNAse Inhibitor, Pyrophosphatase and reaction buffer (10×, 800 mM Hepes (pH8.0), 20 mM Spermidine, 250 mM $MgCl_2$, pH 7.7) was prepared with RNase-free water to a final volume of 2.24 mL. The reaction mixture is incubated at 37° C. for a range of time between 20 minutes-120 minutes. Upon completion, the mixture is treated with DNase I for an additional 15 minutes and quenched accordingly.

Addition of 5' Cap and 3' Tail

The purified mRNA product from the aforementioned IVT step (and possibly initial TFF filtration as well) was denatured at 65° C. for 10 minutes. Separately, portions of GTP (20 mM), S-adenosyl methionine, RNAse inhibitor, 2'-O-Methyltransferase and guanylyl transferase are mixed together with reaction buffer (10×, 500 mM Tris-HCl (pH8.0), 60 mM KCl, 12.5 mM $MgCl_2$) to a final concentration of 8.3 mL. Upon denaturation, the mRNA is cooled on ice and then added to the reaction mixture. The combined solution is incubated for a range of time at 37° C. for 20-90 minutes. Upon completion, aliquots of ATP (20 mM), PolyA Polymerase and tailing reaction buffer (10×, 500 mM Tris-HCl (pH8.0), 2.5M NaCl, 100 mM $MgCl_2$) are added and the total reaction mixture is further incubated at 37° C. for a range of time from 20-45 minutes. Upon completion, the final reaction mixture is quenched and purified accordingly.

Purification Via Tangential Flow Filtration

In the following examples, unless otherwise described, the tangential flow filtration (TFF) system consisted of a filtration membrane and a peristaltic pump (Millipore Labscale TFF system) with tangential circulation of the fluid across the membrane at a feed rate of ~130 mL/min with a 30 mL/min flow rate for the permeate. The TFF membrane employed was a MidiKros 500 kDa mPES 115 $cm^2$ (Spectrum Labs). Before use, the filter cartridge was washed with nuclease free water and further cleaned with 0.2N NaOH. Finally the system was cleaned with nuclease free water until the pH of permeate and retentate reached a pH ~6.

Example 2. Analysis of Purified mRNA

Testing for Presence of Enzymes in Purified mRNA

Unless otherwise described, standard Coomassie-stained protein gels were performed to determine the presence of any residual reagent enzymes present before and after purifications. In some instances, BCA assays were performed as well.

Assessment of mRNA Integrity Via Agarose Gel Electrophoresis Assays

Unless otherwise described, messenger RNA size and integrity were assessed via gel electrophoresis. Either self-poured 1.0% agarose gel or Invitrogen E-Gel precast 1.2% agarose gels were employed. Messenger RNA was loaded at 1.0-1.5 ug quantities per well. Upon completion, messenger RNA bands were visualized using ethidium bromide.

In Vitro mRNA Integrity Assays

Unless otherwise described, in vitro transfections of firefly luciferase mRNA were performed using HEK293T cells. Transfections of one microgram of each mRNA construct were performed in separate wells using lipofectamine. Cells were harvested at select time points (e.g. 4 hour, 8 hour, etc.) and respective protein production was analyzed. For FFL mRNA, cell lysates were analyzed for luciferase production via bioluminescence assays.

Bioluminescence Analysis

In examples including a fluorescent assessment of provided RNA, the bioluminescence assay was conducted using a Promega Luciferase Assay System (Item #E1500), unless otherwise specified. The Luciferase Assay Reagent was prepared by adding 10 mL of Luciferase Assay Buffer to Luciferase Assay Substrate and mix via vortex. Approximately 20 uL of homogenate samples were loaded onto a 96-well plate followed by 20 uL of plate control to each sample. Separately, 120 uL of Luciferase Assay Reagent (prepared as described above) was added to each well of a 96-well flat bottomed plate. Each plate was then inserted into the appropriate chambers using a Molecular Device Flex Station instrument and measure the luminescence (measured in relative light units (RLU)).

Example 3. Generation and Purification of Firefly Luciferase (FFL) Messenger RNA (mRNA)

This example illustrates that, according to various embodiments, a combination of tangential flow filtration (TFF) and a denaturing agent may be used according to provided methods to product a highly purified mRNA product. In this example, urea is used as the protein denaturing agent.

In this example, a five milligram batch of firefly luciferase (FFL) RNA (SEQ ID NO: 1, below) was transcribed via the in vitro methods described above to produce the aforementioned intermediate construct with no cap and no polyA tail. This reaction maintained a total volume of 2.24 mL and was quenched upon completion by an equivalent volume of 10M urea, bringing the final urea concentration to 5M. The resultant solution was incubated for five minutes at room temperature and transferred to the tangential flow filtration (TFF) system reservoir. The sample was diluted to 200 mL with nuclease free water and washed with 1200 mL nuclease free water by ultrafiltration of 200 mL at a time. Following this, the sample was treated with 200 mL 10 mM Sodium Citrate (pH 6.4) followed by 600 ml wash with nuclease free water. Finally the sample was concentrated to ~2 mL and the final concentration was determined via absorption at 260 nm ($\lambda_{max}$).

Codon-Optimized Firefly Luciferase (FFL) mRNA (SEQ ID NO: 1)

X$_2$AUGGAAGAUGCCAAAAACAUUAAGAAGGGCCCAGC
GCCAUUCUACCCACUCGAAGACGGGACCGCCGGCG
AGCAGCUGCACAAAGCCAUGAAGCGCUACGCCCUG
GUGCCCGGCACCAUCGCCUUUACCGACGCACAUAU
CGAGGUGGACAUUACCUACGCCGAGUACUUCGAGA
UGAGCGUUCGGCUGGCAGAAGCUAUGAAGCGCUAU
GGGCUGAAUACAAACCAUCGGAUCGUGGUGUGCAG
CGAGAAUAGCUUGCAGUUCUUCAUGCCCGUGUUGG
GUGCCCUGUUCAUCGGUGUGGCUGUGGCCCCAGCU
AACGACAUCUACAACGAGCGCGAGCUGCUGAACAG
CAUGGGCAUCAGCCAGCCCACCGUCGUAUUCGUGA
GCAAGAAAGGGCUGCAAAAGAUCCUCAACGUGCAA
AAGAAGCUACCGAUCAUACAAAAGAUCAUCAUCAU
GGAUAGCAAGACCGACUACCAGGGCUUCCAAAGCA
UGUACACCUUCGUGACUUCCCAUUUGCCACCCGGC
UUCAACGAGUACGACUUCGUGCCCGAGAGCUUCGA
CCGGGACAAAACCAUCGCCCUGAUCAUGAACAGUA
GUGGCAGUACCGGAUUGCCCAAGGGCGUAGCCCUA
CCGCACCGCACCGCUUGUGUCCGAUUCAGUCAUGC
CCGCGAGCCCAUCUUCGGCAACCAGAUCAUCCCCG
ACACCGCUAUCCUCAGGGUGGUGGCAUUUCACCAC
GGCUUCGGCAUCUUCACCACGCUGGGCUACUUGAU
CUGCGGCUUGCGGGUCGUGCUCAUGUACCGCUUCG
AGGAGGAGCUAUUCUUGCGCAGCUUGCAAGACUAU
AAGAUUCAAUCUGCCCUGCUGGUGCCCACACUAUU
UAGCUUCUUCGCUAAGAGCACUCUCAUCGACAAGU
ACGACCUAAGCAACUUGCACGAGAUCGCCAGCGGC
GGGGCGCCGCUCAGCAAGGAGGUAGGUGAGGCCGU
GGGCAAACGCUUCCACCUACCAGGCAUCCGCCAGG
GCUACGGCCUGACAGAAACAACCAGCGCCAUUCUG
AUCACCCCCGAAGGGGACGACAAGCCUGGCGCAGU
AGGCAAGGUGGUGCCCUUCUUCGAGGCUAAGGUGG
UGGACUUGGACACCGGUAAGACACUGGGUGUGAAC
CAGCGCGGCGAGCUGUGCGUCCGUGGCCCCAUGAU
CAUGAGGGGCUACGUUAACAACCCCGAGGCUACAA
ACGCUCUCAUCGACAAGGACGGGUGGCUGCACAGC
GGCGACAUCGCCUACUGGGACGAGGACGAGCACUU
CUUCAUCGUGGACCGGCUGAAGAGCCUGAUCAAAU
ACAAGGGCUACCAGGUAGCCCCAGCCGAACUGGAG
AGCAUCCUGCUGCAACACCCCAACAUCUUCGACGC

-continued

CGGGGUCGCCGGCCUGCCCGACGACGAUGCCGGCG
AGCUGCCCGCCGCAGUCGUCGUGCUGGAACACGGU
AAAACCAUGACCGAGAAGGAGAUCGUGGACUAUGU
GGCCAGCCAGGUUACAACCGCCAAGAAGCUGCGCG
GUGGUGUUGUGUUCGUGGACGAGGUGCCUAAAGGA
CUGACCGGCAAGUUGGACGCCCGCAAGAUCCGCGA
GAUUCUCAUUAAGGCCAAGAAGGGCGGCAAGAUCG
CCGUGUAY$_2$

5' and 3' UTR Sequences:

(SEQ ID NO: 2)

$X_2$ = GGGAUCCUACC (SEQ ID NO: 3)

$Y_2$ = UUUGAAUU

Approximately 5 mg of TFF-purified firefly luciferase RNA was capped and tailed in a final reaction volume of 9 mL, as described above. A portion of this reaction mixture (6.7 ml) was treated with 5M urea for 5 minutes at room temperature (RT) and purified using TFF. Approximately 1.5 mg of the cap/tail reaction mixture was purified via TFF using solely water and isolated. Separately, another small portion of the cap/tail reaction mixture was purified using a Qiagen RNeasy Purification kit according to published protocol. The three isolated final FFL mRNA batches were aliquoted and transfected into HEK293T cells as described below. Cell lysates were analyzed for the presence of FFL protein via fluorescence detection (FFL activity).

In this example, in order to remove reaction enzymes in this example, a portion of the FFL mRNA IVT reaction mixture was subjected to 10M urea resulting in a final concentration of 5M urea. This solution was incubated for five minutes at room temperature and then purified via TFF as described above. FIG. 1 shows a coomassie stained protein gel which shows the resulting mRNA isolated after TFF employing the aforementioned urea conditions. There is no detectable enzyme present upon completion.

Figure 2:
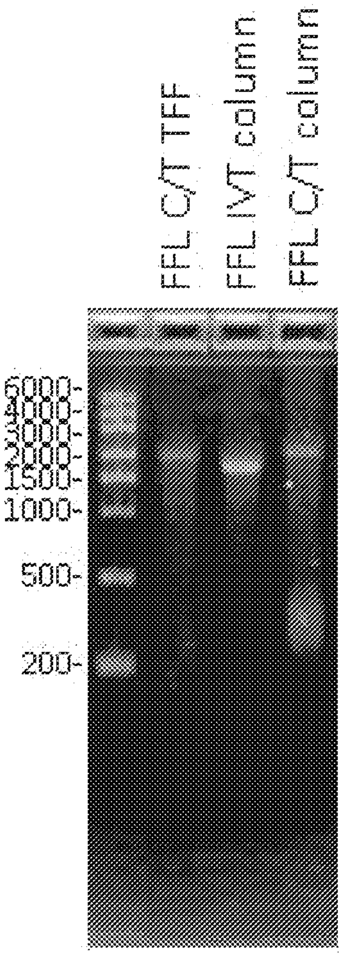
FIG. 2 shows exemplary firefly luciferase (FFL) mRNA levels in in vitro transcription samples purified according to provided methods as compared to mRNA purified according to traditional methods as shown by agarose gel electrophoresis and ethidium bromide staining.
Figure 3:
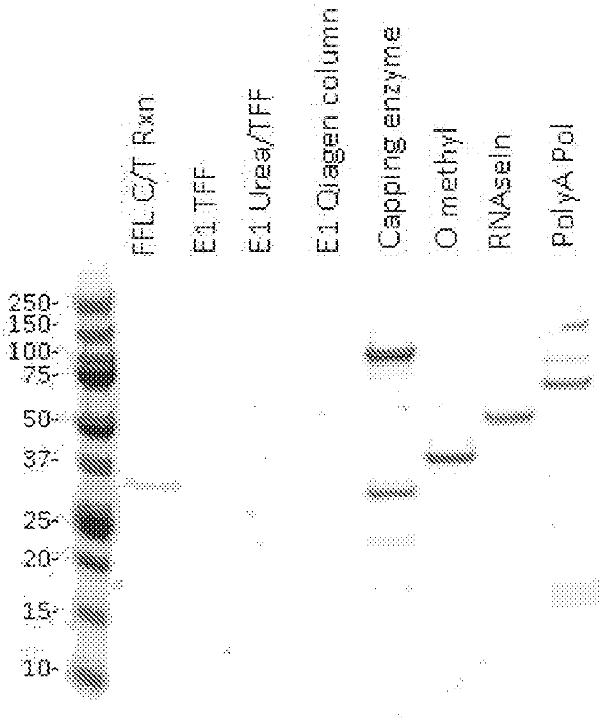
FIG. 3 shows exemplary protein levels in in vitro transcription samples of FFL mRNA purified according to provided methods, including TFF with and without exposure to 5M urea, as compared to mRNA purified according to traditional methods gel electrophoresis and Coomassie staining.

After producing the capped and tailed FFL mRNA product. TFF methods were employed further to purify the final target mRNA. Portions of the same cap/tail reaction mixture were separately aliquoted and purified either via TFF with no urea or via spin-column methods (Qiagen RNeasy Kit) for comparison. A comparison of the final mRNA isolated either by TFF or spin column was made using gel electrophoresis and is depicted in FIG. 2. Further, residual enzyme levels were monitored via protein gel (FIG. 3). In FIG. 2, one can clearly see the respective "IVT" FFL mRNA bands migrating at ~1900 nt with the capped & tailed (C/T) final mRNA approximately 2100 nt long. The "shortmer" band typically observed using spin-column isolation after the cap/tail step is indeed observed in Lane 4.

It is apparent that the shortmer band is not present after the cap/tail step when TFF-purified mRNA is employed. While substantial amounts of enzyme reagents can be removed using either purification method, shortmer impurities cannot. This demonstrated that the tangential flow filtration methods described herein are a successful and efficient method for purification of prematurely aborted sequences during mRNA transcription.

In order to determine whether provided mRNA can be translated into the desired protein, a comparison of each of the isolated FFL mRNA constructs (TFF vs spin-column) was made. Each of the three constructs listed below were transfected into HEK293T cells and corresponding FFL protein production was assessed via FFL protein activity in the form of FFL luminescence upon exposure to luciferin (vida supra).

Figure 4:
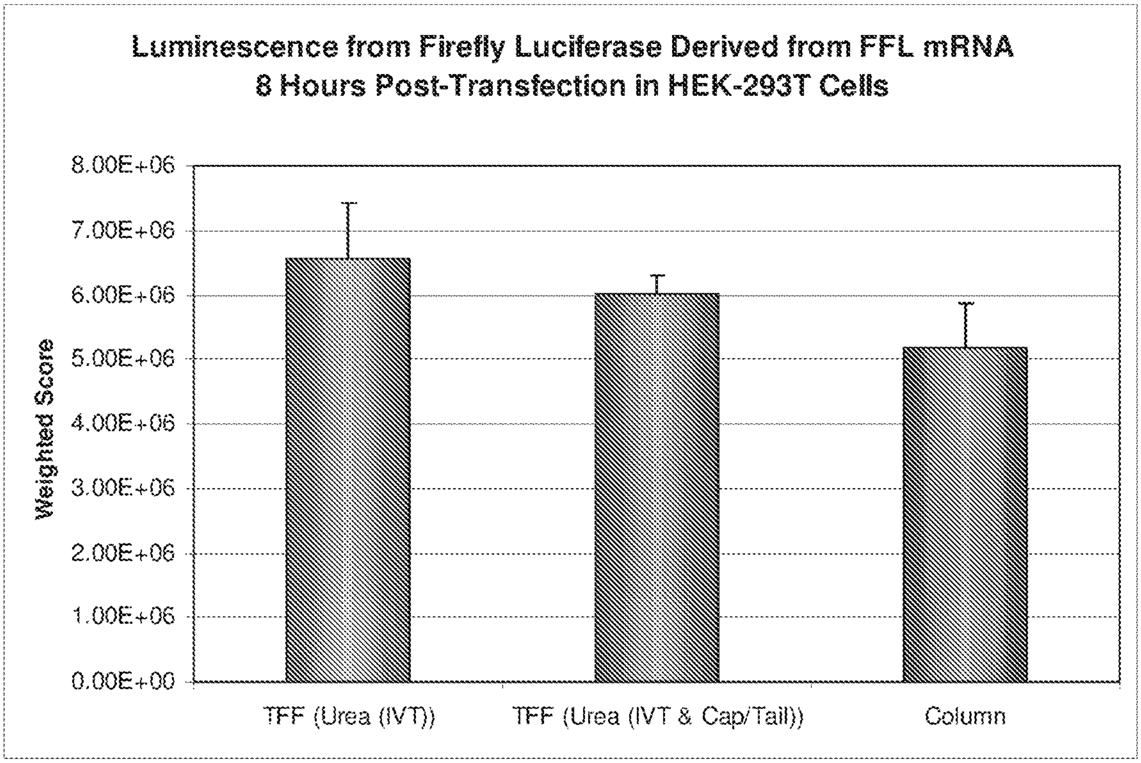
FIG. 4 depicts exemplary fluorescence data gathered from translated purified FFL mRNA provided from provided methods as compared to purified mRNA provided from traditional methods.

FFL Constructs:

1. FFL IVT purified via TFF (urea) and C/T step via TFF (no urea)
2. FFL IVT purified via TFF (urea) and C/T step via TFF (urea)
3. FFL IVT purified via spin column and C/T step via spin column A comparison of luminescence output of FFL protein produced from each is represented in FIG. 4. The integrity of the TFF-purified FFL mRNA is maintained throughout the tangential flow filtration process under the conditions described (exposure to 5M urea).

Example 4. Generation and Purification of Factor IX (FIX) mRNA

This example further illustrates that, according to various embodiments, a combination of tangential flow filtration (TFF) and a denaturing agent may be used according to provided methods to product a highly purified mRNA product. In this example, guanidinium thiocyanate is used as the protein denaturing agent.

In this example, a second species of mRNA was produced and purified, this time coding for Factor IX (SEQ ID NO: 4, below). Initially, a five milligram batch of Factor IX (FIX) RNA was transcribed via in vitro methods as described above to produce the aforementioned RNA with no cap and no polyA tail. This reaction maintained a total volume of 2.24 mL and was quenched upon completion by the addition of Proteinase K (4 mg/ml IVT reaction) which was incubated in the reaction mixture at 37° C. for 5 minutes. Upon completion, 6M guanidinium thiocyanate (4.3 mL, final ~4M) was added and the resultant solution was incubated for five minutes at room temperature and transferred to the TFF system reservoir. The sample was diluted to 200 mL with nuclease free water and washed with 1600 mL nuclease free water by ultrafiltration of 200 ml, at a time. Upon completion, the sample was concentrated to ~2 mL and the final concentration was determined via absorption at 260 nm ($\lambda_{max}$).

Human Factor IX (FIX) mRNA
(SEQ ID NO: 4)

$X_1$AUGCAGCGCGUGAACAUGAUCAUGGCAGAAUCACC
AGGCCUCAUCACCAUCUGCCUUUUAGGAUAUCUAC
UCAGUGCUGAAUGUACAGUUUUUCUUGAUCAUGAA
AACGCCAACAAAAUUCUGAGGCGGAGAAGGAGGUA
UAAUUCAGGUAAAUUGGAAGAGUUUGUUCAAGGGA
ACCUUGAGAGAGAAUGUAUGGAAGAAAAGUGUAGU
UUUGAAGAAGCACGAGAAGUUUUUGAAAACACUGA
AAGAACAACUGAAUUUUGGAAGCAGUAUGUUGAUG
GAGAUCAGUGUGAGUCCAAUCCAUGUUUAAAUGGC
GGCAGUUGCAAGGAUGACAUUAAUUCCUAUGAAUG

-continued

UUGGUGUCCCUUUGGAUUUGAAGGAAAGAACUGUG
AAUUAGAUGUAACAUGUAACAUUAAGAAUGGCAGA
UGCGAGCAGUUUUGUAAAAAUAGUGCUGAUAACAA
GGUGGUUUGCUCCUGUACUGAGGGAUAUCGACUUG
CAGAAAACCAGAAGUCCUGUGAACCAGCAGUGCCA
UUUCCAUGUGGAAGAGUUUCUGUUUCACAAACUUC
UAAGCUCACCCGUGCUGAGGCUGUUUUUCCUGAUG
UGGACUAUGUAAAUUCUACUGAAGCUGAAACCAUU
UUGGAUAACAUCACUCAAAGCACCCAAUCAUUUAA
UGACUUCACUCGGGUUGUUGGUGGAGAAGAUGCCA
AACCAGGUCAAUUCCCUUGGCAGGUUGUUUUGAAU
GGUAAAGUUGAUGCAUUCUGUGGAGGCUCUAUCGU
UAAUGAAAAAUGGAUUGUAACUGCUGCCCACUGUG
UUGAAACUGGUGUUAAAAUUACAGUUGUCGCAGGU
GAACAUAAUAUUGAGGAGACAGAACAUACAGAGCA
AAAGCGAAAUGUGAUUCGAAUUAUUCCUCACCACA
ACUACAAUGCAGCUAUUAAUAAGUACAACCAUGAC
AUUGCCCUUCUGGAACUGGACGAACCCUUAGUGCU
AAACAGCUACGUUACACCUAUUUGCAUUGCUGACA
AGGAAUACACGAACAUCUUCCUCAAAUUUGGAUCU
GGCUAUGUAAGUGGCUGGGGAAGAGUCUUCCACAA
AGGGAGAUCAGCUUUAGUUCUUCAGUACCUUAGAG
UUCCACUUGUUGACCGAGCCACAUGUCUUCGAUCU
ACAAAGUUCACCAUCUAUAACAACAUGUUCUGUGC
UGGCUUCCAUGAAGGAGGUAGAGAUUCAUGUCAAG
GAGAUAGUGGGGGACCCCAUGUUACUGAAGUGGAA
GGGACCAGUUUCUUAACUGGAAUUAUUAGCUGGGG
UGAAGAGUGUGCAAUGAAAGGCAAAUAUGGAAUAU
AUACCAAGGUAUCCCGGUAUGUCAACUGGAUUAAG
GAAAAAACAAAGCUCACUUAA$Y_1$

5' and 3' UTR Sequences:
(SEQ ID NO: 5)

$X_1$ =
GGACAGAUCGCCUGGAGACGCCAUCCACGCUGUUU
UGACCUCCAUAGAAGACACCGGGACCGAUCCAGCC
UCCGCGGCCGGGAACGGUGCAUUGGAACGCGGAUU
CCCCGUGCCAAGAGUGACUCACCGUCCUUGACACG (SEQ ID NO: 6)

$Y_1$ =
CGGGUGGCAUCCCUGUGACCCCUCCCCAGUGCCUC
UCCUGGCCCUGGAAGUUGCCACUCCAGUGCCCACC
AGCCUUGUCCUAAUAAAAUUAAGUUGCAUC

Figure 5:
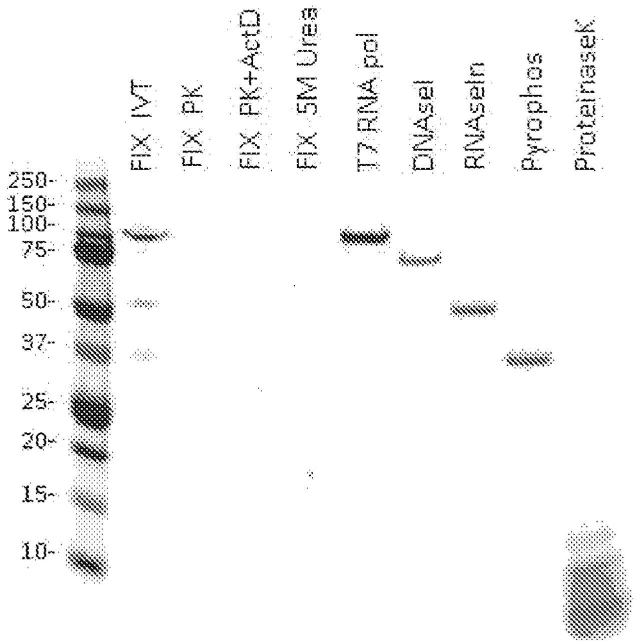
FIG. 5 shows exemplary protein levels from in vitro transcription samples of Factor IX (FIX) mRNA purified according to provided methods, including exposure to proteinase K and/or 5M Urea, as compared to mRNA purified according to traditional methods gel electrophoresis and Coomassie staining.
Figure 6:
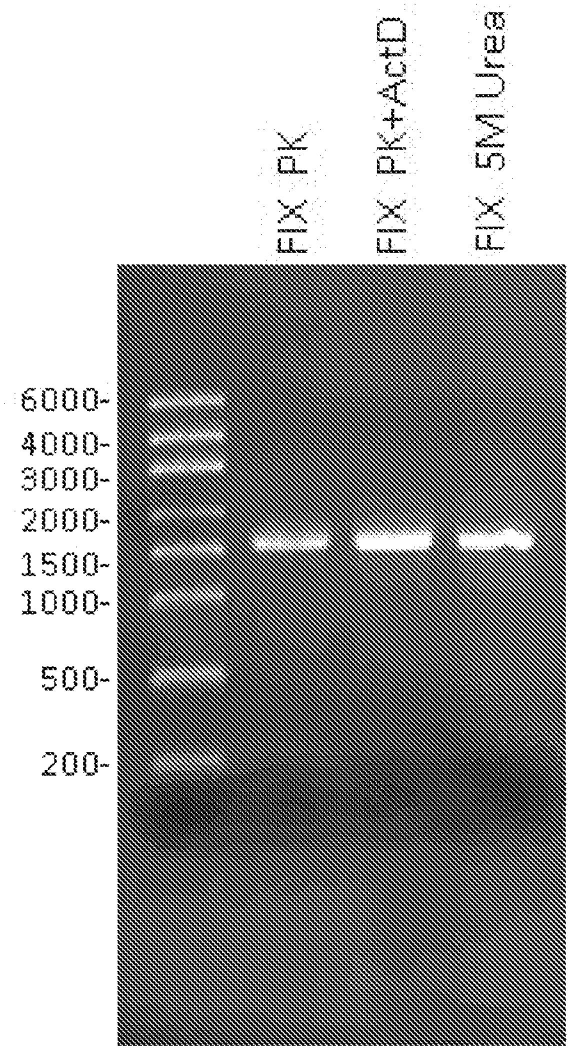
FIG. 6 shows exemplary FIX mRNA levels in in vitro transcription samples purified according to provided methods as shown by agarose gel electrophoresis and ethidium bromide staining.

The above method was also performed as described above, with the addition of actinomycin D (10 μg/ml IVT reaction) during the Proteinase K step. By quenching the IVT reaction with Proteinase K (with or without actinomycin D), one can also successfully achieve removal of all enzymes (FIG. 5). While Proteinase K may facilitate removal, large scale manufacturing of an mRNA drug substance would require this enzyme to be made at large scale incurring additional unnecessary costs, and therefore may not be a desired approach in some embodiments. As shown in FIG. 6, FIX mRNA produced as described above (with and without actinomycin D), as well as FIX mRNA purified using 5M urea, does not contain detectable levels of shortmers, similar to the results for FFL mRNA as described in Example 3.

Example 5. Generation and Purification of Cystic Fibrosis Transmembrane Conductance Regulator (CFTR) mRNA This example further illustrates that, according to various embodiments, a combination of tangential flow filtration (TFF) and a denaturing agent may be used according to provided methods to product a highly purified mRNA product. In this example, potassium chloride is used as the protein denaturing agent.

In this example, a third species of mRNA was produced and purified, this time coding for the Cystic Fibrosis Transmembrane Conductance Regulator (CFTR, SEQ ID NO: 7, below). Initially, a five milligram batch of CFTR RNA was transcribed via in vitro methods as described above to produce the aforementioned RNA with no cap and no polyA tail. This reaction maintains a total volume of 2.24 mL and was quenched upon completion by addition of 2M KCl (~200 mL). The resultant solution was incubated for five minutes at room temperature and transferred to the TFF system reservoir. The sample was diafiltrated at a constant volume of 200 mL with 2M KCL in nuclease-free water for three to four diavolumes. After this time, the resultant solution was washed with 400 mL nuclease-free water by ultrafiltration of 200 mL at a time. Following this, the sample was treated with 200 mL 1 mM Sodium Citrate (pH6.4) followed by 600 ml wash with nuclease free water. Finally, the sample was concentrated to ~2 mL and the final concentration was determined via absorption at 260 nm ($\lambda_{max}$).

Codon-Optimized Cystic Fibrosis Transmembrane Conductance Regulator (CFTR) mRNA (SEQ ID NO: 7)

$\mathbf{X}_1$AUGCAGCGGUCCCCGCUCGAAAAGGCCAGUGUCGU

GUCCAAACUCUUCUUCUCAUGGACUCGGCCUAUCCUU

AGAAAGGGGUAUCGGCAGAGGCUUGAGUUGUCUGACA

UCUACCAGAUCCCCUCGGUAGAUUCGGCGGAUAACCU

CUCGGAGAAGCUCGAACGGGAAUGGGACCGCGAACUC

GCGUCUAAGAAAAACCCGAAGCUCAUCAACGCACUGA

GAAGGUGCUUCUUCUGGCGGUUCAUGUUCUACGGUAU

CUUCUUGUAUCUCGGGGAGGUGACAAAAGCAGUCCAA

CCCGUGUUGUUGGGUCGCAUUAUCGCGUCGUACGACC

CCGAUAACAAAGAAGAACGGAGCAUCGCGAUCUACCU

CGGGAUCGGACUGUGUUUGCUUUUCAUCGUCAGAACA

-continued

CUUUUGUUGCAUCCAGCAAUCUUCGGCCUCCAUCACA

UCGGUAUGCAGAUGCGAAUCGCUAUGUUUAGCUUGAU

CUACAAAAAGACACUGAAACUCUCGUCGCGGGUGUUG

GAUAAGAUUUCCAUCGGUCAGUUGGUGUCCCUGCUUA

GUAAUAACCUCAACAAAUUCGAUGAGGGACUGGCGCU

GGCACAUUUCGUGUGGAUUGCCCCGUUGCAAGUCGCC

CUUUUGAUGGGCCUUAUUUGGGAGCUGUUGCAGGCAU

CUGCCUUUUGUGGCCUGGGAUUUCUGAUUGUGUUGGC

AUUGUUUCAGGCUGGGCUUGGGCGGAUGAUGAUGAAG

UAUCGCGACCAGAGAGCGGGUAAAAUCUCGGAAAGAC

UCGUCAUCACUUCGGAAAUGAUCGAAAACAUCCAGUC

GGUCAAAGCCUAUUGCUGGGAAGAAGCUAUGGAGAAG

AUGAUUGAAAACCUCCGCCAAACUGAGCUGAAACUGA

CCCGCAAGGCGGCGUAUGUCCGGUAUUUCAAUUCGUC

AGCGUUCUUCUUUUCCGGGUUCUUCGUUGUCUUUCUC

UCGGUUUUGCCUUAUGCCUUGAUUAAGGGGAUUAUCC

UCCGCAAGAUUUUCACCACGAUUUCGUUCUGCAUUGU

AUUGCGCAUGGCAGUGACACGGCAAUUUCCGUGGGCC

GUGCAGACAUGGUAUGACUCGCUUGGAGCGAUCAACA

AAAUCCAAGACUUCUUGCAAAAGCAAGAGUACAAGAC

CCUGGAGUACAAUCUUACUACUACGGAGGUAGUAAUG

GAGAAUGUGACGGCUUUUUGGGAAGAGGGUUUUGGAG

AACUGUUUGAGAAAGCAAAGCAGAAUAACAACAACCG

CAAGACCUCAAAUGGGGACGAUUCCCUGUUUUUCUCG

AACUUCUCCCUGCUCGGAACACCGGUGUUGAAGGACA

UCAAUUUCAAGAUUGAGAGGGGACAGCUUCUCGCGGU

AGCGGGAAGCACUGGUGCGGGAAAAACUAGCCUCUUG

AUGGUGAUUAUGGGGGAGCUUGAGCCCAGCGAGGGGA

AGAUUAAACACUCCGGGCGUAUCUCAUUCUGUAGCCA

GUUUUCAUGGAUCAUGCCCGGAACCAUUAAAGAGAAC

AUCAUUUUCGGAGUAUCCUAUGAUGAGUACCGAUACA

GAUCGGUCAUUAAGGCGUGCCAGUUGGAAGAGGACAU

UUCUAAGUUCGCCGAGAAGGAUAACAUCGUCUUGGGA

GAAGGGGGUAUUACAUUGUCGGGAGGGCAGCGAGCGC

GGAUCAGCCUCGCGAGAGCGGUAUACAAAGAUGCAGA

UUUGUAUCUGCUUGAUUCACCGUUUGGAUACCUCGAC

GUAUUGACAGAAAAAGAAAUCUUCGAGUCGUGCGUGU

GUAAACUUAUGGCUAAUAAGACGAGAAUCCUGGUGAC

AUCAAAAAUGGAACACCUUAAGAAGGCGGACAAGAUC

CUGAUCCUCCACGAAGGAUCGUCCUACUUUUACGGCA

CUUUCUCAGAGUUGCAAAACUUGCAGCCGGACUUCUC

-continued

AAGCAAACUCAUGGGGUGUGACUCAUUCGACCAGUUC

AGCGCGGAACGGCGGAACUCGAUCUUGACGGAAACGC

UGCACCGAUUCUCGCUUGAGGGUGAUGCCCCGGUAUC

GUGGACCGAGACAAAGAAGCAGUCGUUUAAGCAGACA

GGAGAAUUUGGUGAGAAAAGAAAGAACAGUAUCUUGA

AUCCUAUUAACUCAAUUCGCAAGUUCUCAAUCGUCCA

GAAAACUCCACUGCAGAUGAAUGGAAUUGAAGAGGAU

UCGGACGAACCCCUGGAGCGCAGGCUUAGCCUCGUGC

CGGAUUCAGAGCAAGGGGAGGCCAUUCUUCCCCGGAU

UUCGGUGAUUUCAACCGGACCUACACUUCAGGCGAGG

CGAAGGCAAUCCGUGCUCAACCUCAUGACGCAUUCGG

UAAACCAGGGGCAAAACAUUCACCGCAAAACGACGGC

CUCAACGAGAAAAGUGUCACUUGCACCCCAGGCGAAU

UUGACUGAACUCGACAUCUACAGCCGUAGGCUUUCGC

AAGAAACCGGACUUGAGAUCAGCGAAGAAAUCAAUGA

AGAAGAUUUGAAAGAGUGUUUCUUUGAUGACAUGGAA

UCAAUCCCAGCGGUGACAACGUGGAACACAUACUUGC

GUUACAUCACGGUGCACAAGUCCUUGAUUUUCGUCCU

CAUCUGGUGUCUCGUGAUCUUUCUCCCUGAGGUCGCA

GCGUCACUUGUGGUCCUCUGGCUGCUUGGUAAUACGC

CCUUGCAAGACAAAGGCAAUUCUACACACUCAAGAAA

CAAUUCCUAUGCCGUGAUUAUCACUUCUACAAGCUCG

UAUUACGUGUUUUACAUCUACGUAGGAGUGGCCGACA

CUCUGCUCGCGAUGGGUUUCUUCCGAGGACUCCCACU

CGUUCACACGCUUAUCACUGUCUCCAAGAUUCUCCAC

CAUAAGAUGCUUCAUAGCGUACUGCAGGCUCCCAUGU

CCACCUUGAAUACOCUCAAGGCGGGAGGUAUUUUGAA

UCGCUUCUCAAAAGAUAUUGCAAUUUUGGAUGACCUU

CUGCCCCUGACGAUCUUCGACUUCAUCCAGUUGUUGC

UGAUCGUGAUUGGGGCUAUUGCAGUAGUCGCUGUCCU

CCAGCCUUACAUUUUUGUCGCGACCGUUCCGGUGAUC

GUGGCGUUUAUCAUGCUGCGGGCCUAUUUCUUGCAGA

CGUCACAGCAGCUUAAGCAACUGGAGUCUGAAGGGAG

GUCGCCUAUCUUUACGCAUCUUGUGACCAGUUUGAAG

GGAUUGUGGACGUUGCGCGCCUUUGGCAGGCAGCCCU

ACUUUGAAACACUGUUCCACAAAGCGCUGAAUCUCCA

UACGGCAAAUUGGUUUUUGUAUUUGAGUACCCUCCGA

UGGUUUCAGAUGCGCAUUGAGAUGAUUUUUGUGAUCU

UCUUUAUCGCGGUGACUUUUAUCUCCAUCUUGACCAC

GGGAGAGGGCGAGGGACGGGUCGGUAUUAUCCUGACA

-continued

CUCGCCAUGAACAUUAUGAGCACUUUGCAGUGGGCAG

UGAACAGCUCGAUUGAUGUGGAUAGCCUGAUGAGGUC

CGUUUCGAGGGUCUUUAAGUUCAUCGACAUGCCGACG

GAGGGAAAGCCCACAAAAAGUACGAAACCCUAUAAGA

AUGGGCAAUUGAGUAAGGUAAUGAUCAUCGAGAACAG

UCACGUGAAGAAGGAUGACAUCUGGCCUAGCGGGGGU

CAGAUGACCGUGAAGGACCUGACGGCAAAAUACACCG

AGGGAGGGAACGCAAUCCUUGAAAACAUCUCGUUCAG

CAUUAGCCCCGGUCAGCGUGUGGGGUUGCUCGGGAGG

ACCGGGUCAGGAAAAUCGACGUUGCUGUCGGCCUUCU

UGAGACUUCUGAAUACAGAGGGUGAGAUCCAGAUCGA

CGGCGUUUCGUGGGAUAGCAUCACCUUGCAGCAGUGG

CGGAAAGCGUUUGGAGUAAUCCCCCAAAAGGUCUUUA

UCUUUAGCGGAACCUUCCGAAAGAAUCUCGAUCCUUA

UGAACAGUGGUCAGAUCAAGAGAUUUGGAAAGUCGCG

GACGAGGUUGGCCUUCCGAGUGUAAUCGAGCAGUUUC

CGGGAAAACUCGACUUUCUCCUUCUAGAUGGGGGAUG

CGUCCUGUCGCAUGGGCACAAGCAGCUCAUGUGCCUG

GCGCGAUCCGUCCUCUCUAAAGCGAAAAUUCUUCUCU

UGGAUGAACCUUCGGCCCAUCUGGACCCGGUAACGUA

UCAGAUCAUCAGAAGGACACUUAAGCAGGCGUUUGCC

GACUGCACGGUGAUUCUCUGUGAGCAUCGUAUCGAGG

CCAUGCUCGAAUGCCAGCAAUUUCUUGUCAUCGAAGA

GAAUAAGGUCCGCCAGUACGACUCCAUCCAGAAGCUG

CUUAAUGAGAGAUCAUUGUUCCGGCAGGCGAUUUCAC

CAUCCGAUAGGGUGAAACUUUUUCCACACAGAAAUUC

GUCGAAGUGCAAGUCCAAACCGCAGAUCGCGGCCUUG

AAAGAAGAGACUGAAGAAGAAGUUCAAGACACGCGUC

UUUAA$Y_1$

5' and 3' UTR Sequences:

(SEQ ID NO: 5)

$X_1$ =
GGACAGAUCGCCUGGAGACGCCAUCCACGCUGUUUUG

ACCUCCAUAGAAGACACCGGGACCGAUCCAGCCUCCG

CGGCCGGGAACGGUGCAUUGGAACGCGGAUUCCCCGU

GCCAAGAGUGACUCACCGUCCUUGACACG (SEQ ID NO: 6)

$Y_1$ =
CGGGUGGCAUCCCUGUGACCCCUCCCCAGUGCCUCUC

CUGGCCCUGGAAGUUGCCACUCCAGUGCCCACCAGCC

UUGUCCUAAUAAAAUUAAGUUGCAUC

Figure 7:
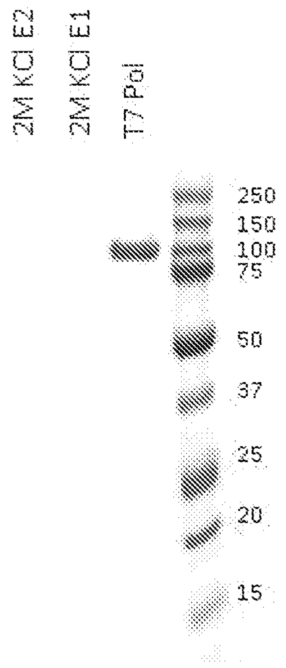
FIG. 7 shows exemplary protein levels in in vitro transcription samples of cystic fibrosis transmembrane conductance regulator (CFTR) mRNA purified according to provided methods, including exposure to 2M KCl, as compared to mRNA purified according to traditional methods gel electrophoresis and Coomassie staining.
Figure 8:
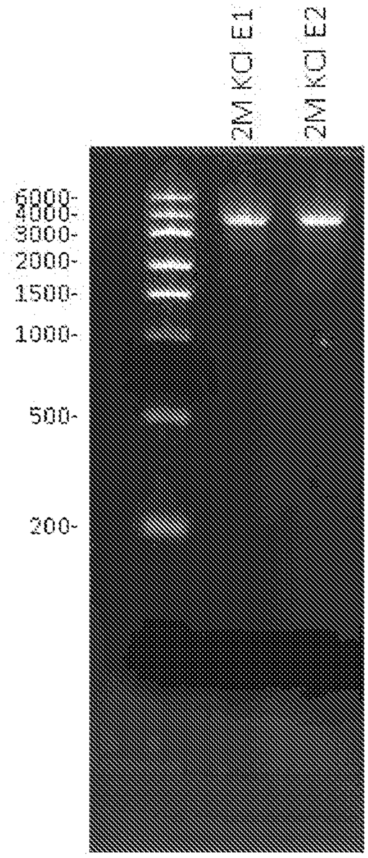
FIG. 8 shows exemplary CFTR mRNA levels in in vitro transcription samples purified according to provided methods, including exposure to 2M KCl, as shown by agarose gel electrophoresis and ethidium bromide staining.

In this example, in order to remove reaction enzymes, 2M KCl diafiltration was used. Exposure to large volumes of 2M KCl resulted in successful removal of all enzymes present in the reaction mixture (including T7 polymerase) as determined via protein gel electrophoresis (FIG. 7). As shown via agarose gel electrophoresis, the target messenger RNA remains intact after exposure to such conditions (FIG. 8).

Figure 9:
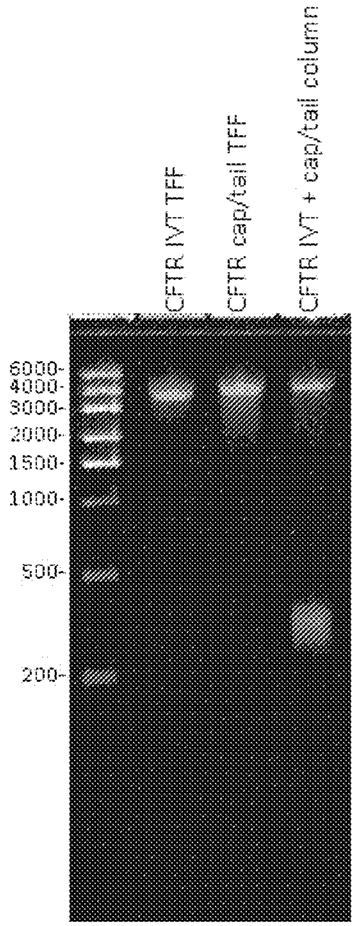
FIG. 9 shows exemplary CFTR mRNA levels in in vitro transcription samples purified according to provided methods, including exposure to 2M KCl, as compared to mRNA purified according to traditional methods as shown by agarose gel electrophoresis and ethidium bromide staining.

Further, upon capping and tailing of the CFTR IVT construct, one can successfully purify the final CFTR transcript (capped and tailed) via TFF using 2M KCl. When comparing this final isolated product to the same product purified via spin-column methods, one observes a greatly diminished "shortmer" band as determined via gel electrophoresis (FIG. 9).

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of purifying messenger RNA (mRNA), comprising (a) providing an impure preparation comprising in vitro synthesized mRNA and enzyme reagents;

(b) treating the impure preparation comprising in vitro synthesized mRNA with a denaturing agent under conditions that facilitate separation of the enzyme reagents from the mRNA; and (c) subjecting the treated impure preparation from step (b) to tangential flow filtration (TFF), thereby purifying the mRNA;

wherein the mRNA purified from step (c) is substantially free of the enzyme reagents;

wherein the mRNA is purified at a scale of 5 milligrams or greater per batch; and wherein the purified mRNA is suitable for administration as a pharmaceutical product.

2. The method of claim 1, wherein the denaturing agent is selected from the group consisting of an enzyme, an acid, a solvent, a cross-linking agent, a chaotropic agent, and at least 1M salt.

3. The method of claim 2, wherein the denaturing agent is selected from the group consisting of urea, guanidinium thiocyanate, KCl, sodium dodecyl sulfate, and combinations thereof.

4. The method of claim 3, wherein the denaturing agent is selected from the group consisting of urea, guanidinium thiocyanate, and KCl, and combinations thereof.

5. The method of claim 1, wherein the tangential flow filtration is performed using only aqueous solvents.

6. The method of claim 1, wherein the mRNA purified from step (c) contains less than 1% of enzyme reagents.

7. The method of claim 1, wherein the mRNA purified from step (c) contains less than 0.5% of enzyme reagents.

8. The method of claim 1, wherein the mRNA purified from step (c) contains less than 0.1% of enzyme reagents.

9. The method of claim 1, wherein the mRNA purified from step (c) does not contain enzyme reagents that are detectable by agarose gel electrophoresis or chromatographic methods.

10. The method of claim 1, wherein the enzyme reagents are selected from the group consisting of RNA polymerase, DNAse I, pyrophosphatase, RNAse inhibitor, and combinations thereof.

11. The method of claim 1, wherein the tangential flow filtration is performed before a cap and poly-A tail are added to the in vitro synthesized mRNA.

12. The method of claim 1, wherein the tangential flow filtration is performed after a cap and poly-A tail are added to the in vitro synthesized mRNA.

13. The method of claim 1, wherein the tangential flow filtration is performed both before and after a cap and poly-A tail are added to the in vitro synthesized mRNA.

14. The method of claim 1, wherein the in vitro synthesized mRNA is greater than about 1 kb in length.

15. The method of claim 1, wherein the in vitro synthesized mRNA comprises one or more modifications to enhance stability.

16. The method of claim 15, wherein the one or more modifications are selected from modified nucleotide, modified sugar phosphate backbone, a 5' untranslated region, and a 3' untranslated region.

17. The method of claim 1, wherein the in vitro synthesized mRNA is unmodified.

18. The method of claim 1, wherein the mRNA purified from step (c) has an integrity greater than 95%.

19. A method for manufacturing messenger RNA (mRNA) comprising:

(a) synthesizing mRNA in vitro; and (b) purifying the in vitro synthesized mRNA using a method according to claim 1, thereby manufacturing mRNA.

20. The method of claim 19, wherein the denaturing agent is selected from the group consisting of an enzyme, an acid, a solvent, a cross-linking agent, a chaotropic agent, and at least 1M salt.

21. The method of claim 20, wherein the denaturing agent is selected from the group consisting of urea, guanidinium thiocyanate, KCl, sodium dodecyl sulfate, and combinations thereof.

22. The method of claim 19, wherein the tangential flow filtration is performed using only aqueous solvents.

23. The method of claim 19, wherein the mRNA purified from step (c) contains less than 1% of enzyme reagents.

* * * * *